United States Patent
Orian-Rousseau et al.

(10) Patent No.: US 9,586,994 B2
(45) Date of Patent: *Mar. 7, 2017

(54) CD44V6-DERIVED PEPTIDES FOR TREATING BREAST CANCER

(71) Applicants: KARLSRUHER INSTITUT FÜR TECHNOLOGIE, Eggenstein-Leopoldshafen (DE); AMCURE GMBH, Eggenstein-Leopoldshafen (DE)

(72) Inventors: Veronique Orian-Rousseau, Rittershoffen (FR); Alexandra Matzke, Dettenheim (DE); Helmut Ponta, Graben-Neudorf (DE)

(73) Assignee: AMCURE GMBH, Eggenstein-Leopoldshafen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/407,330

(22) PCT Filed: Nov. 21, 2013

(86) PCT No.: PCT/EP2013/074388
§ 371 (c)(1),
(2) Date: Dec. 11, 2014

(87) PCT Pub. No.: WO2014/079931
PCT Pub. Date: May 30, 2014

(65) Prior Publication Data
US 2016/0024152 A1    Jan. 28, 2016

(30) Foreign Application Priority Data
Nov. 21, 2012 (GB) .................................. 1220891.4

(51) Int. Cl.
*A61K 38/17* (2006.01)
*A61P 35/00* (2006.01)
*C07K 7/08* (2006.01)
*C07K 14/705* (2006.01)
*C07K 7/06* (2006.01)
*A61K 38/00* (2006.01)

(52) U.S. Cl.
CPC .............. *C07K 7/08* (2013.01); *A61K 38/177* (2013.01); *C07K 7/06* (2013.01); *C07K 14/70585* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 2012/0045393 A1 | 2/2012 | Linder et al. | |
| 2012/0115794 A1* | 5/2012 | Matzke ................. | A61K 38/08 514/20.8 |

FOREIGN PATENT DOCUMENTS

| | | |
|---|---|---|
| EP | 1258255 | 11/2002 |
| EP | 1391213 | 2/2004 |
| EP | 1417974 | 5/2004 |
| EP | 1647556 | 4/2006 |
| EP | 2218457 | 8/2010 |
| EP | 2266593 | 12/2010 |
| WO | WO97/16557 | 5/1997 |
| WO | WO 00/44771 A1 | 8/2000 |
| WO | WO2005/065709 | 7/2005 |
| WO | WO 2007/121147 A2 | 10/2007 |
| WO | WO2011/022335 | 2/2011 |

OTHER PUBLICATIONS

Holliday et al., "Choosing the right cell line for breast cancer research," Br. Can. Res. 13:215 pp. 1-7 (2011).*
Reid et al., "Dual inhibition of ErbB1 (EGFR/HER1) and ErbB2 (HER2/neu)," Eur. J. Canc. 43:481-489 (2007).*
MCF-10 product literature from ThermoFischer Scientific (accessed Apr. 4, 2016 at URL thermofisher.com/us/en/home/technical-resources/cell-lines/m/cell-lines-detail-553.html; 2 pgs.).*
Breast Cancer, Merck Manual, accessed Aug. 21, 2014 at merckmanuals.com/home/womens-health-issues/breast-disorders/; 20 pgs).*
Breast Cancer Staging, American Joint Committee on Cancer, 7th ed., American Cancer Society, pp. 1-2 (2009).*
Vu et al., "Trastuxumab: updated mechanisms of action and resistance in breast cancer," Front. Oncol. 2:1-6 (Jun. 2012).*
Alexandra Matzke et al., A Five-Amino-Acid Peptide Blocks Met- and Ron-Dependent Cell Migration, Cancer Research, Jul. 15, 2005, pp. 6105-6110.
M. Tremmel et al., A CD44v6 peptide reveals a rold of CD44 in VEGFR-2 signaling and angiogenesis, Blood, vol. 114, No. 25, Sep. 22, 2009, pp. 5236-5244.
Orian-Rousseau et al., CD44, a therapeutic target for metastasizing tumours, European Journal of Cancer, Pergamon Press, Oxford, GB, vol. 46, No. 7, May 1, 2010, pp. 1271-1277.
Hoffman M., et al., CD44 Splice Variants Confer Metastatic Behaviour in Rats: Homologous Sequences are Expressed in Human Tumor Cell Lines1, Cancer Research, American Association for Cancer Research, vol. 51, No. 19, Oct. 1, 1991, pp. 5292-5297.
Anonymous, Biotechnology/Life Sciences in Baden-Wurttemberg amcure GmbH is working on a new compound against pancreatic cancer, URL:http://www.bio-pro.de/medtech/biopharma/aktuelles/index.html?lang=en&artikelid=/artikel/08196/index.htm, Jul. 2, 2012.
Margot Zoller, CD44: Can a Cancer-Initiating Cell Profit from an Abundantly Expressed Molecule?, Nature Reviews Cancer, vol. 11, No. 4, Mar. 10, 2011, pp. 254-267.

* cited by examiner

*Primary Examiner* — Julie Ha
*Assistant Examiner* — Kristina M Hellman
(74) *Attorney, Agent, or Firm* — Leason Ellis LLP

(57) ABSTRACT

The present invention relates to compounds, pharmaceutical compositions and methods for treating different forms of breast cancer.

16 Claims, 32 Drawing Sheets
(13 of 32 Drawing Sheet(s) Filed in Color)

Figure 4
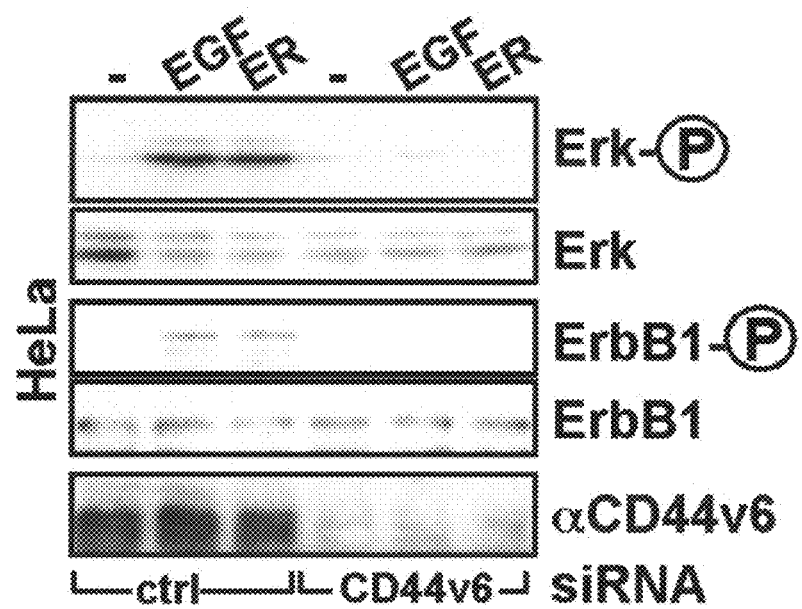
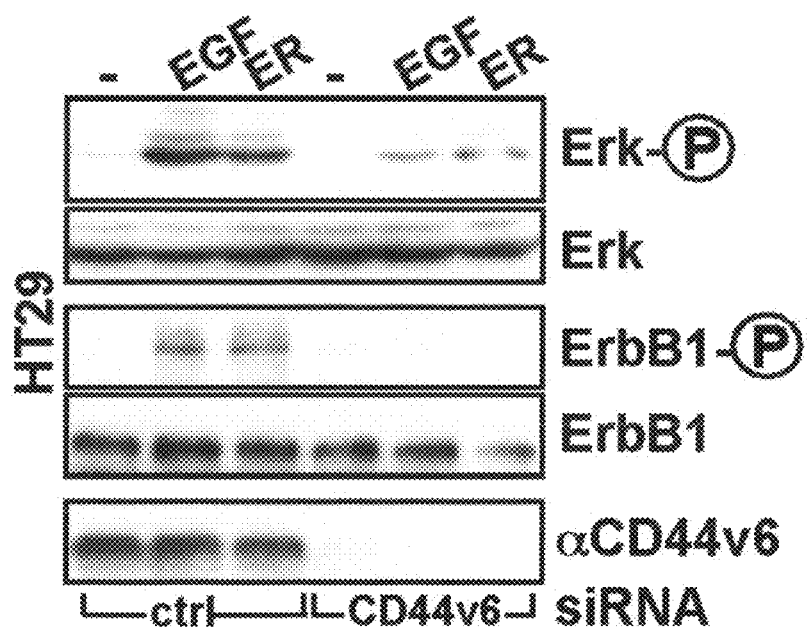

Figure 12
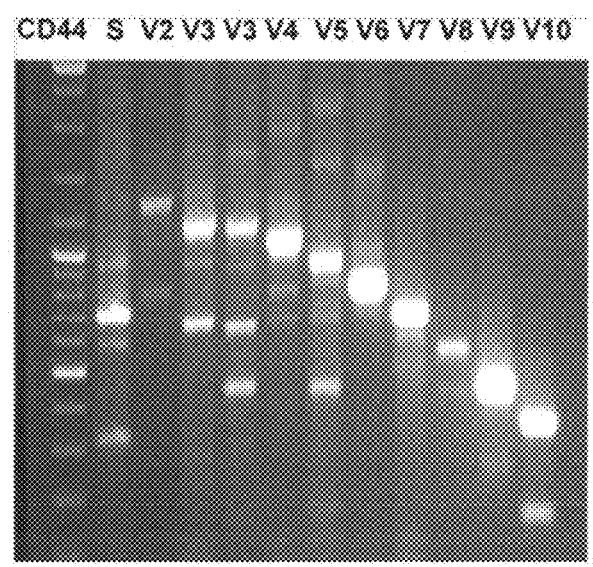
MCF7 cells
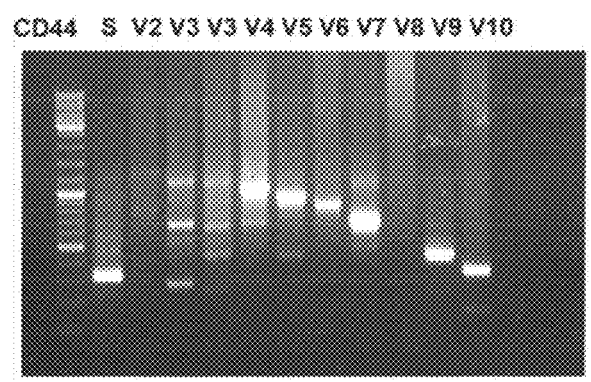
MCF10A cells

Figure 23

| Table 1 | | | | |
|---|---|---|---|---|
| cell line | primary tumor | metastasis lung | metastasis ln | micrometastasis |
| AS | 5/5 | 0/5 | 0/5 | 0/5 |
| ASs6 | 15/15 | 15/15 | 15/15 | |
| ASv1-v10Δv6 | 10/10 | 0/10 | 0/10 | 0/10 |
| ASv1-v10 | 10/10 | 10/10 | 10/10 | |
| ASs6 ctrl shRNA | 10/10 | 10/10 | 10/10 | |
| ASs6 Met shRNA | 10/10 | 0/10 | 0/10 | 0/10 |

| Table 2 | | | | |
|---|---|---|---|---|
| ASs6 +treatment | primary tumor | metastasis lung | metastasis ln | micrometastasis |
| CD44v6 Ab | 14/14 | 1/14 | 1/14 | 1/14 |
| CD44v6 pep i.t | 14/14 | 0/14 | 0/14 | 0/14 |
| CD44v6 pep i.v | 15/15 | 0/15 | 0/15 | 0/15 |
| ctrl pep | 15/15 | 15/15 | 15/15 | |
| PBS | 10/10 | 10/10 | 10/10 | |

| Table 3 | BSp73ASs6 | | L3.6pl | |
|---|---|---|---|---|
| | primary tumor | lung metastasis | primary tumor | liver metastasis |
| control (3 weeks after tumor cell injection) | 10/10 | 10/10 | 10/10 | 10/10 |
| ctrl peptide treatment (3 more weeks) | 15/15 | 15/15 | 15/15 | 15/15 |
| v6 peptide treatment (3 more weeks) | 15/15 | 1/15 | 15/15 | 1/15 |

Figure 28
A
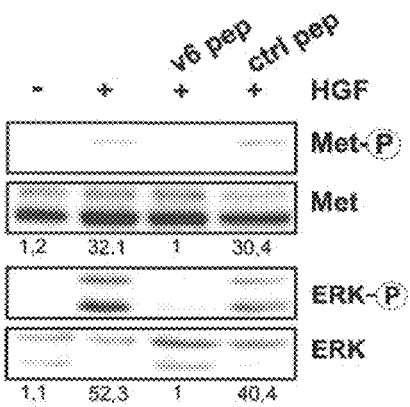
B
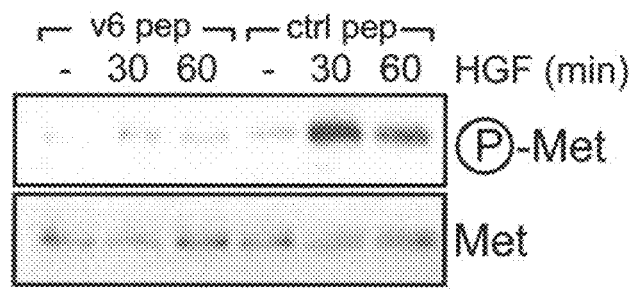
C
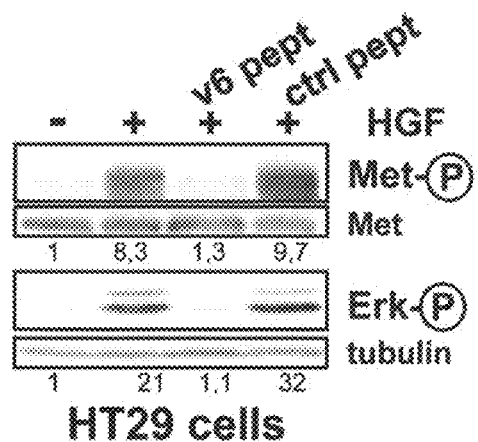
HT29 cells

```
                        SEQUENCE LISTING

<160> NUMBER OF SEQ ID NOS: 23

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Asn, Ala, Cys, Asp, Glu, Phe, Gly, His, Ile,
      Lys, Leu, Met, Pro, Gln, Arg, Ser, Thr, Val, Trp or Tyr
<220> FEATURE:
<221> NAME/KEY: MOD_RES
<222> LOCATION: (5)..(5)
<223> OTHER INFORMATION: Glu, Ala, Cys, Asp, Phe, Gly, His, Ile, Lys,
      Leu, Met, Asn, Pro, Gln, Arg, Ser, Thr, Val, Trp or Tyr

<400> SEQUENCE: 1

Xaa Arg Trp His Xaa
1               5

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Asn Arg Trp His Glu
1               5

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3
```

```
Ala Arg Trp His Ala
1               5

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Asn, Lys, Arg, Gln, Ala, Val, Leu or Ile
<220> FEATURE:
<221> NAME/KEY: MOD_RES
<222> LOCATION: (5)..(5)
<223> OTHER INFORMATION: Glu, Asp, Ala, Val, Leu or Ile

<400> SEQUENCE: 4

Xaa Arg Trp His Xaa
1               5

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Asn, Lys, Arg or Gln
<220> FEATURE:
<221> NAME/KEY: MOD_RES
<222> LOCATION: (5)..(5)
<223> OTHER INFORMATION: Glu or Asp

<400> SEQUENCE: 5

Xaa Arg Trp His Xaa
1               5

<210> SEQ ID NO 6
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Lys Glu Gln Trp Phe Gly Asn Arg Trp His Glu Gly Tyr Arg
1               5                   10

<210> SEQ ID NO 7
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys, Ala, Cys, Asp, Glu, Phe, Gly, His, Ile,
      Leu, Met, Asn, Pro, Gln, Arg, Ser, Thr, Val, Trp or Tyr
<220> FEATURE:
<221> NAME/KEY: MOD_RES
<222> LOCATION: (2)..(2)
<223> OTHER INFORMATION: Glu, Ala, Cys, Asp, Phe, Gly, His, Ile, Lys,
```

```
      Leu, Met, Asn, Pro, Gln, Arg, Ser, Thr, Val, Trp or Tyr
<220> FEATURE:
<221> NAME/KEY: MOD_RES
<222> LOCATION: (3)..(3)
<223> OTHER INFORMATION: Gln, Ala, Cys, Asp, Glu, Phe, Gly, His, Ile,
      Lys, Leu, Met, Asn, Pro, Arg, Ser, Thr, Val, Trp or Tyr
<220> FEATURE:
<221> NAME/KEY: MOD_RES
<222> LOCATION: (4)..(4)
<223> OTHER INFORMATION: Trp, Ala, Cys, Asp, Glu, Phe, Gly, His, Ile,
      Lys, Leu, Met, Asn, Pro, Gln, Arg, Ser, Thr, Val or Tyr
<220> FEATURE:
<221> NAME/KEY: MOD_RES
<222> LOCATION: (5)..(5)
<223> OTHER INFORMATION: Phe, Ala, Cys, Asp, Glu, Gly, His, Ile, Lys,
      Leu, Met, Asn, Pro, Gln, Arg, Ser, Thr, Val, Trp or Tyr
<220> FEATURE:
<221> NAME/KEY: MOD_RES
<222> LOCATION: (6)..(6)
<223> OTHER INFORMATION: Gly, Ala, Cys, Asp, Glu, Phe, His, Ile, Lys,
      Leu, Met, Asn, Pro, Gln, Arg, Ser, Thr, Val, Trp or Tyr
<220> FEATURE:
<221> NAME/KEY: MOD_RES
<222> LOCATION: (7)..(7)
<223> OTHER INFORMATION: Asn, Ala, Cys, Asp, Glu, Phe, Gly, His, Ile,
      Lys, Leu, Met, Pro, Gln, Arg, Ser, Thr, Val, Trp or Tyr
<220> FEATURE:
<221> NAME/KEY: MOD_RES
<222> LOCATION: (11)..(11)
<223> OTHER INFORMATION: Glu, Ala, Cys, Asp, Phe, Gly, His, Ile, Lys,
      Leu, Met, Asn, Pro, Arg, Ser, Thr, Val, Trp or Tyr
<220> FEATURE:
<221> NAME/KEY: MOD_RES
<222> LOCATION: (12)..(12)
<223> OTHER INFORMATION: Gly, Ala, Cys, Asp, Glu, Phe, His, Ile, Lys,
      Leu, Met, Asn, Pro, Gln, Arg, Ser, Thr, Val, Trp or Tyr
<220> FEATURE:
<221> NAME/KEY: MOD_RES
<222> LOCATION: (13)..(13)
<223> OTHER INFORMATION: Tyr, Ala, Cys, Asp, Glu, Phe, Gly, His, Ile,
      Lys, Leu, Met, Asn, Pro, Gln, Arg, Ser, Thr, Val or Trp
<220> FEATURE:
<221> NAME/KEY: MOD_RES
<222> LOCATION: (14)..(14)
<223> OTHER INFORMATION: Arg, Ala, Cys, Asp, Glu, Phe, Gly, His, Ile,
      Lys, Leu, Met, Asn, Pro, Gln, Ser, Thr, Val, Trp or Tyr

<400> SEQUENCE: 7

Xaa Xaa Xaa Xaa Xaa Xaa Xaa Arg Trp His Xaa Xaa Xaa Xaa
1               5                   10

<210> SEQ ID NO 8
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys, Arg, Asn, Gln, Ala, Val, Leu or Ile
<220> FEATURE:
<221> NAME/KEY: MOD_RES
<222> LOCATION: (2)..(2)
<223> OTHER INFORMATION: Glu, Asp, Ala, Val, Leu or Ile
<220> FEATURE:
<221> NAME/KEY: MOD_RES
<222> LOCATION: (3)..(3)
<223> OTHER INFORMATION: Gln, Lys, Arg, Asn, Ala, Val, Leu or Ile
<220> FEATURE:
<221> NAME/KEY: MOD_RES
<222> LOCATION: (4)..(4)
<223> OTHER INFORMATION: Trp, Phe, Tyr, Ala, Val, Leu or Ile
<220> FEATURE:
<221> NAME/KEY: MOD_RES
<222> LOCATION: (5)..(5)
```

-continued

```
<223> OTHER INFORMATION: Phe, Trp, Tyr, Ala, Val, Leu or Ile
<220> FEATURE:
<221> NAME/KEY: MOD_RES
<222> LOCATION: (6)..(6)
<223> OTHER INFORMATION: Gly, Ala, Val, Leu or Ile
<220> FEATURE:
<221> NAME/KEY: MOD_RES
<222> LOCATION: (7)..(7)
<223> OTHER INFORMATION: Asn, Lys, Arg, Gln, Ala, Val, Leu or Ile
<220> FEATURE:
<221> NAME/KEY: MOD_RES
<222> LOCATION: (11)..(11)
<223> OTHER INFORMATION: Glu, Asp, Ala, Val, Leu or Ile
<220> FEATURE:
<221> NAME/KEY: MOD_RES
<222> LOCATION: (12)..(12)
<223> OTHER INFORMATION: Gly, Ala, Val, Leu or Ile
<220> FEATURE:
<221> NAME/KEY: MOD_RES
<222> LOCATION: (13)..(13)
<223> OTHER INFORMATION: Tyr, Phe, Trp, Ala, Val, Leu or Ile
<220> FEATURE:
<221> NAME/KEY: MOD_RES
<222> LOCATION: (14)..(14)
<223> OTHER INFORMATION: Arg, Lys, Asn, Gln, Ala, Val, Leu or Ile

<400> SEQUENCE: 8

Xaa Xaa Xaa Xaa Xaa Xaa Xaa Arg Trp His Xaa Xaa Xaa Xaa
1               5                   10

<210> SEQ ID NO 9
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys, Arg, Asn or Gln
<220> FEATURE:
<221> NAME/KEY: MOD_RES
<222> LOCATION: (2)..(2)
<223> OTHER INFORMATION: Glu or Asp
<220> FEATURE:
<221> NAME/KEY: MOD_RES
<222> LOCATION: (3)..(3)
<223> OTHER INFORMATION: Gln, Lys, Arg or Asn
<220> FEATURE:
<221> NAME/KEY: MOD_RES
<222> LOCATION: (4)..(4)
<223> OTHER INFORMATION: Trp, Phe or Tyr
<220> FEATURE:
<221> NAME/KEY: MOD_RES
<222> LOCATION: (5)..(5)
<223> OTHER INFORMATION: Phe, Trp or Tyr
<220> FEATURE:
<221> NAME/KEY: MOD_RES
<222> LOCATION: (6)..(6)
<223> OTHER INFORMATION: Gly, Ala, Val, Leu or Ile
<220> FEATURE:
<221> NAME/KEY: MOD_RES
<222> LOCATION: (7)..(7)
<223> OTHER INFORMATION: Asn, Lys, Arg or Gln
<220> FEATURE:
<221> NAME/KEY: MOD_RES
<222> LOCATION: (11)..(11)
<223> OTHER INFORMATION: Glu or Asp
<220> FEATURE:
<221> NAME/KEY: MOD_RES
<222> LOCATION: (12)..(12)
<223> OTHER INFORMATION: Gly, Ala, Val, Leu or Ile
<220> FEATURE:
<221> NAME/KEY: MOD_RES
<222> LOCATION: (13)..(13)
<223> OTHER INFORMATION: Tyr, Phe or Trp
```

```
<220> FEATURE:
<221> NAME/KEY: MOD_RES
<222> LOCATION: (14)..(14)
<223> OTHER INFORMATION: Arg, Lys, Asn or Gln

<400> SEQUENCE: 9

Xaa Xaa Xaa Xaa Xaa Xaa Xaa Arg Trp His Xaa Xaa Xaa Xaa
1               5                   10

<210> SEQ ID NO 10
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Lys Glu Lys Trp Phe Glu Asn Glu Trp Gln Gly Lys Asn Pro
1               5                   10

<210> SEQ ID NO 11
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Asn Glu Trp Gln Gly
1               5

<210> SEQ ID NO 12
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Trp Phe Glu Asn Glu Trp Gln Gly Lys Asn Pro
1               5                   10

<210> SEQ ID NO 13
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Trp Phe Gln Asn Gly Trp Gln Gly Lys Asn Pro
1               5                   10

<210> SEQ ID NO 14
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Trp Phe Gly Asn Arg Trp His Glu Gly Tyr Arg
1               5                   10
```

<210> SEQ ID NO 15
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Asn Ala Ala Ala Gly
1               5

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA oligonucleotide
<220> FEATURE:
<223> OTHER INFORMATION: Description of Combined DNA/RNA Molecule:
      Synthetic siRNA oligonucleotide

<400> SEQUENCE: 16
aguaguacaa cggaagaaat t                                             21

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA oligonucleotide
<220> FEATURE:
<223> OTHER INFORMATION: Description of Combined DNA/RNA Molecule:
      Synthetic siRNA oligonucleotide

<400> SEQUENCE: 17
ggauaucgcc aaacacccat t                                             21

<210> SEQ ID NO 18
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA oligonucleotide

<400> SEQUENCE: 18
aggcauugau gaugaugaau u                                             21

<210> SEQ ID NO 19
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA oligonucleotide

<400> SEQUENCE: 19
ugaagaugaa agagacagau u                                             21

<210> SEQ ID NO 20
<211> LENGTH: 20
<212> TYPE: DNA
<213> ORGANISM: Artificial Sequence
<220> FEATURE:

```
<223> OTHER INFORMATION: Description of Artificial Sequence: Synthetic
      primer

<400> SEQUENCE: 20
cgcttcagcc tactgcaaat                                              20

<210> SEQ ID NO 21
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Phe Gly Asn Arg Trp His Glu Gly
1               5

<210> SEQ ID NO 22
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Ala, Cys, Asp, Glu, Gly, His, Ile, Lys,
      Leu, Met, Asn, Pro, Gln, Arg, Ser, Thr, Val, Trp or Tyr
<220> FEATURE:
<221> NAME/KEY: MOD_RES
<222> LOCATION: (2)..(2)
<223> OTHER INFORMATION: Gly, Ala, Cys, Asp, Glu, Phe, His, Ile, Lys,
      Leu, Met, Asn, Pro, Gln, Arg, Ser, Thr, Val, Trp or Tyr
<220> FEATURE:
<221> NAME/KEY: MOD_RES
<222> LOCATION: (3)..(3)
<223> OTHER INFORMATION: Asn, Ala, Cys, Asp, Glu, Phe, Gly, His, Ile,
      Lys, Leu, Met, Pro, Gln, Arg, Ser, Thr, Val, Trp or Tyr
<220> FEATURE:
<221> NAME/KEY: MOD_RES
<222> LOCATION: (7)..(7)
<223> OTHER INFORMATION: Glu, Ala, Cys, Asp, Phe, Gly, His, Ile, Lys,
      Leu, Met, Asn, Pro, Gln, Arg, Ser, Thr, Val, Trp or Tyr
<220> FEATURE:
<221> NAME/KEY: MOD_RES
<222> LOCATION: (8)..(8)
<223> OTHER INFORMATION: Gly, Ala, Cys, Asp, Glu, Phe, His, Ile, Lys,
      Leu, Met, Asn, Pro, Gln, Arg, Ser, Thr, Val, Trp or Tyr

<400> SEQUENCE: 22

Xaa Xaa Xaa Arg Trp His Xaa Xaa
1               5

<210> SEQ ID NO 23
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Lys Gly Asn Arg Trp His Glu Gly
1               5
```

US 9,586,994 B2

CD44V6-DERIVED PEPTIDES FOR TREATING BREAST CANCER

CROSS-REFERENCE TO RELATED PATENT APPLICATIONS

This application is a U.S. National Phase Application under 35 U.S.C. §371 of International Patent Application No. PCT/EP2013/074388, filed Nov. 21, 2013, and claims priority to GB 1220891.4 filed Nov. 21, 2012, which is incorporated by reference in its entirety. The International Application was published on May 30, 2014, as International Publication No. WO/2014/079931.

TECHNICAL FIELD OF THE INVENTION

The present invention relates to compounds, pharmaceutical compositions and methods for treating breast cancer.

BACKGROUND OF THE INVENTION

Different types of cancer have been shown to involve at least in part over-activation of receptor-tyrosine-kinases such as cMET, VEGFR, and members of the ErbB-family such as ErbB1 and ErbB2. Cancers include e.g. colorectal cancer, breast cancer, and pancreatic cancer.

The ErbB-family is also designated the subclass I of the receptor tyrosine kinase superfamily. It contains four different receptor proteins: EGFR or ErB1, ErbB2, ErbB3 and ErbB4. In rodents the ErbB2 receptor is referred to as "Neu". The human forms of the ErbBs are named Her 1-4.

In vertebrates, the "EGF-related ligand family" constitutes the ligands of the ErbB receptors. All these growth factors are produced as transmembrane precursors. Their ectodomains are processed by proteolysis, a step that leads to the shedding of the mature soluble protein. Various studies have identified the ADAM metalloproteinases as being responsible for the cleavage of the ErbB pro-ligands. The ErbB ligands differ in their ability to bind to the ErbB receptors. Based on this binding specificity they can be divided into three groups (reviewed in Olayioye et al., 2000, see references and FIG. 1). The ErbB ligands usually act over short distances as autocrine or paracrine factors. Some ligands like e.g. EGF that is found in all body fluids or Nrg-1 are widely expressed. Also Epiregulin, TGFα and HB-EGF are expressed in many different cell types. ER is expressed in macrophages and in the placenta. TGFα is produced for example in brain cells and keratinocytes, whereas HB-EGF is for example produced by macrophages and keratinocytes. Other ErbB ligands show a more restricted pattern.

The activation of the ErbB receptors, particularly ErbB1 and 2 is deregulated in many human cancers. This deregulation, caused by either overexpression or mutations of the ErbB encoded proteins or by autocrine ligand production, and is characterized by uncontrolled proliferation and migration of cancer cells. The most common type of ErbB1 mutations is the so-called type III mutation. In this case, a deletion of the extracellular domain of the protein leads to constitutive activation of the receptor. ErbB1 proteins carrying a type III mutation are involved in glioma, ovarian, as well as breast cancer (Ekstrand et al, 1992; see references).

Overexpression of ErbB1 on the other hand has been found in squamous-cell carcinomas of head and neck, non-small cell lung cancer, ovarian, lung and breast cancer. While overexpressed, the ErbB1 receptor is still dependent on induction through a ligand in order to signal. The ErbB1 receptor is co-expressed with several of its ligands. TGFα for example is often found to form an autocrine loop that leads to the deregulated activation of ErbB1, for example in lung, colon and breast cancer (Salomon et al, 1995; Umekita et al, 2000).

In contrast to the ErbB1 receptor, no activating mutation has been found for ErbB2 so far. Its activation is mainly due to overexpression, often by means of gene amplification. The increased abundance of ErbB2 molecules in target cells leads to spontaneous dimerization of the ErbB2 proteins and constitutive activation. This kind of receptor activation is found for example in lung, ovarian and stomach cancer, but is especially important in breast cancer where it has been linked to a poor clinical prognosis and resistance to therapy (Ross & Fletcher, 1998, see references).

The ErbB3 receptor has been connected with a resistance against therapies targeting the ErbB2 receptor. Upon blocking of the ErbB2 receptor for example by tyrosine kinase inhibitors (TKIs), the ErbB3 phosphorylation level is increased. This leads to an activation of ErbB3 signaling that promotes cell survival in absence of ErbB2 signaling. In breast cancer, the ErbB3 receptor has been shown to work together with ErbB2, mediating tumor cell division. Their co-expression has been found in many human breast cancers (Sithanandam & Anderson, 2008, see references).

Treatment of breast cancer depends on the underlying molecular mechanisms. Estrogen-receptor dependent breast cancer can be treated e.g. with tamoxifen. ErbB-receptor positive cancers can be treated e.g. with Herceptin®. However, it is known that patients can develop resistance against treatment with e.g. Herceptin®.

Thus, there is a continuing interest and need for pharmaceutically active agents that allow treatment of breast cancers. There is in particular a continuing need for pharmaceutically active agents that allow to selectively address the specific molecular mechanisms underlying types of breast cancer, which on the phenotypic level may not be distinguishable, but are clearly different on the molecular level. There is moreover a need for pharmaceutically active agents that allow treatment of breast cancer patients which have developed resistance against treatment with Herceptin® or small molecule inhibitors of receptor tyrosine kinases (RTK), that inhibit ErbB receptors.

OBJECTIVE AND SUMMARY OF THE INVENTION

It is one objective of the present invention to provide compounds, and pharmaceutical compositions comprising such compounds, which can be used for the treatment of breast cancers.

It is a further objective of the present invention to provide compounds, and pharmaceutical compositions comprising such compounds, which can be used for the treatment of specific types of breast cancers by selectively addressing the specific molecular mechanisms underlying types of breast cancer Yet another objective of the present invention is to provide compounds, and pharmaceutical compositions comprising such compounds, that allow treatment of breast cancer patients, which have developed resistance against treatment with Herceptin® or small molecule inhibitors of receptor tyrosine kinases (RTK), that inhibit ErbB receptors.

Another objective of the present invention is to provide new Methods for treating breast cancer in a human being, particularly new Methods for treating breast cancer patients which have developed resistance against treatment with Herceptin® or small molecule inhibitors of receptor tyrosine kinases (RTK), that inhibit ErbB receptors. It is also an objective of the present invention to provide new Methods for treating breast cancer in patients, which have developed resistance against treatment with Herceptin® or small molecule inhibitors of receptor tyrosine kinases (RTK), that inhibit ErbB receptors.

These and other objectives as they will become apparent from the ensuing description are attained by the subject matter of the independent claims. Some of the preferred embodiments of the present invention are mentioned in the dependent claims.

The present invention, to some extent, is based on the experimental data described hereinafter that in part aim to elucidate the molecular function of the co-receptor molecule CD44v6, which has broad implications as to optimization of breast cancer treatment in a patient-individualized manner.

It is inter alia shown in the experiments that CD44v6 enables the activation of the ErbB receptors through EGF in several breast cancer cell lines. It seems therefore reasonable to assume that CD44v6 may play a role in breast cancer types that are dependent on EGF-based ErbB activation for their tumorgenicity. The data further suggest that in cancer types where the activation of the ErbB-receptors is mediated by TGFα for example, CD44v6 would not be needed as a co-receptor since TGFα is independent of CD44. This finding is important, as a common type of breast cancer involves the expression of TGFα in an autocrine loop in order to stimulate breast cancer cell growth (Umekita et al, 2000, see references). Thus, the findings of the present invention may allow a more selective and patient-optimized treatment of different breast cancer types by e.g. considering to not treat patients with increased expression of TGFα. As in the case of constitutive ErbB2 activation, a common type of unregulated ErbB signaling in breast cancer, a ligand is not needed in order to activate the ErbB2 receptor, it can be considered to not also use the compounds described herein for treatment of such cancers. Further, breast cancer patients are treated with antibodies directed against the ErbB2 receptor like for example Trastuzumab or Pertuzumab to block aberrant ErbB2 signaling. Treatment of breast cancer patients with these antibodies is not always successful because patients can develop resistance to the therapy. In these patients, in particular if the overexpress Met, a peptide blocking CD44v6 would be a useful tool since CD44v6 does not only act as a co-receptor for EGF- and ER-based ErbB2-signaling, but is also instrumental in Met activation.

The experiments described hereinafter further show that a peptide having as a minimal requirement the tri-peptide sequence R-W-H being embedded in a 5-amino acid peptide backbone such as N-R-W-H-E (SEQ ID NO: 2) is capable of blocking the formation of metastases in an animal model of human pancreatic cancer. Furthermore, the data described herein show that in an orthotopic model of a human pancreatic cancer in mice, these peptides also allow efficient regression of metastases that have already spread and formed across the body. Before this background it seems reasonable to conclude that these peptides will allow regression of metastases, which have formed and spreaded across the body, not only for pancreatic cancer, but also for other metastasizing cancers such as breast cancer, and in particular the breast cancer forms described herein, namely breast cancer types that are dependent on EGF-based ErbB activation for their tumorgenicity. Preferably, such metastasizing breast cancers do not show an increased expression or activation of TGFα. Another preferred embodiment relates to metastasizing breast cancers, which are resistant to treatment with Trastuzumab or Pertuzumab and which increased expression of Met.

As already mentioned above it has been found that the peptides described herein are efficient not only for inhibiting metastasis but also for actually removing already formed metastases if the tri-peptide sequence R-W-H is embedded in a 5-amino acid peptide backbone. This was found by changing the amino acids N and E of the pentapeptide N-R-W-H-E (SEQ ID NO: 2) to A (SEQ ID NO: 3) respectively. Even though these were non-conservative amino acid substitution, the peptide is still active in inhibiting CD44v6 mediated activation of Met. Thus, it seems justified to conclude that the N in the first position of the pentapeptide N-R-W-H-E (SEQ ID NO: 2) can not only be conservatively substituted by amino acids, such as K, R, or Q but also by any other amino acids or amino acids with non-polar side chains that are comparable to A such as V, L or I. The same considerations of course apply to the fifth position in the pentapeptide such that the amino acid E may not only be replaced by a conservative substitution, such as by K, but also by any other amino acid or particularly amino acids resembling the properties of alanine such as V, L or I.

Further, the pentapeptide N-R-W-H-E (SEQ ID NO: 2) has also been shown to be effective for inhibiting CD44v6-mediated activation of Met signaling when being embedded in a larger peptide, the upper limit of which is reasonably to assume being a 14 mer. Given the findings of the possibility to substitute the first and last position in the pentapeptide not only by conservative amino acid substitutions, but also by non-conservative amino acid substitutions, it seems reasonable to conclude that any amino acid outside the essential motive of R-W-H could be replaced according to the same reasoning.

Thus, the present invention in one embodiment thus relates to a compound for use in treating breast cancer in a human being,
wherein said compound comprises:
a peptide comprising at least the amino acid sequence $X_1$-R-W-H-$X_5$ (SEQ ID NO: 1) with $X_1$ being selected from the group comprising A, C, D, E, F, G, H, I, K, L, M, N, P, Q, R, S, T, V, W, or Y and $X_5$ being selected from the group comprising A, C, D, E, F, G, H, I, K, L, M, N, P, Q, R, S, T, V, W, or Y, or a peptidomimetic thereof, or
a peptide comprising at least 5, 6, 7, 8, 9, 10, 11, 12, 13, or 14 amino acids of amino acid sequence $X_1$-$X_2$-$X_3$-$X_4$-$X_5$-$X_6$-$X_7$-R-W-H-$X_{11}$-$X_{12}$-$X_{13}$-$X_{14}$ (SEQ ID NO: 7), wherein $X_1$, $X_2$, $X_3$, $X_4$, $X_5$, $X_6$, $X_7$, $X_{11}$, $X_{12}$, $X_{13}$, or $X_{14}$ is selected from the group comprising A, C, D, E, F, G, H, I, K, L, M, N, P, Q, R, S, T, V, W, or Y, and wherein the peptide comprises at least $X_7$-R-W-H-$X_{11}$ of SEQ ID NO: 7, wherein $X_7$, and $X_{11}$ is selected from the group comprising A, C, D, E, F, G, H, I, K, L, M, N, P, Q, R, S, T, V, W, or Y, or a peptidomimetic thereof.

Such breast cancers may include breast cancer forms, that are dependent on EGF-based ErbB activation for their tumorgenicity, that do not show an increased expression or activation of TGFα, and/or that are resistant to treatment with Trastuzumab or Pertuzumab and which show increased expression of Met. In one embodiment, the invention considers to inhibit formation of metastases in such patients. In another embodiment, these breast cancer types are metastasizing, i.e. metastases have already formed, breast cancers, which may be classifiable as Stage IV according to the TNM anatomic/prognostic group system of the cancer staging system of the American Joint Committee on Cancer. For such metastasizing cancers, the compounds of the invention may lead to a regression of the already formed metastases. Preferably all these breast cancer types show expression of CD44v6.

Given the observations described above, namely that the amino acid N and amino acid E in the pentapeptide N-R-W-H-E (SEQ ID NO: 2) can be replaced by alanine (SEQ ID NO: 3), it seems reasonable to assume that peptides that comprise in these positions either conservative amino acid substitutions or amino acid substitutions, which in terms of their physical chemical properties are comparable to alanine, such as V, L, or I will also provide the same activity as N-R-W-H-E (SEQ ID NO: 2). The same considerations apply to peptides derived from the 14 mer for positions that flank the essential tripeptide motive R-W-H.

Thus, in a preferred embodiment the present invention relates to a compound for use in treating breast cancer in a human being, wherein said compound comprises:

a peptide comprising at least the amino acid sequence $X_1$-R-W-H-$X_5$ (SEQ ID NO: 4), wherein $X_1$ is selected from the group comprising amino acids with an $NH_2$ group such as K, R, N, or Q, or amino acids with non-polar side chains such as A, V, L or I and wherein $X_5$ is selected from the group comprising amino acids with negatively charged side chains such as E or D, or amino acids with non-polar side chains such as A, V, L or I or a peptidomimetic thereof, or a peptide comprising at least 5, 6, 7, 8, 9, 10, 11, 12, 13, or 14 amino acids of amino acid sequence $X_1$-$X_2$-$X_3$-$X_4$-$X_5$-$X_6$-$X_7$-R-W-H-$X_{11}$-$X_{12}$-$X_{13}$-$X_{14}$ (SEQ ID NO: 8), wherein $X_1$ is selected from the group comprising amino acids with an $NH_2$ group such as K, R, N, or Q, or amino acids with non-polar side chains such as A, V, L or I, wherein $X_2$ is selected from the group comprising amino acids with negatively charged side chains such as E or D, or amino acids with non-polar side chains such as A, V, L or I, wherein $X_3$ is selected from the group comprising amino acids with an $NH_2$ group such as K, R, N, or Q, or amino acids with non-polar side chains such as A, V, L or I, wherein $X_4$ is selected from the group comprising amino acids with non-polar or non-charged side chains and aromatic ring structures such as F, W, or Y, or amino acids with non-polar side chains such as A, V, L or I, wherein $X_5$ is selected from the group comprising amino acids with non-polar or non-charged side chains and aromatic rings structures such as F, W, or Y, or amino acids with non-polar side chains such as A, V, L or I, wherein $X_6$ is selected from the group comprising G or amino acids with non-polar side chains such as A, V, L or I, wherein $X_7$ is selected from the group comprising amino acids with an $NH_2$ group such as K, R, N, or Q, or amino acids with non-polar side chains such as A, V, L or I, wherein $X_{11}$ is selected from the group comprising amino acids with negatively charged side chains such as E or D, or amino acids with non-polar side chains such as A, V, L or I, wherein $X_{12}$ is selected from the group comprising G or amino acids with non-polar side chains such as A, V, L or I, wherein $X_{13}$ is selected from the group comprising amino acids with non-polar or non-charged side chains and aromatic rings structures such F, W, or Y, or amino acids with non-polar side chains such as A, V, L or I, and wherein $X_{14}$ is selected from the group comprising amino acids with an $NH_2$ group such as K, R, N, or Q, or amino acids with non-polar side chains such as A, V, L or I, and wherein the peptide comprises at least $X_7$-R-W-H-$X_{11}$ of SEQ ID NO:8, wherein $X_7$ is selected from the group comprising amino acids with an $NH_2$ group such as K, R, N, or Q, or amino acids with non-polar side chains such as A, V, L or I and wherein $X_{11}$ is selected from the group comprising amino acids with negatively charged side chains such as E or D, or amino acids with non-polar side chains such as A, V, L or I, or a peptidomimetic thereof.

Such breast cancers may include breast cancer forms, that are dependent on EGF-based ErbB activation for their tumorgenicity, that do not show an increased expression or activation of TGFα, and/or that are resistant to treatment with Trastuzumab or Pertuzumab and which show increased expression of Met. In one embodiment, the invention considers to inhibit formation of metastases in such patients. In another embodiment, these breast cancer types are metastasizing, i.e. metastases have already formed, breast cancers, which may be classifiable as Stage IV according to the TNM anatomic/prognostic group system of the cancer staging system of the American Joint Committee on Cancer. For such metastasizing cancers, the compounds of the invention may lead to a regression of the already formed metastases. Preferably all these breast cancer types show expression of CD44v6.

Even though the pentapeptides or any longer peptide derived from the 14 mer as described hereinafter should be effective not only in preventing metastasis but actually removing already formed metastases in breast cancers as described herein, a preferred embodiment of the present invention refers to the pentapeptide sequences described hereinafter, with a particular preferred embodiment focusing on the amino acid sequence N-R-W-H-E (SEQ ID NO:2). Breast cancers, which can be treated with such a compound, may include breast cancer forms, that are dependent on EGF-based ErbB activation for their tumorgenicity, that do not show an increased expression or activation of TGFα, and/or that are resistant to treatment with Trastuzumab or Pertuzumab and which show increased expression of Met. In one embodiment, the invention considers to inhibit formation of metastases in such patients. In another embodiment, these breast cancer types are metastasizing, i.e. metastases have already formed, breast cancers, which may be classifiable as Stage IV according to the TNM anatomic/prognostic group system of the cancer staging system of the American Joint Committee on Cancer. For such metastasizing cancers, the compounds of the invention may lead to a regression of the already formed metastases. Preferably all these breast cancer types show expression of CD44v6.

A person skilled in the art will understand that any compound that provides for the same amino acids or at least the same overall configuration of the peptide as peptides described herein such as the pentapeptide of SEQ ID NO:1 or SEQ ID NO:2 will also be efficient in not only preventing formation of metastasis, but also removing already formed metastases in breast cancers as described herein.

The invention therefore in some embodiments contemplates the use of peptidomimetics of any of the peptides described hereinafter particularly peptidomimetics of SEQ ID NO:1, SEQ ID NO:2, SEQ ID NO:3 or SEQ ID NO: 4 or 5. These peptidomimetics will preferably have the same amino acids but an altered backbone, which provides for the same overall configuration of the peptidomimetic as does the peptide itself, but which is e.g. more resistant to protease cleavage. Preferred peptidomimetics are e.g. isosteric peptoids, which comprise poly-N-substituted glycines in the peptide bonds of the backbone.

The present invention also considers further modified forms of the peptides and peptidomimetics described herein.

Such modified peptides or peptidomimetics may comprise e.g. chemically or enzymatically attached modifications that render the peptides more stable, e.g. against protease degradation, that allow to provide the peptides or peptidomimetics as pharmaceutically acceptable salts, or which e.g. improve the biological properties of the peptides or peptidomimetics such as half-life. Such preferred modified forms of such peptides or peptidomimetics refer to pegylated, hesylated, pasylated, myristoylated, glycosylated, and/or cyclic forms of these peptides and peptidomimetics, and in particular peptides of SEQ ID NO:1, SEQ ID NO:2, SEQ ID NO:3, SEQ ID NO:4 and SEQ ID NO:5 or peptidomimetics of these sequences.

Such modified peptides or peptidomimetics are generally referred to, in the context of the present invention, as compounds or peptide compounds. These compounds or peptide compounds may be formulated for oral administration, e.g. by inhalation, for nasal administration, or administration by injection such as subcutaneous administration.

In one embodiment the present invention also relates to pharmaceutical compositions for use in treating breast cancers. Such breast cancers may include breast cancer forms, that are dependent on EGF-based ErbB activation for their tumorgenicity, that do not show an increased expression or activation of TGFα, and/or that are resistant to treatment with Trastuzumab or Pertuzumab and which show increased expression of Met. In one embodiment, the invention considers to inhibit formation of metastases in such patients. In another embodiment, these breast cancer types are metastasizing, i.e. metastases have already formed, breast cancers, which may be classifiable as Stage IV according to the TNM anatomic/prognostic group system of the cancer staging system of the American Joint Committee on Cancer. For such metastasizing cancers, the compounds of the invention may lead to a regression of the already formed metastases. Preferably all these breast cancer types show expression of CD44v6. These pharmaceutical compositions may comprise pharmaceutically acceptable excipients and may be formulated for oral administration such as by inhalation, nasal administration or administration by injection.

The present invention also refers to the use of such peptides, peptidomimetics thereof, or modified peptides and peptidomimetics in the manufacture of a medicament for use in treating breast cancers. Such breast cancers may include breast cancer forms, that are dependent on EGF-based ErbB activation for their tumorgenicity, that do not show an increased expression or activation of TGFα, and/or that are resistant to treatment with Trastuzumab or Pertuzumab and which show increased expression of Met. In one embodiment, the invention considers to inhibit formation of metastases in such patients. In another embodiment, these breast cancer types are metastasizing, i.e. metastases have already formed, breast cancers, which may be classifiable as Stage IV according to the TNM anatomic/prognostic group system of the cancer staging system of the American Joint Committee on Cancer. For such metastasizing cancers, the compounds of the invention may lead to a regression of the already formed metastases. Preferably all these breast cancer types show expression of CD44v6.

Further, the invention relates to Methods of treating breast cancers in a human being by administering the peptides, peptidomimetics thereof or modified forms thereof, i.e. the compounds in accordance with the present invention, or pharmaceutical compositions comprising compounds in accordance with the present invention to a human being in need thereof. Such breast cancers may include breast cancer forms, that are dependent on EGF-based ErbB activation for their tumorgenicity, that do not show an increased expression or activation of TGFα, and/or that are resistant to treatment with Trastuzumab or Pertuzumab and which show increased expression of Met. In one embodiment, the invention considers to inhibit formation of metastases in such patients. In another embodiment, these breast cancer types are metastasizing, i.e. metastases have already formed, breast cancers, which may be classifiable as Stage IV according to the TNM anatomic/prognostic group system of the cancer staging system of the American Joint Committee on Cancer. For such metastasizing cancers, the compounds of the invention may lead to a regression of the already formed metastases. Preferably all these breast cancer types show expression of CD44v6.

The compounds in accordance with the present invention, i.e. the peptides, peptidomimetics thereof or modified forms thereof, the pharmaceutical compositions of the present invention, and the Methods in accordance with the present invention are considered for treating breast cancers. Such breast cancers may include breast cancer forms, that are dependent on EGF-based ErbB activation for their tumorgenicity, that do not show an increased expression or activation of TGFα, and/or that are resistant to treatment with Trastuzumab or Pertuzumab and which show increased expression of Met. Preferably all these breast cancer types show expression of CD44v6. These cancer types can be identified and distinguished from other cancer types, such as estrogen-receptor dependent breast cancer, which is not treatable by the compounds in accordance with the invention, through common diagnostic approaches such as taking biopsies, expression profiling etc. A particularly useful categorization is provided by the TNM Anatomic Stage/Prognostic Group System of the Cancer Staging Manual of the American Joint Committee on Cancer ($7^{th}$ edition, 2010, Springer). It is preferred for the purpose of the invention that breast cancers are categorized according to these principles and supplemented where necessary, e.g. by expression profiling for EGF, TGFα and ErbB1 and 2.

The compounds in accordance with the present invention, i.e. the peptides, peptidomimetics thereof or modified forms thereof, the pharmaceutical compositions of the present invention, and the Methods in accordance with the present invention are considered for treating breast cancers where metastases have already formed and may have even spread across the body. These cancers are also designated as metastasizing cancers and include metastasizing forms of breast cancer forms, that are dependent on EGF-based ErbB activation for their tumorgenicity, that do not show an increased expression or activation of TGFα, and/or that are resistant to treatment with Trastuzumab or Pertuzumab and which show increased expression of Met. Preferably all these breast cancer types show expression of CD44v6.

Such metastasizing breast cancer forms can be identified according to the TNM Anatomic Stage/Prognostic Group System of the Cancer Staging Manual of the American Joint Committee on Cancer ($7^{th}$ edition, 2010, Springer). Metastasizing breast cancers in accordance with the invention will typically be classified as a Stage IV cancer according to the TNM Anatomic Stage/Prognostic Group System, particularly if M is set as 1. The Cancer Staging Manual of the American Joint Committee on Cancer ($7^{th}$ edition, 2010, Springer) describes the TNM Anatomic Stage/Prognostic Group System and under which conditions a cancer is considered to be of e.g. Stage I, II, III and IV for the various cancers mentioned herein and is thus included by reference.

It is to be understood that for all aspects and embodiments of the present invention, i.e. the compounds, pharmaceutical compositions and Methods as described hereinafter, it is always preferred to use the pentapeptides as described herein, such as those of SEQ ID NO:1, SEQ ID NO:2; SEQ ID NO:3, SEQ ID NO:4 and SEQ ID NO:5 and in particular of SEQ ID NO:2 for treating breast cancers in a human being, and in particular for treating breast cancers as they are described above, which are classifiable as Stage IV according to the TNM Anatomic Stage/Prognostic Group System of the Cancer Staging Manual of the American Joint Committee on Cancer (7th edition, 2010, Springer).

FIGURE LEGENDS

The patent or application file contains at least one drawing executed in color. Copies of this patent or patent application publication with color drawing(s) will be provided by the Office upon request and payment of the necessary fee.

FIG. 1: The binding specificity of the ErbB ligands. The ErbB ligands can bind to 11 different ligands by forming homo- and heterodimers (Based on Olayioye et al., (2000), see reference)

FIG. 2: EGF-dependent induction of the ErbB receptors can be blocked by a CD44v6 specific peptide. Serum-starved HT29 cells were pre-incubated for 5 min with 100 ng/ml of a CD44v6-specific peptide or a control peptide. Afterwards the cells were induced with 20 ng/ml of EGF and lysed. The cell lysates were resolved by SDS-PAGE. Western-blotting was used to detect EGF- and HGF-induced Erk-kinase phosphorylation.

FIG. 3: In contrast to EGF and ER, induction of the ErbB-receptors via TGFα, BC, Her, HB-EGF or AR is completely independent of CD44v6. Serum-starved HT29 cells were pre-incubated for 5 min with 100 ng/ml of a CD44v6-specific peptide or a control peptide. Afterwards the cells were induced with 20 ng/ml of various ErbB ligands as indicated. The cell lysates were resolved by SDS-PAGE. Western-blotting was used to detect ErbB ligands-induced Erk-kinase phosphorylation.

FIG. 4: EGF- and ER-dependent induction of the ErbB receptors can be abolished by abrogating the expression of CD44v6 by means of siRNA. HeLa cells (upper part) and HT29 cells (lower part) were transfected with CD44v6-specific siRNA or control siRNA as indicated. After transfection, the cells were serum starved for 24 h. They were then induced with 5 ng/ml of EGF or ER as indicated. The cell lysates were resolved by SDS-PAGE. Western-blotting was used to detect EGF and ER and -induced ErbB1 and Erk phosphorylation.

FIG. 5: Induction of the ErbB-receptors via TGFα is independent of CD44. HT29 cells were transfected with CD44v6-specific siRNA or control siRNA as indicated. After transfection, the cells were starved for 24 h. They were then induced with 5 ng/ml of EGF or TGFα as indicated. The cell lysates were resolved by SDS-PAGE. Western-blotting was used to detect EGF and ER and -induced ErbB1 and Erk phosphorylation.

FIG. 6: Induction of the ErbB-receptors via HB-EGF but not AR is dependent on heparin-sulphation. Serum-starved HT29 cells were pre-treated with heparinase at a concentration of 6 U/ml for 3 h and then induced with 5 ng/ml of HB-EGF or AR (HGF was used as a control). The cell lysates were resolved by SDS-PAGE. Western-blotting was used to detect the ErbB-ligands-induced Erk phosphorylation.

FIG. 7: Induction of the ErbB-receptors via HB-EGF is dependent on CD44v3. HT29 cells were transfected with CD44v3-specific siRNA or control siRNA as indicated. After transfection, the cells were starved for 24 h. They were then induced with 5 ng/ml of EGF or HB-EGF as indicated. The cell lysates were resolved by SDS-PAGE. Western-blotting was used to detect EGF and HB-EGF and -induced ErbB1 and Erk phosphorylation.

FIG. 8: EGF can induce ErbB1 homodimers only in cells expressing CD44v6 whereas TGFα can do so independently of CD44v6 expression. AS cells and the ASs6 cells were transfected with the ErbB1 expression vector receptor or a control vector by means of the retroviral ecopack 2-293 system as described in Material and Methods. Afterwards the transfected cells were starved and induced with 5 ng/ml of EGF or TGFα. The cell lysates were resolved by SDS-PAGE. Western-blotting was used to detect EGF- and TGFα and induced ErbB1 and Erk phosphorylation.

FIG. 9: ER can only induce ErbB1 homodimers in cells expressing CD44v6. AS and ASs6 cells were transfected with the ErbB1 expression vector receptor or a control vector by means of the retroviral ecopack 2-293 system as described in Material and Methods. Afterwards the transfected cells were starved and induced with 5 ng/ml of ER or TGFα. The cell lysates were resolved by SDS-PAGE. Western-blotting was used to detect ER- and TGFα and -induced ErbB1 and Erk phosphorylation.

FIG. 10: HB-EGF can induce ErbB1 homodimers only in cells expressing CD44v3. Ass6 cells and ASv1-v10 cells were transfected with the ErbB1 expression vector receptor or a control vector by means of the retroviral ecopack 2-293 system as described in Material and Methods. Afterwards the transfected cells were starved and induced with 5 ng/ml of EGF or HB-EGF. The cell lysates were resolved by SDS-PAGE. Western-blotting was used to detect EGF- and HB-EGF and induced ErbB1 and Erk phosphorylation.

FIG. 11: Scheme of the primer pairs used for the detection of CD44 mRNA by PCR.

FIG. 12: Detection of CD44 by PCR. MCF7 (upper part) as well as MCF10A cells (lower part) predominantly express CD44v2-v10 in one long isoform. The expression of CD44 transcripts was tested by run-off PCR. The total RNA of the target cells was isolated, transcribed into cDNA and the expression of CD44 variant transcripts was detected by PCR via different variant-exon specific forward primers and one common backward primer specific for a region in the constant part of CD44.

FIG. 13: CD44v6 acts as a co-receptor for EGF-dependent ErbB induction in breast cancer cells. Serum-starved MCF7 (upper part) and MCF10 (lower part) cells were pre-incubated for 5 min with 100 ng/ml of a CD44v6-specific peptide or a control peptide. Afterwards the cells were induced with 20 ng/ml of EGF. The cell lysates were resolved by SDS-PAGE. Western-blotting was used to detect EGF-induced Erk-kinase phosphorylation.

FIG. 14: CD44v6 acts as a co-receptor for EGF-dependent ErbB induction in breast cancer cells. Serum-starved MCF7 cells were treated with CD44v6-specific siRNA or control siRNA respectively. After transfection, the cells were starved for 24 h. They were then induced with 5 ng/ml of EGF. The cell lysates were resolved by SDS-PAGE. Western-blotting was used to detect EGF-induced Erk phosphorylation.

FIG. 15: ErbB1 and CD44v6 are found in an inducible complex. Serum-starved MCF10 cells were either induced with 5 ng/ml of EGF or left untreated. Afterwards an ErbB1-Immunoprecipitation (or CD44v6-Immunoprecipitation as a control) was performed. The cell lysates were resolved by SDS-PAGE. A Western-blot was performed to detect ErbB1 and CD44v6.

FIG. 16: The co-receptor function of CD44v6 for Met is required for tumor metastasis. A) BSp73AS and its transfectants were induced with HGF where indicated and the activation of Met and ERK was determined as described in Materials and Methods. The numbers indicate the fold induction as calculated by the computer program ImageJ. All experiments were performed at least 3 times and gave similar results. B) The cells used in A were subcutaneously injected into the right posterior flank of syngeneic rats (Materials and Methods). Four weeks later the lymph nodes and lungs were prepared for immunohistochemical analysis. The represented lymph nodes are the auxiliary lymph nodes. Two pictures of the lungs are shown, the arrows indicate metastases. C) Immunohistochemical analysis of paraffin sections of ASs6 tumors infected with lentivirus expressing ctrl-shRNA or Met-shRNA. Slices were stained with anti-GFP antibody to monitor shRNA-transduced areas or with a phospho-Met antibody. Magnification 20×.

FIG. 17: A CD44v6 specific peptide blocks metastatic spreading of tumor cells. A) BSp73ASs6 cells were induced with HGF in the presence of the CD44v6-specific rat peptide, a CD44v6 specific antibody or a control peptide (mouse) as indicated. The activation of Met and Erk was determined using phospho-specific antibodies. The numbers refer to the fold induction. B) BSp73ASs6 cells were injected subcutaneously into the right posterior flank of BD10 rats. After one week of tumor growth the animals were treated with the CD44v6 peptide (i.t. or i.v.), the control peptide, the CD44v6 antibody or PBS (Materials and Methods). Axillary lymph nodes (left side) and lungs (right side) were analyzed for metastases as described in FIG. 1. C) Sections of lungs of animals treated either with the CD44v6 peptide or with the control peptide were stained with H&E and PAS. H&E—hematoxylin and eosin; PAS—Periodic acid-Schiff reaction. Magnification 1.5×. D) Growth curve of BSp73ASs6 tumors in animals upon treatment for 28 days as indicated. The mean tumor volume of rats treated with either PBS, CD44v6 antibody, CD44v6 peptide or control peptide (mouse) was measured weekly after the start of the treatment and continued for 28 days using a caliper.

FIG. 18: Specific binding of the CD44v6 peptide to primary tumors and metastases in vivo. A) Left side: BSp73ASs6 cells were fixed and stained either with the DY681 labeled CD44v6 rat or the mouse peptide (control) for one hour. Images were taken using a laser scanning confocal microscope (Leica TCS2 SP2) with a 20× objective. Right side: BSp73ASs6 cells were induced with HGF in the presence of the DY681 rat v6 peptide respectively mouse peptide and the activation of Erk was determined. The numbers indicate fold induction. B) Rats bearing a subcutaneous tumor of BSp73ASs6 cells (grown for three weeks) were injected i.v with 200 µg of DY681 rat v6 peptide or DY681 mouse v6 peptide (control) and analyzed by NIRF imaging using Optix MX2 (ART, Montreal, Canada). Fluorescence intensities are displayed in NC (Normalized Correlation). Series of fluorescent data sets obtained at various time points after injection of the indicated peptide show fluorescent signals after 24 and 48 hours indicating binding of the rat v6 peptide but not the mouse v6 peptide in the range of two days to the tumor. C) Ex vivo scans of tumors and lungs from rats injected with DY681 rat v6 peptide showed specific fluorescent signals not only over the tumor area but also in specific areas of the lung indicating binding of the rat peptide to metastases.

FIG. 19: A CD44v6 peptide prevents metastasis of human tumor cells in an orthotopic model of pancreatic cancer. A: L3.6pl cells were treated with the human v6 peptide or the rat v6 peptide as control prior to induction with 10 ng/ml HGF. Activation of Erk was determined in western blot. The numbers refer to the fold induction. B: L3.6pl cells were injected orthotopically into the head of the pancreas of male nude mice (Materials and Methods). 7 days later the animals were injected with the human CD44v6 peptide or control (rat) peptide (20 µg each). The peptide injection was repeated 3 times per week. Animals were killed 23 days after the first peptide treatment. Tumors were isolated and stained for CD44v6 expression (BIWA) or secondary antibody as control. Nuclei were stained with hematoxylin. C: Immunofluorescence staining of L3.6pl tumors from the v6 peptide or control peptide treated animals using the phospho-Met and Met antibodies. Nuclei are stained with DAPI. D top: Tumor volume of animals treated with either v6 or control peptide was determined at the end of the experiment using the formula volume=(width)2×length/2. Bars represent average tumor volume at the end of the experiment. D Bottom: Each group of animals treated with one of the peptides consisted of 15 animals. Bars show the percentage of animals bearing metastases. E: Staining of L3.6pl tumors treated with control or v6 peptide with a CD31-specific antibody. The magnification is 50×. The graphs show the average vessel numbers respectively average vessel size calculated from five independent tumors. F: Human VEGF levels produced by L3.6pl cells in presence and absence of the v6 peptide (200 ng/ml in the culture medium). Bars reflect average VEGF levels from triplicates obtained in 3 independent experiments. G: Left side:Livers of v6 peptide or control peptide treated animals were examined for macroscopic metastases. Right side: Bars show the average number of metastases. Each group of animals treated with one of the peptides consisted of 15 animals. In all graphs the significance was calculated using Student's t test: ***p<0.001.

FIG. 20: Specific accumulation of the CD44v6 peptide in primary tumors and metastases of the human pancreatic cancer model. A: Left side:L3.6pl cells were stained with either the DY681 labeled CD44v6 human or rat peptide. Images were taken with the laser scanning confocal microscope (Leica TCS2 SP2). Right side: L3.6pl cells were induced with HGF in the presence of the DY681 human v6 peptide respectively rat v6 peptide and the activation of Erk was determined. The numbers refer to the fold induction. B: L3.6pl tumors were orthotopically induced for 3 weeks as described in FIG. 4 followed by one intravenous injection of DY681 human v6 peptide or DY681 rat v6 peptide, (each 20 µg). Binding of the peptide was analyzed 24 h after injection in anesthetized mice using the Pearl® Impulse Small Animal Imaging System (Li-Cor). Tumor free and tumor bearing animals that received no peptide treatment were used as control. C: Primary tumors, livers and spleens were excised from the animals shown in B and fluorescence of the labeled peptides was monitored ex-vivo. The scales at the side indicate the synchronized signal intensity.

FIG. 21: Reversion of pre-existing metastases by the CD44v6 peptides. A: Schematic representation of the experimental procedure. BSp73ASs6 cells or L3.6pl cells were injected in rats respectively nude mice. During the following 3 weeks, the tumors developed and metastases were detected after 3 weeks of time. In the groups treated with the v6 peptide or the control peptide (200 µg in rats, 20 µg in nude mice), the treatment started after three weeks. After 21 additional days the animals were sacrificed and analyzed for lung respectively liver metastases. B: Lungs of rats bearing a BSp73ASs6 subcutaneous tumor and treated with the v6 peptide (rat) or the control peptide (mouse) are shown (upper part). Bottom left: The quantification represents the average number of metastases. The number of animals used in each group is given in Table 3. Bottom right: A graphic evaluation of the number of animals bearing metastases is presented. C: Livers from mice with L3.6pl pancreatic tumors and treated with the v6 peptide (human) or the control peptide (rat) are shown (upper part). Bottom left: A graph evaluating the number of liver metastases in control peptide treated animals and CD44v6 peptide treated animals is shown. Bottom right: A graphic evaluation of the number of animals bearing metastases is presented.

FIG. 22: The CD44v6 peptide induces apoptosis in already established metastases. Animals bearing lung metastases three weeks after tumor cell injection received an injection of CD44v6 peptide or control peptide every second day. At the indicated days one animal of each group was sacrificed. Apoptosis in lung metastasis was monitored on paraffin sections using an antibody against cleaved Caspase-3 and cleaved Caspase-8 (Materials and Methods). The area of the metastasis is marked (M). The magnification is 4.5×. The experiment was performed 2 times with similar outcome.

FIG. 23: depicts Tables 1 (upper part), 2 (middle part) and 3 (lower part).

FIG. 24: depicts effects of pegylated rat CD44v6 peptides on activation of ERK in rat pancreatic cells.

FIG. 25: depicts effects of pegylated rat CD44v6 peptides on activation of ERK and Met in rat pancreatic cells.

FIG. 26: depicts effects of pegylated rat CD44v6 peptides on HGF induced clustering in colon cancer cells.

FIG. 27: Treatment with the v6 14mer reduces growth of the primary tumor and macroscopic metastases formation in the lung. 1×106 murine 4T1 cells per mouse were diluted in 50 µl RPMI plus 50 µl Matrigel and injected into the 6th mammary fat pad of 10 female BALB/c mice. One week after the injection, the mice were either injected intraperitoneally with 20 µg of the murine v6 14mer dissolved in 100 µl PBS or with 20 µg of control peptide (rat v6 14mer) dissolved in 100 µl PBS. The injection was performed 3 times per week for two weeks. After 2 weeks the mice were sacrificed and the primary tumors and the lungs were extracted. A: Overall reduction of the tumor volume in the v6 peptide treated group B: Immunofluorescent staining for the endothelial marker CD34 to monitor vascularization of the primary tumor. Graphic representation of the reduction of the total vessel area. C: The v6 peptides led to a reduction in macroscopic lung metastasis. The black arrows mark examples for metastases. The scale bar corresponds to a size of 1 cm. Statistical evaluation of the average number of lung metastases. Significance was calculated using Student's t test: $p^*<0.01$; $^{**}p<0.005$. Each group consisted of 5 animals.

FIG. 28: A: Activation of Met and signal transduction induced by HGF depends on CD44v6 in L3.6pl cells. L3.6pl cells were treated with the human v6 peptide (human v6 14mer) or the rat v6 peptide as control prior to induction with 10 ng/ml HGF. Activation of Met and ERK was determined in western blot. The numbers refer to the fold induction. The experiment was repeated at least 5 times. B: Activation of c-Met and signal transduction induced by HGF depends on CD44v6 HeLa cells. Starved HeLa cells respectively HT29 cells were incubated with the v6 peptide (human v6 14mer) or a control peptide for 10 minutes at 37° C. and then induced with 25 ng/ml of HGF for the indicated time points. Cells were then either lysed and the lysates were subjected to Western Blot analysis for phospho-Met and Met. C: Activation of c-Met and signal transduction induced by HGF depends on CD44v6 in HT29 cells. HGF-induced c-Met and Erk phosphorylation in HT29 was determined as described above using phospho-specific antibodies. Where indicated the cells were pretreated with the CD44v6 peptide (human v6 14mer) or the control peptide (see Materials and Methods in Example 3). The loading controls were developed with c-Met respectively tubulin antibodies.

FIG. 29: In contrast to EGF and ER, induction of the ErbB-receptors via TGF-α, BC, Her, HB-EGF or AR is completely independent of CD44v6. Serum-starved HT29 cells were pre-incubated for 5 min with 100 ng/ml of a CD44v6-specific peptide (human v6 14mer) or a control peptide. Afterwards the cells were induced with 20 ng/ml of various ErbB ligands as indicated. The cell lysates were resolved by SDS-PAGE. Western-blotting was used to detect ErbB ligands-induced Erk-kinase phopshorylation.

FIG. 30: EGF-dependent induction of the ErbB receptors can be blocked by a CD44v6 specific peptide in HT29 cells. Serum-starved HT29 cells were pre-incubated for 5 min with 100 ng/ml of CD44v6-specific peptide (pep1=14mer, pep2=5mer) or a control peptide. Afterwards the cells were induced with 20 ng/ml of EGF or TGFα and lysed. The cell lysates were resolved by SDS-PAGE. Western-blotting was used to detect EGF and TGFα induced Erk-kinase phopshorylation.

DETAILED DESCRIPTION OF THE INVENTION

Before the invention is described in detail with respect to some of its preferred embodiments, the following general definitions are provided.

The present invention as illustratively described in the following may suitably be practiced in the absence of any element or elements, limitation or limitations, not specifically disclosed herein.

The present invention will be described with respect to particular embodiments and with reference to certain figures but the invention is not limited thereto but only by the claims.

Where the term "comprising" is used in the present description and claims, it does not exclude other elements. For the purposes of the present invention, the term "consisting of" is considered to be a preferred embodiment of the term "comprising of". If hereinafter a group is defined to comprise at least a certain number of embodiments, this is also to be understood to disclose a group, which preferably consists only of these embodiments.

For the purposes of the present invention, the term "obtained" is considered to be a preferred embodiment of the term "obtainable". If hereinafter e.g. an antibody is defined to be obtainable from a specific source, this is also to be understood to disclose an antibody, which is obtained from this source.

Where an indefinite or definite article is used when referring to a singular noun, e.g. "a", "an" or "the", this includes a plural of that noun unless something else is specifically stated. The terms "about" or "approximately" in the context of the present invention denote an interval of accuracy that the person skilled in the art will understand to still ensure the technical effect of the feature in question. The term typically indicates deviation from the indicated numerical value of ±20%, preferably ±15%, more preferably ±10%, and even more preferably ±5%.

Furthermore, the terms "first", "second", "third" or "(a)", "(b)", "(c)", "(d)" or "(i)", "(ii)", "(iii)", "(iv)" etc. and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

In case the terms "first", "second", "third" or "(a)", "(b)", "(c)", "(d)" or "(i)", "(ii)", "(iii)", "(iv)" etc. relate to steps of a method or use or assay there is no time or time interval coherence between the steps unless indicated otherwise, i.e. the steps may be carried out simultaneously or there may be time intervals of seconds, minutes, hours, days, weeks, months or even years between such steps, unless otherwise indicated in the application as set forth herein above or below.

Technical terms are used by their common sense. If a specific meaning is conveyed to certain terms, definitions of terms will be given in the following in the context of which the terms are used.

As mentioned above, the present invention is concerned with peptides or peptide compounds for use in treating metastasizing cancer in a human being.

The present invention is based to some extent on the experimental findings described hereinafter that a peptide of amino acid sequence N-R-W-H-E (SEQ ID NO: 2) is not only capable of inhibiting metastasis in human pancreatic cancer cells but can also eliminate already established metastases in an orthotropic animal model of human pancreatic cancer. It thus seems reasonable to assume that the same efficacy can be observed in different metastasizing cancers, particularly where these cancers show expression of CD44v6. It was moreover shown that upon mutating N to A and E to A, a peptide of amino acid sequence A-R-W-H-A (SEQ ID NO:3) is capable of abrogating Met activation (see Matzke et al., *Cancer Res.* (2005), 65 (14), 6105-6110). Given that the effects on Met activation by N-R-W-H-E (SEQ ID NO:2) are maintained despite the non-conservative amino acids substitutions of K to A and F to A (Matzke et al., vide supra), it seems reasonable to assume that a peptide of amino acid sequence $X_1$-R-W-H-$X_5$ (SEQ ID NO:1), wherein $X_1$ is selected from the group comprising A, C, D, E, F, G, H, I, K, L, M, N, P, Q, R, S, T, V, W, or Y and wherein $X_5$ is selected from the group comprising A, C, D, E, F, G, H, I, K, L, M, N, P, Q, R, S, T, V, W, or Y can be used not only for treatment of pancreatic cancer, but also for metastasizing cancers in general. In view of the data presented herein on the ligand-dependent activation of ErbB1 and ErbB2 through CD44v6, this should particularly apply to breast cancer, and specific forms thereof. Such specific breast cancers may include breast cancer forms, that are dependent on EGF-based ErbB activation for their tumorgenicity, that do not show an increased expression or activation of TGFα, and/or that are resistant to treatment with Trastuzumab or Pertuzumab and which show increased expression of Met. In one embodiment, the invention considers to inhibit formation of metastases in such patients. In another embodiment, these breast cancer types are metastasizing, i.e. metastases have already formed, breast cancers, which may be classifiable as Stage IV according to the TNM anatomic/prognostic group system of the cancer staging system of the American Joint Committee on Cancer. For such metastasizing cancers, the compounds of the invention may lead to a regression of the already formed metastases. Preferably all these breast cancer types show expression of CD44v6.

The present invention thus in one embodiment relates to a compound for use in treating breast cancer, and preferable the specific types of breast cancer as mentioned herein, in a human being, wherein said compound comprises a peptide comprising at least the amino acid sequence $X_1$-R-W-H-$X_5$ (SEQ ID NO: 1), wherein $X_1$ is selected from the group comprising A, C, D, E, F, G, H, I, K, L, M, N, P, Q, R, S, T, V, W, or Y and wherein $X_5$ is selected from the group comprising A, C, D, E, F, G, H, I, K, L, M, N, P, Q, R, S, T, V, W, or Y or a peptidomimetic thereof.

Preferably, the present invention in one embodiment relates to a compound for use in treating breast cancer, and preferably the specific types of breast cancer as mentioned herein, in a human being, wherein said compound comprises a peptide comprising at least the amino acid sequence $X_1$-R-W-H-$X_5$ (SEQ ID NO: 4), wherein $X_1$ is selected from the group comprising amino acids with an $NH_2$ group such as K, R, N, or Q, or amino acids with non-polar side chains such as A, V, L or I and wherein $X_5$ is selected from the group comprising amino acids with negatively charged side chains such as E or D, or amino acids with non-polar side chains such as A, V, L or I or a peptidomimetic thereof. An example is a peptide of amino acid sequence A-R-W-H-A (SEQ ID NO:3) or a peptidomimetic thereof.

Even more preferably, the present invention in one embodiment relates to a compound for use in treating breast cancer in a human being, and preferably the specific types of breast cancer as mentioned herein, wherein said compound comprises a peptide comprising at least the amino acid sequence $X_1$-R-W-H-$X_5$ (SEQ ID NO:5), wherein $X_1$ is selected from the group comprising K, R, N, or Q and wherein $X_5$ is selected from the group comprising E or D. As an example of one of the most preferred embodiments the peptide may comprise and preferably consist of amino acid sequence N-R-W-H-E (SEQ ID NO:2).

Preferred specific types of breast cancers may include breast cancer forms, that are dependent on EGF-based ErbB activation for their tumorgenicity, that do not show an increased expression or activation of TGFα, and/or that are resistant to treatment with Trastuzumab or Pertuzumab and which show increased expression of Met. In one embodiment, the invention considers to inhibit formation of metastases in such patients. In another embodiment, these breast cancer types are metastasizing, i.e. metastases have already formed, breast cancers, which may be classifiable as Stage IV according to the TNM anatomic/prognostic group system of the cancer staging system of the American Joint Committee on Cancer. For such metastasizing cancers, the compounds of the invention may lead to a regression of the already formed metastases. Preferably all these breast cancer types show expression of CD44v6.

The term "peptide" as used herein refers to any compound comprising at least the above mentioned amino acids five and a maximum of fourteen amino acids.

If peptides in accordance with the invention have more than the above-mentioned five amino acids, these amino acids may e.g. be those found in a peptide of amino acid sequence K-E-Q-W-F-G-N-R-W-H-E-G-Y-R (SEQ ID NO: 6) or variations thereof. It is noted that amino acids 7 to 11 of SEQ ID NO: 6 correspond to SEQ ID NO: 2. As for a peptide of SEQ ID NO: 2, it has been found in a linker screen analysis with alanine substitutions that amino acids 1, 2, 3, 4, 5, 6, 12, 13, or 14 can be substituted by alanine without having detrimental effects on Met activation. Such peptides may thus be any peptide comprising amino acids 6 to 12, 5 to 13, 4 to 14, etc. of $X_1$-$X_2$-$X_3$-$X_4$-$X_5$-$X_6$-$X_7$-R-W-H-$X_{11}$-$X_{12}$-$X_{13}$-$X_{14}$ (SEQ ID NO:7), wherein $X_1$ is selected from the group comprising A, C, D, E, F, G, H, I, K, L, M, N, P, Q, R, S, T, V, W, or Y, wherein $X_2$ is selected from the group comprising A, C, D, E, F, G, H, I, K, L, M, N, P, Q, R, S, T, V, W, or Y, $X_3$ is selected from the group comprising A, C, D, E, F, G, H, I, K, L, M, N, P, Q, R, S, T, V, W, or Y, $X_4$ is selected from the group comprising A, C, D, E, F, G, H, I, K, L, M, N, P, Q, R, S, T, V, W, or Y, $X_5$ is selected from the group comprising A, C, D, E, F, G, H, I, K, L, M, N, P, Q, R, S, T, V, W, or Y, $X_6$ is selected from the group comprising A, C, D, E, F, G, H, I, K, L, M, N, P, Q, R, S, T, V, W, or Y, $X_7$ is selected from the group comprising A, C, D, E, F, G, H, I, K, L, M, N, P, Q, R, S, T, V, W, or Y, $X_{11}$ is selected from the group comprising A, C, D, E, F, G, H, I, K, L, M, N, P, Q, R, S, T, V, W, or Y, $X_{12}$ is selected from the group comprising A, C, D, E, F, G, H, I, K, L, M, N, P, Q, R, S, T, V, W, or Y, $X_{13}$ is selected from the group comprising A, C, D, E, F, G, H, I, K, L, M, N, P, Q, R, S, T, V, W, or Y and wherein $X_{14}$ is selected from the group comprising A, C, D, E, F, G, H, I, K, L, M, N, P, Q, R, S, T, V, W, or Y. Preferably the selection is made according to the principles laid out above. Thus, $X_1$ may either be an amino acid similar to K or it may be an amino acid with a non-polar side chain such as A, V, L, or I. Similar considerations apply to $X_2$, $X_3$, $X_4$, $X_5$, $X_6$, $X_7$, $X_{11}$, $X_{12}$, $X_{13}$ or $X_{14}$. In one preferred embodiment such longer peptide comprise amino acids 6 to 12, 5 to 13, 4 to 14, etc. of $X_1$-$X_2$-$X_3$-$X_4$-$X_5$-$X_6$-$X_7$-R-W-H-$X_{11}$-$X_{12}$-$X_{13}$-$X_{14}$ (SEQ ID NO: 8), wherein $X_1$ is selected from the group comprising amino acids with an $NH_2$ group such as K, R, N, or Q, or amino acids with non-polar side chains such as A, V, L or I, wherein $X_2$ is selected from the group comprising amino acids with negatively charged side chains such as E or D, or amino acids with non-polar side chains such as A, V, L or I, wherein $X_3$ is selected from the group comprising amino acids with an $NH_2$ group such as K, R, N, or Q, or amino acids with non-polar side chains such as A, V, L or I, wherein $X_4$ is selected from the group comprising amino acids with non-polar or non-charged side chains and aromatic rings structures such as F, W, or Y, or amino acids with non-polar side chains such as A, V, L or I, wherein $X_5$ is selected from the group comprising amino acids with non-polar or non-charged side chains and aromatic rings structures such as F, W, or Y, or amino acids with non-polar side chains such as A, V, L or I, wherein $X_6$ is selected from the group comprising G or amino acids with non-polar side chains such as A, V, L or I, wherein $X_7$ is selected from the group comprising amino acids with an $NH_2$ group such as K, R, N, or Q, or amino acids with non-polar side chains such as A, V, L or I, wherein $X_{11}$ is selected from the group comprising amino acids with negatively charged side chains such as E or D, or amino acids with non-polar side chains such as A, V, L or I, wherein $X_{12}$ is selected from the group comprising G or amino acids with non-polar side chains such as A, V, L or I, wherein $X_{13}$ is selected from the group comprising amino acids with non-polar or non-charged side chains and aromatic rings structures such F, W, or Y, or amino acids with non-polar side chains such as A, V, L or I, and wherein $X_{14}$ is selected from the group comprising amino acids with an $NH_2$ group such as K, R, N, or Q, or amino acids with non-polar side chains such as A, V, L or I. In an even more preferred embodiment such longer peptide comprise amino acids 6 to 12, 5 to 13, 4 to 14, etc. of $X_1$-$X_2$-$X_3$-$X_4$-$X_5$-$X_6$-$X_7$-R-W-H-$X_{11}$-$X_{12}$-$X_{13}$-$X_{14}$ (SEQ ID NO: 9), wherein $X_1$ is selected from the group comprising amino acids with an $NH_2$ group such as K, R, N, or Q, wherein $X_2$ is selected from the group comprising amino acids with negatively charged side chains such as E or D, wherein $X_3$ is selected from the group comprising amino acids with an $NH_2$ group such as K, R, N, or Q, wherein $X_4$ is selected from the group comprising amino acids with non-polar or non-charged side chains and aromatic rings structures such as F, W, or Y, wherein $X_5$ is selected from the group comprising amino acids with non-polar or non-charged side chains and aromatic rings structures such as F, W, or Y, wherein $X_6$ is selected from the group comprising G or amino acids with non-polar side chains such as A, V, L or I, wherein $X_7$ is selected from the group comprising amino acids with an $NH_2$ group such as K, R, N, or Q, $X_{11}$ is selected from the group comprising amino acids with negatively charged side chains such as E or D, wherein $X_{12}$ is selected from the group comprising G or amino acids with non-polar side chains such as A, V, L or I, wherein $X_{13}$ is selected from the group comprising amino acids with non-polar or non-charged side chains and aromatic rings structures such F, W, or Y, and wherein $X_{14}$ is selected from the group comprising amino acids with an $NH_2$ group such as K, R, N, or Q.

Peptides may be linear, branched and they may be cyclic, with or without branching. Cyclic, branched and branched cyclic peptides may result from post-translation natural processes or may be made by synthetic methods.

In some of the most preferred embodiments, peptides in accordance with the invention comprise and more preferably consist of five or 14 amino acids as mentioned above and include peptides of SEQ ID NO: 1, 2, 3, 4, 5 or 6 to 10. The most preferred embodiment of the present invention relates to a peptide of SEQ ID NO:2.

The term "compound comprising a peptide" refers to compounds which comprise a peptide e.g. in the form of a pharmaceutically acceptable salt. The term equally refer to peptides which have been e.g. chemically or enzymatically modified such that e.g. a peptide of SEQ ID NO:1, 2, 3, 4 or 5 comprises additional modifications as they are described hereinafter. Modified forms of a peptide of SEQ ID NO:2 are particularly preferred.

The term "compound comprising a peptide" and its grammatical variation such as "peptide compound" thus includes salts, preferably pharmaceutically acceptable salts of the peptides described herein. Salts encompassed within the term "pharmaceutically acceptable salts" refer to non-toxic salts of the peptide compounds of this invention. Representative salts and esters include the following: acetate, ascorbate, benzenesulfonate, benzoate, bicarbonate, bisulfate, bitartrate, borate, caamsylate, carbonate, citrate, dihydrochloride, Methanesulfonate, ethanesulfonate, p-toluenesulfonate, cyclohexylsulfamate, quinate, edetate, edisylate, estolate, esylate, fumarate, gluconate, glutamate, glycerophosphates, hydrobromide, hydrochloride, hydroxynaphthoate, lactate, lactobionate, laurate, malate, maleate, mandelate, mesylate, mucate, napsylate, nitrate, n-Methylglucamine, oleate, oxalate, palmoates, pamoate (embonate), palmitate, pantothenate, perchlorates, phosphate/diphosphate, polygalacturonate, salicylates, stearate, succinates, sulfate, sulfamate, subacetate, succinate, tannate, tartrate, tosylate, trifluoroacetate, and valerate. Other salts include Ca, Li, Mg, Na, and K salts; salts of amino acids such as lysine or arginine; guanidine, diethanolamine or choline; ammonium, substituted ammonium salts or aluminum salts. The salts are prepared by conventional Methods.

The peptide component of "compound comprising a peptide" may, however, in addition to the peptide sequence of any of SEQ ID NOs: 1 to 9 comprise amino acid sequences derived from other proteins. Therefore, the peptide compound of the invention includes heterologous fusion peptides consisting essentially of SEQ ID NOs: 1 to 9 fused to a heterologous amino acid sequence. The heterologous amino acid sequence may comprise or consist of 1, 2, 3, 4 or more amino acids. The heterologous amino acid sequence may for example comprise or consist of at least 5 or at least 10 or at least 20 heterologous amino acids. The heterologous amino acids may be fused to the N- and/or C-terminus of the CD44-derived sequences SEQ ID Nos.: 1 to 9 to provide other functionalities such as improved translocation across cellular membranes.

It is preferred that the peptide component of the invention is an isolated peptide. The term "isolated" means altered "by the hand of man" from the natural state. If an "isolated" composition or substance occurs in nature, it has been changed or removed from its original environment, or both. For example, a polynucleotide or a polypeptide naturally present in a living animal is not "isolated," but the same polynucleotide or polypeptide separated from the coexisting materials of its natural state is "isolated", as the term is employed herein.

It is also preferred that the peptide of the invention is in a pure state. Preferably, the peptide is ≥80% pure, preferably ≥90% pure, more preferably ≥95% pure, even more preferably ≥99% pure and particularly preferred is a pharmaceutically pure state that is greater than 99.9% pure with respect to contaminating macromolecules, particularly other peptides. It is preferred that the peptide is free of infectious and pyrogenic agents.

Preferably, a purified peptide is substantially free of other peptides. When used in this context, the term "pure" does not exclude the presence of the same peptide in alternative physical forms, such as dimers.

The peptides of the invention may be prepared by chemical synthesis or by recombinant expression in host cells. The preparation by chemical synthesis is preferred. As protein products, compounds of e.g. SEQ ID NO: 2 or any of the other peptides of the present invention are amenable to production by the technique of solution- or solid-phase peptide synthesis. The synthetic peptide synthesis approach generally entails the use of automated synthesizers and appropriate resin as solid phase, to which is attached the C-terminal amino acid of the desired peptide. Extension of the peptide in the N-terminal direction is then achieved by successively coupling a suitably protected form of the next desired amino acid, using either FMOC- or BOC-based chemical protocols typically, until synthesis is complete. Protecting groups are then cleaved from the peptide, usually simultaneously with cleavage of peptide from the resin, and the peptide is then isolated and purified using conventional techniques, such as by reversed phase HPLC using acetonitrile as solvent and tri-fluoroacetic acid as ion-pairing agent. Such procedures are generally described in numerous publications and reference may be made, for example, to Stewart and Young, "Solid Phase Peptide Synthesis," 2nd Edition, Pierce Chemical Company, Rockford, Ill. (1984).

The term "peptidomimetic" refers to a small protein-like chain designed to mimic a corresponding peptide. Peptidomimetics can typically arise either from modification of an existing peptide, or by designing similar systems that mimic peptides, such as peptoids and β-peptides. Irrespective of the approach, the altered chemical structure is designed to advantageously adjust the molecular properties such as metabolic stability and bioavailability without negatively affecting biological activity.

Typically, a peptidomimetic will have an altered backbone such as a Methylated amide group instead of the amide group of a peptide bond to increase the stability of the peptidomimetic against degradation by proteases. Alternatively or in addition, the peptidomimetic may comprise non-natural amino acids or D-enantiomers. A common theme of peptidomimetics is that the molecular changes in the backbone structure and/or in the amino acids should not have a substantial effect on the overall conformation of the peptidomimetic in comparison to the corresponding peptide in order to not negatively affect the biological activity of the peptidomimetic. Thus a peptidomimetic is an isostere of the corresponding peptide. Preferred peptidomimetics are e.g. isosteric peptoids, which comprise poly-N-substituted glycines in the peptide bonds of the backbone. In accordance with the invention, peptidomimetic shall therefore have the same activity in the experiments described hereinafter as the peptides as described hereinafter, such as e.g. a peptide of SEQ ID NO: 1, 2, 3, 4, or 5. The most preferred peptidomimetics are those having five amino acids such as a peptidomimetic of a peptide of SEQ ID NO: 2, 8 amino acids (such as a peptidomimetic of SEQ ID NO: 16, 17 or 18) or 14 amino acids (cf. SEQ ID NO: 6, 7, 8, 9, or 10). Such peptidomimetics are preferably isosteric peptoids, which comprise poly-N-substituted glycines in the peptide bonds of the backbone.

The present invention also contemplates the use of modified forms of peptides or peptidomimetics, e. g. as pharmaceutical compositions for treating breast cancer, and preferably the specific types of breast cancer as mentioned herein, in a human being. Such modified forms relate e.g. to peptides or peptidomimetics which have been chemically modified at their respective N- and/or C-terminus by blocking groups such as FMOC or BOC or alkylation such as Methylation to reduce degradation of the peptides or peptidomimetics e.g. by proteases and to increase stability thereof. Other modifications include acetylating, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, i.e. a cyclic peptide, disulfide bond formation, deMethylation, formation of covalent cross-links, formation of cystine, formation of pyroglutamate, formylation, gamma-carboxylation, glycosylation, GPI anchor formation, hydroxylation, iodination, Methylation, myristoylation, including a myristoylated cyclic peptide, such as a myristoylated cyclic 5mer (based on SEQ ID NO: 2), 6mer, 8mer or 14mer, oxidation, proteolytic processing, phosphorylation, prenylation, racemization, selenoylation, sulfation, transfer-RNA mediated addition of amino acids to proteins such as arginylation, ubiquitination and sumoylation. Examples of such peptidomimetics are given in Table 4. In a preferred embodiment the peptide of the invention is a 14mer pegylated with PEG having a molecular weight of 2000 Da or a PEG having a molecular weight in the range of 200 to 20000 Da, a 14mer, a cyclic 8mer or a cyclic 5mer. A typical peptidomometic can have one or more modification, i.e. can be cyclic and additionally be myristoylated, pegylated, and/or modified in any other way described herein, such as by use of D-amino acids. Typical examples of peptidomimetics include those which have SEQ ID NOs: 1 to 23 with L- and/or D-amino acids.

Cyclization of peptides is performed by methods generally known by a person skilled in the art, such as described in Zitzmann et al. (2005, Journal of Nuclear Medicine, 46(5):782).

The compounds of the invention can also be administered in combination with cytotoxic compounds and/or chemotherapeutic agents. It is possible to administer the compounds of the invention along with one or more cytotoxic compounds and/or chemotherapeutic agents or it is possible to covalently conjugate the cytotoxic compound to the peptide or compound of the invention. The preferred cytotoxic compounds are maytansinoids and preferred chemotherapeutic compounds are taxanes.

In addition or alternatively preferred modified forms of peptides or peptidomimetics in accordance with the invention include e.g. chemically or enzymatically modified forms thereof which have improved biological properties such as improved solubility, absorption, biological half-life, etc. The modifications may alternatively decrease the toxicity of the molecule, eliminate or attenuate any undesirable side effect of the molecule, etc. Modifications which increase e.g. the biological half-life include pegylation, hesylation, pasylation, glycosylation, and/or cyclic with glycosyl structure having sialic acid residues at their end, etc.

The terms "pegylated" and its grammatical variations such as "pegylation" all describe that the peptide or peptidomimetics thereof in their different forms (e.g. in isolated form, as pharmaceutically acceptable salts etc) comprise a PEG moiety, i.e. a polyethylenglycol chain, which is covalently attached to the peptides or peptidomimetics as described herein.

As is described hereinafter, a rat CD44v6 pentapeptide of sequence NEWQG (SEQ ID NO: 11), which is the counterpart to the human CD44v6 pentapeptide of SEQ ID NO:2 and which has been modified with PEG750 or PEG3000 is capable of inhibiting HGF stimulated and CD44 mediated activation of Met and Erk even though at least the PEG3000 moiety has a molecular weight, i.e. 3000 Da, which is significantly higher than the calculated molecular weight of the sequence of SEQ ID NO:11, being approximately 620 Da. Moreover, PEGs of such a molecular weight are known to have an extended zigzag structure. It therefore is surprising that modification of comparatively small peptide such as the pentapeptide of SEQ ID NO:11 does not lead to loss of activity. It seems justified to conclude that the same should apply to the human counterparts such as a pentapeptide of SEQ ID NO:2, peptidomimetics thereof or even longer peptides such as those of SEQ ID NO:6. It is furthermore surprising that inhibition of ERK signaling is even more efficient with pegylated peptides than non-pegylated peptides.

The term "PEG moiety" or "Polyethylenglycol moiety" as used hereinafter refers to PEGs of an average molecular weight of about 200 Da to about 35,000,000 Da. It is preferred to use PEGs which have an average molecular weight of about 400 Da to about 20,000 Da, preferably of about 600 to about 10,000 Da, even more preferably of about 700 Da to about 10,000 Da. The most preferred PEGs have an average molecular weight of about 800 Da to about 8,000 Da, of about 900 Da to about 7,000 Da, of about 1,000 Da to about 6,000 Da such as of about 2,000 Da, of about 3,000 Da, of about 4,000 Da or of about 5,000 Da. In a preferred embodiment, the PEG has an average molecular weight in the range of 200 to 20000 Da.

PEGs are typically named by their average molecular weight. Thus, a PEG with nine repeating units has an average molecular weight of 400 Da and would be labeled as PEG 400. The PEGs contemplated for the present invention may thus be PEGs such as PEG 400, PEG 600, PEG 50, PEG 840, PEG 1000, PEG 1500, PEG 2000, PEG 3000, PEG 3350, PEG 4000, PEG 4600, PEG 8000, PEG 10000, PEG 12000 as they are commercially available e.g. from Sigma-Aldrich.

PEGs may come as straight, branched, star or comb PEGs. Branched PEGs have three to ten PEG chains emanating from a central core group. Star PEGs have 10 to 100 PEG chains emanating from a central core group. Comb PEGs have multiple PEG chains normally grafted onto a polymer backbone.

For the purposes of the invention it is generally preferred to use straight PEGs and particularly preferred to use straight PEGs with an average molecular weight in the range of about 1,000 to 6,000 Da, such as a PEG 2000, PEG 3000, PEG 4000 or PEG 5000 or a PEG of a higher molecular weight.

The PEG moieties may be further modified. For example, the PEG moieties may be covalently modified with fatty alcohol and fatty acids. Such additional modifications may allow the modified pegylated peptides and peptidomimetics to build or be at least incorporated in micelle- or liposome-like structures.

The present invention also relates to such micelle- or liposome-like structures. The pegylated peptides or pegylated peptidomimetics thereof and pharmaceutical compositions comprising such pegylated peptides or pegylated peptidomimetics thereof may provide e.g. for improved drug solubility, reduced dosage frequency, extended circulating half-life, increased drug stability, enhanced protection from proteolytic degradation, etc. The micelle- or liposome-like structures may additionally allow delivering the pegylated peptides or pegylated peptidomimetics more efficiently as the additional modification such as fatty alcohol- or fatty acid-chains may allow improved interaction with cellular membranes. Moreover, the micelle- or liposome-like structures may comprise additional pharmaceutically active agents such as chemotherapeutic agents. In case of pancreatic cancer, these agents may include e.g. gemcitabin. In case of breast cancer, these agents may include Herceptin.

The present invention also relates to such micelle- or liposome-like structures comprising additional pharmaceutically active agents. Such micelle- or liposome-like structures will allow targeting of such chemotherapeutic agents through the pegylated peptides or pegylated peptidomimetics thereof to e.g. the tumors expressing CD44v6 and thus allowing targeted and improved therapy.

The person skilled in the art knows how to modify peptides or peptidomimetics with PEG moieties. The covalent attachment of a PEG moiety may be done chemically or enzymatically.

The first step in chemical modification is typically functionalizing either one or both ends of the PEG polymer. Depending on the fictionalization, one can differentiate between monofunctional, bihomofunctional or biheterofunctional PEGs.

The chemical Pegylation process can be generally categorized into two types, namely a solution phase batch process or an on-column fed-batch process. The commonly adopted batch process involves the mixing of reagents in a suitable buffer solution, preferably at a temperature of 4 to 6° C., followed by separation and purification of the desired product using techniques such as size exclusion chromatography, ion exchange chromatography or hydrophobic interaction chromatography.

The choice of the suitable functional group for the PEG derivative is based on the type of available reactive group on the molecule that will be coupled to the PEG. For proteins and peptides, typical reactive amino acids include lysine, cysteine, histidine, arginine, aspartic acid, glutamic acid, serine, threonine, tyrosine. The N-terminal amino group and the C-terminal carboxylic acid can also be used as a site specific site by conjugation with aldehydes functional polymers. If it is preferred to not react an amino acid with a PEG, but only e.g. the N-terminus of a peptide, one can block the functional groups in amino acids, e.g. with FMOC, pegylate the peptide and then de-block the amino acids.

The techniques used to form PEG derivatives such pegylated peptides are generally reacting the PEG polymer with a group that is reactive with hydroxyl groups, typically anhydrides, acid chlorides, chloroformates and carbonates. In the second generation Pegylation chemistry more efficient functional groups such as aldehyde, esters, amides etc. made available for conjugation.

Heterobifunctional PEGs are very useful in linking two entities, where a hydrophilic, flexible and biocompatible spacer is needed. Preferred end groups for heterobifunctional PEGs are maleimide, vinyl sulfones, pyridyl disulfide, amine, carboxylic acids and NHS esters.

The pegylated peptides and pegylated peptidomimetics thereof in accordance with the invention may be provided in the form of pharmaceutical compositions comprising optionally pharmaceutically acceptable excipients.

In the following it is set out how the compounds in accordance with the present invention, i.e. the peptides, peptidomimetics thereof and modified forms thereof, the pharmaceutical compositions comprising these compounds and Methods making use of these compounds may be used for the treatment of metastasizing cancer in a human being. It is to be understood that, whenever reference is made in the following to the treatment of metastasizing cancer, this reference, as a preferred embodiment, always contemplates to use the pentapeptides as described hereinafter, namely those of SEQ ID NO: 1, SEQ ID NO: 2, SEQ ID NO: 3, SEQ ID NO: 4 and SEQ ID NO:5, and in particular those of SEQ ID NO: 2, peptidomimetics thereof, or modified forms thereof such as the pegylated forms thereof.

As can be taken from the experiments described hereinafter, the peptides used in the experiments were capable of inhibiting metastasis formation in pancreatic cancer models as well as inducing regression of already formed metastases. As mentioned, the invention relates to the use of compounds, pharmaceutical compositions and the application of Methods as described herein for the treatment of specific breast cancers, and preferably of specific metastasizing breast cancers.

Breast cancers in accordance with the invention include for which expression of CD44v6 has been observed on cancer tissues or can be observed upon corresponding testing e.g. with CD44v6 antibodies. Thus, in order to see whether a patient is eligible for treatment with compounds and pharmaceutical compositions as described herein, one may take a biopsy of tumor tissue and test for expression of CD44v6. The preferred specific breast cancers forms that are considered for treatment by the compounds and pharmaceutical compositions mentioned herein include breast cancer forms, that are dependent on EGF-based ErbB activation for their tumorgenicity, that do not show an increased expression or activation of TGFα, and/or that are resistant to treatment with Trastuzumab or Pertuzumab and which show increased expression of Met. In one embodiment, the invention considers to inhibit formation of metastases in such patients. In another embodiment, these breast cancer types are metastasizing, i.e. metastases have already formed, breast cancers, which may be classifiable according to the TNM anatomic/prognostic group system of the cancer staging system of the American Joint Committee on Cancer. For such metastasizing cancers, the compounds of the invention may lead to a regression of the already formed metastases. Preferably all these breast cancer types show expression of CD44v6.

In general, these specific cancer types independent of whether they are already metastasizing or not, can be identified and distinguished from other cancer types, such as estrogen-receptor dependent breast cancer, which is not treatable by the compounds in accordance with the invention, through common diagnostic approaches such as taking biopsies, expression profiling etc. A particularly useful categorization is provided by the TNM Anatomic Stage/Prognostic Group System of the Cancer Staging Manual of the American Joint Committee on Cancer ($7^{th}$ edition, 2010, Springer). It is preferred for the purpose of the invention that breast cancers are categorized according to these principles and supplemented where necessary, e.g. by expression profiling for EGF, TGFα and ErbB1 and 2.

Metastasizing breast cancers in general and metastasizing forms of the afore-mentioned specific breast cancer forms can be identified be taking a biopsy of tumor tissue and test for expression of CD44v6. If the tumor can be shown to express CD44v6 and if metastases have started to form or have already formed and maybe even spread through the body, this tumor is considered as a metastasizing cancer in accordance with the invention. If the tumor moreover shows upregulated activity of EGF, but not for TGFα, the tumor will be considered as a metastasizing form of an EGF-dependent breast cancer form, in which no autocrine loop for TNF-α occurs.

The decision as to whether the tumor is to considered as metastasizing form of any of the specific breast cancer types mentioned herein can be made according to the TNM Anatomic Stage/Prognostic Group System of the Cancer Staging Manual of the American Joint Committee on Cancer ($7^{th}$ edition, 2010, Springer).

Metastasizing breast cancers in accordance with the invention may be classified as Stage III or Stage IV cancers according to the TNM Anatomic Stage/Prognostic Group System of the Cancer Staging Manual of the American Joint Committee on Cancer ($7^{th}$ edition, 2010, Springer). The TNM (tumor node metastasis) staging system of the American Joint Committee on Cancer allows staging, i.e. classification of cancers by the size and extent of the primary tumor (T), the question if regional lymph nodes (N) are affected and if distant metastases can already be detected (M). This indication is then typically taken as an indication for different routes to take in treating the patient and also allows a reliable prognosis of the diseases. This is why the TNM system has become an indispensable tool for oncologists. The parameter M receives a value of 0, i.e. M0 if no distant metastases can be detected clinically although they may have started to develop. If M is set at M0, a patient depending on the values of T and N may be classified as Stage III. Thus for e.g. any T, N3 and M0, a patient may be classified as Stage III, or Stage Inc in case of e.g. breast cancer (see page 362, Cancer Staging Manual of the American Joint Committee on Cancer ($7^{th}$ edition, 2010, Springer). If such a Stage III patient or a patient having the highest subclass of Stage III (such as Stage IIIC for breast cancer) additionally displays circulating tumor cells and micrometastases in the bone marrow, this will worsen the prognosis. Thus, for the purposes of the present invention a metastasizing cancer may be classifiable as Stage III according to the TNM Anatomic Stage/Prognostic Group System of the Cancer Staging Manual of the American Joint Committee on Cancer ($7^{th}$ edition, 2010, Springer).

Preferably, for a metastasizing cancer in accordance with the invention M is M1, i.e. that distant metastasis can be clinically detected so that such a metastasizing tumor can be classified as Stage IV according to the TNM Anatomic Stage/Prognostic Group System of the Cancer Staging Manual of the American Joint Committee on Cancer (7$^{th}$ edition, 2010, Springer).

A particularly preferred embodiment thus refers to the use of the pentapeptides described hereinafter, e.g. of SEQ ID NO: 1, 2, 3, 4, or 5 and most preferably of SEQ ID NO:2, peptidomimetics thereof or modified forms thereof, and pharmaceutical compositions comprising these compounds for the treatment of breast cancer, preferably of the specific breast cancers forms mentioned herein, and even more preferably for treatment of metastasizing forms. The metastasizing forms are classifiable as Stage IV according to the Cancer Staging Manual of the American Joint Committee on Cancer.

The compounds and salts thereof can be formulated as mentioned above as pharmaceutical compositions (e.g. liquids, suspensions, emulsions, lozenges, sachets, ampoules, aerosols, powders, granules, tablets, pills, capsules, injections, solutions etc.) comprising at least one such compound alone or optionally in a mixture with pharmaceutically acceptable carriers, excipients and/or diluents.

The compounds/salts thereof and pharmaceutical compositions may be formulated for oral administration, e.g. by inhalation, for nasal administration or for administration by injection such as subcutaneous injection.

The invention is now described with respect to experiments, which, however, are not to be construed in a limiting sense.

EXAMPLES

Example 1

CD44v6- and Ligand-Dependent Activation of ErbB Receptor Family Members

1. Material and Methods
Cell Lines

| Name | Description | Culture Medium |
|---|---|---|
| HT29 | human colon adenocarcinoma line | DMEM, 10% FCS |
| BSp73AS (AS10) | Human colon carcinoma line | RPMI1640, 10% FCS |
| BSp73ASv6 (ASs6) | AS 10 cells transfected with CD44v6 | RPMI1640, 10% FCS, 0.3 g/l G418 |
| HeLa | Human cervix carcinoma line | DMEM, 10% FCS |
| MCF 7 | Human mammary pleural effusion cell line | DMEM, 10% FCS, |
| MCF 10A | Human pre-neoplastic mammary cell line | DMEM/F12, 5% horse serum, 20 ng/ml EGF, 0.5 µg/ml Hydrocortisone, 100 ng/ml cholera toxin, 10 µg/ml insulin, 100 IU/ml Penicillin, 100 µg/ml streptomycin |
| Ecopack 2-293 | Human embryonic kidney cell line used for production of high titer Moloney-based retroviral stocks by transient transfection | DMEM, 10% FCS, 4 mM L-glutamine, 100 U/ml penicillin, 100 µg/ml streptomycin, 1 mM sodium pyruvate |

Antibodies

| Antibodies | Isotype | Epitope | Source |
|---|---|---|---|
| α-ErbB1 | Rabbit IgG1 | Detects ErbB1 in H, M | Millipore |
| α-ErbB2 | Rabbit IgG1 | Detects ErbB2 in H, M, Mk, R | Millipore |
| α-Erk (K-23) | Rabbit IgG1 | Detects Erk1/2 in H, R, M | Santa Cruz |
| α-CD44var(v6) clone VFF18 | Mouse IgG1 | Detects an epitop encoded by exon v6 on the variant portion of human CD44 | Medsystems |
| α-Phospho-ErbB1 | Mouse IgG1 | Detects phosphorylated ErbB1 in H, R, M, Ca | Millipore |
| α-Phospho-p44/42 | Rabbit IgG1 | Detects MAP kinase phosphorylated Erk1/2 in H, R, M | New England Biolabs |
| α-CD44v3 | Mouse IgG1 | Detects an epitope encoded by exon v3 on the variant portion of human CD44 | R&D Systems |
| Hermes 3 | Mouse IgG1 | Detects all isoforms of CD44 of human origin | Gift of Sirpa Jalkanen, Turku, Finnland |
| α-VSV-G | Mouse IgG1 | Detects the VSV-G tag | Santa Cruz |

Oligonucleotides

```
α-CD44v6 siRNA-1:
                              (SEQ ID NO: 16)
5' - AGU AGU ACA ACG GAA GAA ATT - 3'
α-CD44v6 siRNA-2:
                              (SEQ ID NO: 17)
5' - GGA UAU CGC CAA ACA CCC ATT - 3'
α-CD44v3 siRNA-1:
                              (SEQ ID NO: 18)
5' - AGG CAU UGA UGA UGA UGA AUU - 3'
α-CD44v3 siRNA-1:
                              (SEQ ID NO: 19)
5' - UGA AGA UGA AAG AGA CAG AUU - 3'
```

Plasmid Constructs

Human ErbB1 pBabe puro: The sequence of human ErbB1 was cloned into pBabe puro (Morgenstern & Land, 1990, see references), Human ErbB2 pBabe puro: The sequence of human ErbB2 was cloned into pBabe puro (Morgenstern & Land, 1990, see references)

General Cell Culture

Cells were cultivated in a humid (95%) atmosphere with 5% CO2 at 37° C. All handling of the cells was performed under sterile conditions. The cultivated cells were passaged as soon as they reached a level of 80% confluency.

Passaging of Cells

After the removal of the growth medium the cells were treated with 0.25% Trypsin/EDTA and incubated for 5 mins at 37° C. The disassociated cells were then taken up in growth medium and spun down at 1200 rpm for 3 mins. The supernatant was removed, the cell pellet resuspended in growth medium and plated in new culture plates in the desired dilution.

Blocking with the CD44v6-Specific Peptide

3×10$^5$ were seeded per well of a 6-well plate and serum-starved for 24 hours. Afterwards the medium inside of each well was reduced to 1 ml and the respective peptide (v6 (both peptides of SEQ ID No.: 2 and 6 were tested), or ctrl peptide) was added at a concentration of 100 ng/ml. The cells then were incubated together with the peptide at 37° C. for 5 mins. Ligand concentration for all peptide blocking experiments was 20 ng/ml.

Induction of Cells with Growth Factors

The cells were incubated with the growth factors specified in the particular experiment. Except for the peptide blocking and migration assays, ligand concentration was 5 ng/ml at all times. Prior to induction the cells were treated as indicated in the results section.

Cell Lysate Preparation

To assay protein expression via Western blot cells were washed 1× with PBS and afterwards lysed in 2×Laemmli sample buffer (160 mM Tris-HCl pH 6.8, 4% SDS, 16% glycerol, 0.1M DTT, 0.01% bromphenol blue). The sample was sheared through a 26 gauge needle. In succession the lysates were boiled for 5 mins at 99° C. in order to denature the proteins in the sample and then spun down at 10 000 rmp for 1 min Eventually the samples were loaded onto an SDS-PAGE gel.

Co-Immunoprecipitation of ErbB1 and CD44v6

$5 \times 10^6$ cells were seeded in 15 cm plates, serum starved for 24 hours and induced with EGF (5 ng/ml) or left untreated respectively in succession. Afterwards the cells were washed with ice-cold PBS and incubated with low salt RIPA buffer (10 mM Trips pH 7.4, 10 mM NaCl, 3 mM EDTA, 1% Triton X-100, 1% sodium desoxycholate, 0.1% SDS) on ice for 30 mins. The cells were then scraped off the plates and transferred into 1.5 ml Eppendorf tubes. The samples were spun down for 20 mins at 4° C. and 12 000 rpm and the supernatant was transferred to a new tube afterwards. 5 µg of antibody for each ml of cell lysate were added and incubated with the lysates for 1.5 hours at 4° C. under constant shaking. 25 µl of each protein-A and protein-G agarose beads were then added to the samples and incubated for 2 more hours at 4° C. under constant shaking. The immuno-complexes were then isolated by centrifugation at 12 000 rpm and 4° C. and washed 3× with ice-cold lysis buffer. The supernatant was then removed and the immuno-complexes were resuspended in 25 µl 2×Laemmli buffer+ 1M DTT and boiled at 99° C. for 5 mins. Afterwards the supernatant was ready to be loaded onto an SDS-PAGE gel.

Transfection of Target Cells with siRNA

The particular cells were transfected transiently with Lipofectamin 2000 (Invitrogen) according to the manufacturer's instructions. $3 \times 10^5$ cells were seeded per well of a 6-well plate, cultivated for 24 hours and then transfected. For each transfection separate mixes were prepared:
1. 200 pmol siRNA in 250 µl of serum-free medium
2. 5 µl Lipofectamin 2000 in 250 µl serum free medium The mixes were incubated for 5 mins at room temperature and afterwards transferred into one common Eppendorf tube. After a further incubation period of 20 mins at room temperature the target cells were transfected with the complete mix. The medium of the transfected cells was changed 6 hours after transfection and substituted with fresh medium. After 24 to 48 hours the cells were serum-starved and afterwards used for the successive experiments.

Heparinase II Treatment of HT29 Cells

HT29 cells were seeded at a concentration of $3 \times 10^5$ per well of a 6-well plate and serum starved 24 hours later. After starvation the medium in the treated 6-wells was reduced to 1 ml and heparinase II at a concentration of 6 U/ml was added. The treated cells were incubated together with the enzyme for 3 hours and afterwards treated directly with the indicated growth factors. Cells were then washed with cold PBS and lysed in 2×Laemmli buffer in order to examine them further.

Transfection of BSp73AS Cells with ErbB1

24 hours prior to transfection the packaging cell line Ecopack-2-293 was seeded in a 6-well plate at a concentration of $2 \times 10^5$ cells per well. 1.5 hours before transfection, the growth medium was replaced with growth medium containing 25 µM chloroquine. Each 6-well was then transfected with 4 µg of the ErbB1 or the ErbB3 plasmid DNA by using the CalPhos Mammalian Transfection kit (Clontech). The transfection was done according to the manufacturer's instructions. After 48 hours, the medium containing the virus was collected and filtered through a 0.45-µm cellulose acetate filter. The virus containing medium was then added to BSp73AS cells that had been seeded at a concentration of $0.5 \times 10^5$ cells per well 24 hours earlier at a concentration of 1:2 to normal growth medium. Polybrene to a final concentration of 8 µg/ml was added and the cells were incubated for 6-8 hours together with the virus. The virus containing medium was then replaced by normal growth medium and the cells were further incubated over night. Afterwards the cells were serum-starved and treated with the indicated growth factors.

CD44-Variant-Exon-Specific RT-PCR Analysis in MCF7 and MCF10A Cells

The exon specific RT-PCR was performed as described previously (Orian-Rousseau et al. 2002, see references, Konig et al. 1996, see references). All primers, but the v8 forward primer (5'-CGC TTC AGC CTA CTG CAA AT-3') (SEQ ID NO: 20) were identical to those used by Konig et al. (1996), see references.

In Vivo Metastasis Assay

All animals were handled according to German regulations for animal experimentation. The animal experiments were approved by the Regierungspräsidium Karlsruhe (35-9185.81/G-83/04). All mice were obtained from Harlan. $1 \times 10^6$ murine 4T1 cells (diluted in either 20 mg of control peptide or 20 mg of CD44v6 peptide (peptides of SEQ ID No.: 6 were tested) in PBS) were orthotopically injected into the mammary fat pad of female BALB/c mice. In succession, 5 of the mice were injected intraperitoneally with a CD44v6-peptide (20 µg per mouse) (peptides of SEQ ID No.: 6 were tested) and 5 of the mice were injected with an unspecific control peptide (20 µg per mouse) three times a week. After four weeks, the mice were sacrificed and the tumors as well as the lung and lymph nodes of the animals were extracted. These organs were then fixed in 4% Formalin, processed and embedded in paraffin.

2. Results

EGF-Induced Activation of the ErbB Receptors is Dependent on CD44v6

In order to test whether CD44v6 plays a role in the activation of the ErbB family of receptors, a peptide blocking experiment using the 14mers of SEQ ID No. 6 was performed in HT29 cells. The fact that this cell line expresses all ErbB receptors (Wu et al, 2009, see references) and several CD44 variants including also exon v3 and v6 (Orian-Rousseau et al., 2002, see references) makes it a suitable tool to evaluate the co-receptor function of CD44 proteins for the ErbB family. The first ErbB1-ligand that was evaluated was EGF. To test whether the activation of the ErbB receptors by EGF was dependent on CD44v6, HT29 cells were preincubated with a v6-peptide of SEQ ID NO: 6 that specifically inhibits the co-receptor function of CD44v6 or an unspecific control peptide. The cells were serum starved for 24 hours and induced with EGF. Phosphorylation of the Erk-Kinase, a downstream target of the ErbB receptor family, was used as a read-out for ErbB receptor activation. HGF was used as a control to test the blocking efficiency of the CD44v6 peptide since the induction of the Erk kinase through Met is dependent on CD44v6 (Orian-Rousseau et al., 2002, see references).

EGF or HGF-induction of the HT29 cells lead to the phosphorylation of the Erk-kinase. The EGF- as well as HGF-dependent Erk-phosphorylation could be inhibited by pre-incubation with the CD44v6 peptide whereas a control peptide showed no effect. This suggests that EGF, is dependent on CD44v6 in order to activate the ErbB receptors (FIG. 2). This is similar to the situation observed in the case of Met and its ligand HGF.

The Requirement for CD44 is Receptor-Independent

Besides EGF, five other ligands, namely AR, BC, ER, HB-EGF, and TGFα, can activate the ErbB1 receptor. EGF, AR and TGFα bind to either an ErbB1-homo- or an ErbB1/2-heterodimer. In addition to these dimers, BC, ER and HB-EGF can also bind to an Erb4/4 homo- or an ErbB2/4 heterodimer. It was investigated whether the activation of the ErbB receptors by the indicated ligands is also dependent on CD44v6. HT29 cells were serum-starved for 24 hours and pre-treated with the v6-specific or a control peptide. They were then induced with the indicated ErbB ligands. Erk-kinase phosphorylation was used as a read-out for receptor activation.

All ligands could activate the Erk-kinase. EGF- as well as ER-dependent Erk-phosphorylation was inhibited by pre-incubation of HT29 cells with the CD44v6 peptide whereas a control peptide showed no effect (FIG. 3). This shows that, besides EGF, ER is another ErbB1 ligand that is dependent on CD44v6 as a coreceptor. In contrast, AR, BC, HB-EGF and TGFα-induced activation of the ErbB receptors could not be inhibited by blocking CD44v6 (FIG. 3). These ligands are independent of CD44v6 for their induction of the ErbB receptors. This is especially striking, since EGF and TGFα address the same receptor pairs (ErbB1/1 or ErbB1/2). These data suggest that the specific CD44 isoform used as a co-receptor for ErbB-activation is determined by the ligand that activates the ErbB receptors and not by the receptor proteins themselves.

Using the CD44v6 peptide as a blocking reagent, EGF- as well as ER-dependent activation of the ErbB family was shown to be inhibited. To further confirm that EGF and ER require CD44v6 as a co-receptor the effect of the downregulation of CD44v6 expression was evaluated. HT29 cells were transfected with either CD44v6-specific siRNA or an unspecific control siRNA. HeLa cells were used in addition and treated in a similar way to rule out that our findings are cell type specific. Then the cells were serum-starved for 24 hours followed by induction with either EGF or ER.

In addition to Erk-phosphorylation, ErbB1 receptor phosphorylation was used as a read-out for the receptor activation. By probing for the ErbB1-phosphorylation status it was possible to determine whether a block in ErbB signaling was only affecting downstream targets like the Erk-kinase or also the ErbB1 receptor itself.

EGF and ER induction of the cells lead to ErbB1 and Erk phosphorylation. Upon transfection of CD44v6 specific siRNA into HT29 cells, the expression of CD44v6 was reduced as indicated by the western blot probed with a CD44v6 specific antibody (αCD44v6). This lead to an inhibition of EGF- as well as ER-induced signaling on the ErbB1- as well as on the Erk-level. A control-siRNA showed no effect on CD44 expression or ErbB signaling (FIG. 4). The downregulation of CD44v6 in HeLa cells also lead to an inhibition of EGF- as well as ER-induced ErbB signaling showing that the requirement for CD44v6 is not cell type specific (FIG. 4).

Using the CD44v6 peptide as a blocking reagent TGFα induced phosphorylation of the Erk kinase could not be inhibited. To confirm that TGFα does not require CD44v6 as a co-receptor for its induction of the ErbB receptor family and to test whether TGFα might possibly be completely independent of CD44, the effect of the downregulation of CD44v6 and the downregulation of all CD44 isoforms in HT29 cells was tested in the same experiment. Different HT29 cells were transfected either with CD44v6 specific siRNA, siRNA against all CD44 proteins (CD44pan), or an unspecific control siRNA. The cells were then serum-starved and induced with TGFα or EGF. EGF was used as a control for the inhibiting effect of the CD44 downregulation. After growth factor induction, the activation of the ErbB family was measured on the level of ErbB1 and Erk.

EGF as well as TGFα induction of the HT29 cells lead to ErbB1- as well as Erk-phosphorylation. Upon down-regulation of CD44v6 a block in EGF signaling on the ErbB1 as well as on the Erk-level could be observed (Figure. 5). TGFα-dependent signaling was not inhibited by a downregulation of CD44v6. Even the transfection of CD44 pan siRNA did not lead to a block of TGFα-dependent signaling although the expression of all CD44 isoforms was inhibited. As expected, EGF-dependent signaling could be abolished by down-regulation of all CD44 isoforms. An unspecific siRNA did not show any effect on either CD44 expression or ErbB receptor activation (FIG. 5).

Induction of the ErbB receptors through TGFα is not dependent on CD44v6. Moreover, activation of the ErbB receptors through TGFα is independent of CD44, as even a complete down-regulation of all CD44 proteins does not abolish its ErbB activation.

HB-EGF-Induced Activation of the ErbB Receptors is Dependent on CD44v3

TGFα is not the only ErbB1 ligand that is independent of CD44v6 for its induction of the ErbB receptors. Using the CD44v6 peptide I was not able to block BC, AR or HB-EGF-dependent activation of the Erk-kinase. HB-EGF and AR are heparan-binding growth factors (Cook et al, 1991, see references; Higashiyama et al, 1992, see references). Their binding to heparan might be instrumental for their activation of the ErbB receptors. In order to test whether heparan sulphation is involved in the process of AR- and HB-EGF-induced ErbB receptor activation, serum-starved HT29 cells were treated with heparinase, an enzyme that cleaves off heparin-sulphate of the surface of target cells. The cells were then induced with HB-EGF or AR. HGF was used as a control since for its activation of Met it is dependent on CD44v6, an isoform that is not heparin-sulphated (Orian-Rousseau et al., 2002). Therefore, removal of heparan sulphate should have no effect. The Erk-kinase was used as a read-out for receptor activation since it is activated by Met- as well as by the ErbB receptors.

Induction of HT29 cells with HGF, HB-EGF or AR lead to Erk-phosphorylation. Upon Heparinase treatment, the activation of the ErbB-receptors through HB-EGF but not AR was abrogated (Figure. 6). This shows that for its induction of the ErbB receptors, HB-EGF is dependent on heparan-sulphation whereas AR is not. In the CD44 protein family, CD44v3 is the only variant of CD44 that carries heparan-sulphate side chains. In order to test whether CD44v3 mediates HB-EGF-dependent activation of the ErbB receptors, CD44v3 was down-regulated by RNAi technology.

HT29 cells were transfected with CD44v3-specific siRNA or an unspecific control siRNA. Then the cells were serum-starved for 24 hours followed by their induction with HB-EGF. EGF was used as a control since it is dependent on CD44v6 and its activation of the ErbB receptors should not be affected by the down-regulation of CD44v3. ErbB1- and Erk-phosphorylation was used as read-out for receptor activation.

Induction of the HT29 cells with EGF or HB-EGF lead to phosphorylation of the ErbB1 receptor and of the Erk-kinase. Upon downregulation of CD44v3 by means of siRNA the induction of the ErbB receptors through HB-EGF was blocked, whereas a control siRNA had no effect (FIG. 7). This suggests that HB-EGF is dependent on CD44v3 for its ErbB1-stimulating activity. In contrast, EGF is independent of CD44v3 (FIG. 7). In conclusion, depending on the ligand, specific CD44 variant isoforms can act as co-receptors for the same ErbB-receptor.

Evaluation of ErbB1-Homodimer Signaling

In order to activate the ErbB1 receptor, EGF, ER, HB-EGF and TGFα bind to ErbB1 homodimers or ErbB1/2 heterodimers. ER and HB-EGF can additionally bind to an ErbB4/4 homo- or an ErbB2/4 heterodimer. The cell lines that were used for the experiments (HeLa and HT29 cells) express all ErbB receptors. Under these conditions the activation of the ErbB1 receptors through the indicated ligands might be mediated by ErbB homodimers as well as heterodimers. To undoubtedly study the effect of ligand induction on an ErbB1 homodimer, the BSp73AS pancreatic cell system was tested. In these cells none of the four ErbB family members and only the standard isoform of CD44 (which includes no variant exon) are expressed. The ErbB1 or the ErbB3 receptor were introduced into several transfected BSp73AS cell lines expressing specific CD44 variants (Rudy et al, 1993, see references; Seiter et al, 1993, see references; Sleeman et al, 1997, see references; Sleeman et al, 1996, see references). ErbB3 is not able to bind to any of the ligands tested here and therefore was used as a control for infection.

Due to the very low transfection efficiency of the BSp73AS, a retroviral infection system was used. The ErbB1 and ErbB3 gene sequences were inserted into a lentiviral expression vector that was then introduced into the packaging cell line Ecopack 2-293. Ecopack 2-293 cells stably express the viral gag, pol, and env genes that are necessary for virus particle formation and replication. The retroviral expression vector provides the packaging signal, transcription and processing elements, and the target gene (ErbB1 or ErbB3). After the transfection of the retroviral vector into the ecopack 2 cells, they produce high-titer, replication-incompetent virus containing the gene of interest. This virus is then collected and can infect target cells and transmit target genes; however, it cannot replicate within the infected cells because the viral structural genes are missing.

After 48 hours, the cell medium containing the virus was collected and added to either BSp73AS cells that only express CD44s (AS cells) or to cells that express CD44s together with CD44v6 (ASs6 cells). These cells were serum-starved followed by their induction with either EGF or TGFα. The expression of the ErbB1 receptor was detected by means of an ErbB1-specific antibody. ErbB1- and Erk-phosphorylation was then analyzed in ErbB1- and control-transfected cells in the presence or absence of EGF or TGF-α.

In AS- as well as in ASs6 cells expression of ErbB1 was detected. In both ErbB1-expressing cell lines TGFα induced the activation of the ErbB1 receptor and of the Erk kinase. EGF on the other hand was only able to activate ErbB1 in ASs6 cells where CD44v6 is present. EGF is dependent on CD44v6 for the induction of ErbB1 homodimers. In the control cells no receptor activation could be measured (FIG. 8).

To test the requirement of CD44v6 for ER-based ErbB1-homodimer-activation, similar procedures as described above were performed. Cells were also induced with TGFα as a control for an ErbB1 activation that is independent of CD44. Similar to EGF, ER could only induce ErbB1 activation in cells that express CD44v6, whereas TGFα was able to activate the ErbB1 receptor independently of CD44v6 expression (FIG. 9). ER is dependent on CD44v6 for the induction of ErbB1 homodimers.

Control Cells Showed No Receptor-Activation.

To test whether HB-EGF can activate ErbB1-homodimers in the presence of CD44v3, ASs6 cells that express CD44s together with CD44v6 and cells that express CD44s together with one isoform of CD44 that includes the sequences of all of its variant exons (ASv1-10) were infected with the ErbB1 receptor protein. The cells were then serum-starved and induced with either HB-EGF or EGF (as a control for CD44v6-dependent ErbB1 activation). The expression of the ErbB1-receptor was then detected and its activation evaluated by measuring ErbB1- or Erk-phosphorylation.

In cells that express CD44v1-10, HB-EGF could induce the ErbB1 receptor while it could not do so in the ASs6 cells where CD44v3 is absent. EGF was able to induce ErbB1 in ASs6 cells as well as in ASv1-10 cells since the v6 sequence is present in both transfectants. The control cells showed no receptor activation (FIG. 10).

The Role of CD44v6 in Breast Cancer

The ErbB receptors play a paramount role in human breast cancer where the activation of the ErbB receptors, particularly ErbB1 and 2 have been shown to be deregulated (Hynes & MacDonald, 2009, see references). The cells used in my experiments so far were colon- or cervix-carcinoma lines. In order to address the role of CD44v6 in breast cancer, MCF7 and MCF10A cells were used. MCF7 cells are pleural effusion cells from an invasive breast ductal carcinoma whereas MCF10A cells are preneoplastic mammary epithelial cells.

The expression of CD44 in these cell lines was examined by a run-off PCR analysis. MCF7 and MCF10A cells were lysed, the total RNA was isolated from the lysates and converted into cDNA via reverse transcription. Then PCR reactions were performed with specific forward primers for each variable exon of CD44 and one common backward primer in the constant region of CD44 (see FIG. 11).

A run-off PCR permits the determination of both structure and approximate abundance of CD44 isoforms in the cells. The size of a specific band corresponds to the exons that are expressed between the two respective primers. Consequently, if the bands corresponding to adjacent exons form a ladder it indicates that they are expressed together in a larger isoform. A ladder formed for example by v2 to v10 suggests that the CD44 variants v2-10 are expressed as one transcript.

MCF7 as well as MCF10A cells express CD44v2-10 predominantly in one large transcript as well as several other smaller transcripts (Figure. 12). Thus, these cells not only express the ErbB1 receptor (Gramlich et al, 1993, see references; Rodriguez-Fragoso et al, 2009, see references) but also CD44 variants that could act as co-receptors for the ErbB receptors.

To test whether CD44v6 acts as a co-receptor in MCF7 or MCF10A cells, a peptide blocking experiment using peptides of SEQ ID NO: 6 was conducted. The cells were serum-starved for 24 h and then pre-incubated with a v6 peptide or an unspecific control peptide. Then, the cells were induced with EGF or HGF as a control. As a read-out for ErbB-activation, the phosphorylation of the Erk-kinase was used.

In MCF7 as well as in MCF10 cells, the activation of the ErbB receptors by EGF could be blocked by a CD44v6-specific peptide, whereas an unspecific control peptide showed no effect. CD44v6 is required as a co-receptor for EGF-induced ErbB-activation in these breast cancer cells (FIG. 13). To further confirm this result, the CD44v6 expression was downregulated in MCF7 cells by CD44v6-specific siRNA. SiRNA based downregulation of CD44v6 in MCF7 cells significantly reduced the activation of the ErbB receptors as deduced by the inhibition of the Erk signal. This confirms that the action of CD44v6 as a co-receptor for EGF-based ErbB activation is indeed required in breast cancer cells (FIG. 14).

Complex Formation Between CD44v6 and the ErbB1 Receptor Protein

The collaboration between the ErbB1-receptor and CD44v6 for EGF-dependent receptor activation in breast cancer cells suggests that these two proteins are located in close vicinity. In this final paragraph I tested whether ErbB1 and CD44v6 form a complex. To this end, a co-immuno-precipitation experiment was performed. Serum-starved MCF10 cells were treated with EGF (or left uninduced) and ErbB1 was subsequently immunoprecipitated with an ErbB1-specific rabbit antibody. The precipitates were then probed for the presence of CD44v6. As a control, a CD44v6 precipitate was loaded on the gel. The specificity of the IP was controlled using an unspecific rabbit IgG.

In MCF10 cells, CD44v6 could be immunoprecipitated together with ErbB1. Interestingly, this complex formation was inducible and could only be found in cells that were treated with EGF. CD44v6 is in a complex with ErbB1 when it acts as a coreceptor for its EGF-based induction (FIG. 15).

In Vivo Metastasis Assay

Murine 4T1 cells that are highly metastatic were used. In these cells, similar to MCF10A cells, the ErbB receptors can be activated by EGF and this activation is dependent on CD44v6 (unpublished data). 4T1 cells were originally derived from a spontaneously arising BALB/c mammary tumor (Aslakson & Miller, 1992, see references). When introduced orthotopically, 4T1 cells grow rapidly at the primary site and form metastases in the lung and the lymph nodes over a period of 3-6 weeks. The tumor growth and metastatic spread of 4T1 cells in BALB/c mice very closely mimics human breast cancer and is an animal model for stage IV human breast cancer (Tao et al, 2008, see references). 4T1 cells were orthotopically injected into the mammary fat pad of female BALB/c mice. The mice were injected i.p. with a CD44v6 peptide (SEQ ID NO: 6) or a control peptide 3 times a week. After the mice were sacrificed, the tumors as well as the lungs and lymph nodes of the mice were retrieved, fixed and embedded in paraffin. In order to test whether there was a difference in metastatic behavior of the 4T1 cells between CD44v6 and control peptide treated animals, the paraffin blocks corresponding to lungs and lymph nodes are analyzed.

In summary, this data indicates that ligands of the ErbB receptor family make use of specific variant isoforms of CD44 in order to induce their cognate receptors. While TGFα appears to be independent of the CD44 family, EGF and ER depend on CD44v6 for their induction of the ErbB receptors. HB-EGF is dependent on CD44v3.

Example 2

CD44v6 Peptides can Affect Regression of Metastases

1. Material and Methods
Cell Lines

The rat pancreatic carcinoma cell line BSp73AS (also designated AS) and its transfectants have been described (Orian-Rousseau et al., *Genes & Development* (2002), 16:3074-3086) and were grown in RPMI (Invitrogen, Karlsruhe, Germany) plus 10% FCS. The human pancreatic cancer cells L3.6pl (Bruns et al., *Neoplasia* (1999), 1, 50-62) were maintained in DMEM (low glucose; Invitrogen, Karlsruhe, Germany) supplemented with 10% FCS (PAA, Cölbe, Germany), sodium pyruvate, nonessential amino acids, L-glutamine, and MEM vitamin solution (Pan Biotech, Aidenbach Germany).

Antibodies and Other Reagents

The human monoclonal antibody against CD44v6 (VFF18) was a gift from Bender (eBioscience, Campus Vienna Biocenter 2, A-1030, Vienna, Austria), the anti-Erk 1 (K-23), c-Met (C-28) and GFP antibody (sc-101525) were from Santa Cruz Biotechnology (Heidelberg, Germany), the cleaved Caspase-8 antibody (IMG-5703) from Imgenex (San Diego, Calif., USA), the CD31 antibody (MEC13.3) from BD Biosciences, Heidelberg, Germany, and the cleaved Caspase-3 (Asp175), Phospho-Met (Tyr1234/1235) (D26), Met (25H2) and the phospho-ERK phospho-p44/42 antibodies from Cell Signaling Technology (Beverly, England). The rat exon v6-specific antibody 1.1ASML has been described (Gunthert et al., *Cell* (1991), 65, 13-24). Secondary antibodies labeled with horseradish peroxidase were from Dako (Glostrup, Germany). The Alexa Fluor R 546 goat anti-rabbit secondary antibody was purchased from Life Technologies (Darmstadt, Germany). HGF was purchased from Peprotech (Hamburg, Germany). The CD44v6 rat and human peptides (14mer and 5mer) have been described (Matzke et al. *Cancer Res.* (2005), 65(14), 6105-6110). The sequence of the rat 14mer is KEKWFENEWQG-KNP (SEQ ID NO: 10), the rat 5mer corresponds to NEWQG (SEQ ID NO:11). The human 14mer corresponds to KEQWFGNRWHEGYR (SEQ ID NO:6) and the human 5mer has the following sequence: NRWHE (SEQ ID NO:2). For in vivo imaging experiments the rat 11mer WFE-NEWQGKNP (SEQ ID NO:12), the mouse 11mer WFQNG-WQGKNP (SEQ ID NO:13) and the human 11mer WFGNRWHEGYR (SEQ ID NO:14) were labeled with the fluorescent dye DY681. As a control peptide in the case of rat cells or rat syngeneic models, the human v6 peptide of an identical length as the specific rat v6 peptide was used. In the case of human tumor cells or human orthotopic tumor model, the rat v6 peptide was used as a control. All peptides were produced by Bachem (Bubendorf, Switzerland) or Intavis (Köln, Germany). Lyophilized peptides were resuspended in PBS containing 1% BSA to a stock concentration of 1 mg/ml. Final dilutions were obtained by dilution in PBS.

Lentiviral Transfection of shRNA

The lentivirus system used for silencing Met has already been described (Corso et al., *Oncogene* (2008), 27(5):684-93). Lentiviruses were produced as described elsewhere (Vigna et al., *J. Gene Med.* (2000), 2(5):308-16). Briefly $4 \times 10^6$ 293 T cells (p12-15) were seeded in a 10 cm plate. 24 hours later the packaging vectors VSV-G, PMDL and Rev, the TetR and the lentivirus construct (either Met-shRNA or control-shRNA construct) were mixed and brought to a final volume of 450 µl by addition of TE. 450 µl of a 2.5 M CaCl$_2$ solution was added to this mixture. After vortexing and 5 minutes incubation 500 µl of 2×HBS solution was added drop wise to the DNA-TE-CaCl$_2$ mixture while vortexing at full speed. The precipitate was added to the 293T cells. After 16 h the medium was replaced and fresh medium containing 5 mM sodium butyrate was added. Medium was collected after 24 and 48 hours. Virus containing medium was then added to the target cells BSp73ASs6 (70% confluency) in presence of 8 µg/mL polybrene. 24 hours after infection the medium was replaced and production of shRNA was induced by addition of Doxycylcline to a final concentration of 1 µg/ml. BSp73ASs6 cells transduced with TetR and control-shRNA or Met-shRNA were treated with doxycycline for 72 hours before starting an assay or injection in the animal.

Western Blot Analysis

Serum-starved cells (24 hours) were induced with the growth factor HGF (10 ng/mL) at 37° C. for 5 minutes. Where indicated, the cells were treated with peptides (100 ng/ml) prior to induction at 37° C. for 10 minutes (100 ng/mL CD44v6 peptide or control peptide). Following the induction with HGF, cells were washed with ice-cold phosphate-buffered saline (PBS). To detect activated Met and ERK, cells were lysed in sodium dodecyl sulfate (SDS)—sample buffer containing 100 mM dithiothreitol (DTT), boiled and subjected to western blot analysis using antibodies against phospho-Met and ERK. The loading controls were performed on the same blot after stripping (62.5 mM Tris, pH 6.8, 2% SDS, 0.8% DTT) by probing with the Met respectively Erk antibody. Blots were stained using the enhanced chemiluminescence system (Thermo Fisher Scientific, Schwerte, Germany). Bands in western blot analysis were quantified with the program Image J (National Institutes of Health).

Quantitative Determination of HGF and VEGF in Cell Culture Supernatant

Determination of human HGF and VEGF levels in cell culture medium of L3.6pl cells were performed using the Quantikine Human HGF Immunoassay and Quantikine Human VEGF Immunoassay from Roche (Mannheim, GER) and R&D Systems (Wiesbaden, Germany) For this purpose 3×10$^6$ cells were cultured for 5 days in a 15 cm plate in the presence of the respective peptides as indicated. The supernatant by centrifugation (20 ml) was centrifuged (1200 rpm) and the assay was performed according to manufacturer's instructions.

Animal Experiments

Male athymic nude mice (NCI-nu) were purchased from Harlan (Roβdorf, Germany). BD10 and BDX rats were bred in house. The animals were housed and maintained under specific pathogen-free conditions in facilities approved by the Regierungspräsidium Karlsruhe. All animals were handled according to German regulations for animal experimentation. The animal experiments were approved by the Regierungspräsidium Karlsruhe (35-9185.817G-192/10). Imaging experiments (FIG. 18) were performed in Göttingen were authorized by the Regierungspräsidium (35-9185.817G-106/09).

In the case of the rat syngeneic model, 1×10$^6$ pancreatic cells (BSp73AS and its transfectants) were subcutaneously injected into the right posterior flank of the animals. Tumors developed for four weeks. During this time period animals injected with BSp73ASs6 cells expressing Met-shRNA or control-shRNA received doxycycline in the drinking water. At the end of the experiment, primary tumors were isolated. Lungs and axillary lymph nodes were analyzed. The tissues were incubated for 24 h in a zinc-fixative (0.5 g calcium acetate, 5.0 g zinc acetate, 5.0 g zinc chloride, in 1 L 0.1 M Tris pH 7.4) and embedded in paraffin for further analysis. In case of peptide or antibody treatment tumors developed for one week before the first treatment. Where indicated, animals received 200 µg of peptide or antibody per injection three times per week for four weeks. Tumor growth was monitored weekly using a caliper Animals were killed at day 28 or 30 after start of the treatment.

In the case of the human orthotopic model, L3.6pl pancreatic carcinoma cells (passage 24-26) were suspended in Hank's balanced salt solution (Invitrogen, Karlsruhe, Germany) after trypsinization. The cells were injected orthotopically in the pancreas of male nude mice as described (Bruns C J et al. (1999) Neoplasia 1(1):50-62). Two groups of 15 mice each were injected i.p. 7 days later with either the human v6 peptide respectively rat control peptide (20 µg). For all experiments described and depicted herein either the rat 14mer control peptide or the human 14mer peptide were used. All experiments were then repeated with the rat 5mer control peptide or the human 5mer peptide (N-R-W-H-E, SEQ ID NO: 2). The same results as for the 14mer peptides were observed. The injection was repeated three times per week for 21 days. Two days after the last treatment the animals were killed.

In order to examine the regression of metastases (either BSp73ASs6 or L3.6pl) were implanted as described above. Tumor growth was allowed for three weeks. At that time all animals had developed metastases in the control group. Animals were injected i.p. with 20 µg (L3.6pl orthotopic mouse model: human v6 peptide or rat control peptide) or i.v. with 200 µg (rat syngeneic model: rat v6 peptide or mouse control peptide) of peptides three times per week. Animals were killed 23 days after the start of the peptide treatment.

In Vivo Imaging Using Optix MX2

In vivo imaging of the subcutaneously grown BSp73ASs6 tumors in BD10 or BDX rats was performed using the near infrared fluorescence (NIRF)-imaging system Optix MX2 (ART, Montreal, Canada) as described earlier (Napp et al., *Int J Cancer* (2010), 127:1958-1974). To avoid autofluorescence of fur, rats were shaved around the tumor prior to imaging. Subsequently, animals were anesthetized using 2% isoflurane and gently fixed on the devices' heated plate for the entire time of data acquisition. To reduce fluorescence background, rats were fed with chlorophyll-reduced food (Provimi Kliba AG, Kaiseraugst, Switzerland) for one week prior NIRF imaging. All in vivo analyses were preceded by native scans of animals without any injection of the fluorescent probe. For in vivo analysis, rats were injected with 200 µg DY681-labeled rat v6 11 mer peptide or the human v6 11 mer peptide via the tail vein. Controls were injected with the equal amount of DY681-labeled mouse v6 11mer peptide. The rat 11mer had the sequence WFENEWQGKNP (SEQ ID NO: 12), the mouse 11mer had the sequence WFQNGWQGKNP (SEQ ID NO: 13) and the human 11mer had the sequence WFGNRWHEGYR (SEQ ID NO: 14). All peptides were labeled with the fluorescent dye DY681. Data were acquired at the indicated time after injection of the peptides. For ex vivo monitoring animals were sacrificed after 24 hrs after peptide injection and tumor and organs of interest were scanned ex vivo using Optix MX2.

DY681 fluorescence was measured using excitation at 670 nm in combination with a 700 nm long-pass emission filter. Scans were performed with 1.5 mm raster, photon collection time of 0.5-1 s per scan point and varying laser power. Data sets were analyzed with OptiView (ART).

Fluorescence intensity data are displayed in normalized counts (NC) where the measured fluorescence intensity (counts) was normalized for varying laser power and integration times, allowing comparison of measurements with different settings.

In Vivo Imaging Using Pearl Imager

In vivo imaging of the mice with the L3.6pl tumors was performed using the Pearl™ Imager (LI-COR Biosciences, Bad Homburg, Germany) The system uses two lasers (685 and 785 nm) for excitation and a charge-coupled device detector for signal detection. The laser excitation enables a deep tissue penetration. With the near-infrared detection a high sensitivity due to the reduced tissue auto-fluorescence is achieved. In order to standardize the images we made use of the Pearl Cam Software. The animals were fed with chlorophyll-reduced food to reduce the fluorescence background one week before imaging (Regime 210, safe-diets, Augy, France). Prior to imaging the mice were anesthetized with 2.0% isoflurane. Animals were placed on the heated plate of the imager and continuous delivery of isoflurane was achieved through a nose cone in the imaging drawer. Images were captured at white light, 700 and 800 nm Animals were imaged prior to i.v. peptide injection and 24 h after injection with either DY681-labeled human v6 peptide or DY681-labeled rat v6 peptide as control Immediately after each imaging session animals were killed, tumor, liver and spleen isolated and scanned ex vivo at white light, 700 and 800 nm.

Immunofluorescence

ASs6 or L3.6pl cells were seeded at 5,000 cells/well of a Lab-TekR Chamber Slide™ (Nunc, Napierville, Ill., USA). On the following day the cells were washed with cold PBS and fixed with 4% Formalin for 30 min at RT. Unspecific binding was blocked with 1% BSA in PBS for 1 hour at RT. The cells were incubated for 1 hour with the DY681-labeled peptides. After three washing steps with PBS the cover slips were mounted with Fluorescence Mounting Medium (Dako, Glostrup, Denmark) and the immunofluorescence was measured by a laser scanning confocal microscope Leica TCS2 SP2 (Exton, Pa., USA) and processed using Leica confocal software. A 20× objective was used for imaging.

Histology

For histomorphological analysis paraffin-embedded sections of lungs were stained with hematoxylin and eosin and periodic acid-Schiff (H&E or PAS). Serial sections of the whole tissue blocks were examined by analyzing slices every 20 µm; in each slice, the presence and the extension of the metastatic deposit was assessed, according to the procedure routinely used by pathologists to evaluate the presence of micrometastases.

Immunohistological and Immunofluorescence Analysis

7 µm thick paraffin sections were deparaffinized and rehydrated. For P-Met staining antigen unmasking was achieved by boiling the slides in 1 mM EDTA pH 8.0 followed by incubation for 15 minutes at a sub-boiling temperature, for CD31 staining the sections were treated with Proteinase K (8 µg/ml) for 10 mM at 37° C. For immunofluorescence staining of P-Met, unspecific binding was blocked with 5% goat serum (DAKO, Glostrup, Denmark) (diluted in 1×PBS/0.3% Triton X-100) for 60 minutes. In the case of immunohistochemistry, endogenous peroxidases were at first blocked with 3% H2O2 in PBS followed by incubation with biotin blocking system (Dako, Glostrup, Denmark) and then unspecific binding was inhibited by incubation with 5% FCS in PBS was used for blocking. The sections were incubated with the P-Met antibody (D26, dilution 1:50 in 1×PBS/1% BSA/0.3% Triton X-100), Met antibody (C-28, dilution 1:50), GFP antibody (sc-101525, dilution 1:50) or CD31 antibody (5 µg/ml) over night or VFF18 (5 µg/ml) o/n at 4° C. After washing in PBS the sections were incubated with Alexa Fluor R 546 goat anti-rabbit (in case of immunofluorescence P-Met and Met staining, dilution 1:500) or a biotinylated secondary antibody (for immunohistochemical stainings rabbit anti-rat antibody for VFF18 and CD31, goat anti-rabbit for P-Met, cleaved Caspase-3 and cleaved Caspase-8 and rabbit anti-mouse for GFP, dilution 1:500) for 45 minutes. For DAB staining the sections were treated with a streptavidin-peroxidase conjugate (Dako, Glostrup, Denmark) and developed with DAB (3,3'-diaminobenzidine) substrate system (3,3'-diaminobenzidine; Biozol, Eching, Germany) For immunofluorescence DAPI was used for nuclear staining.

2. Results

The Co-Receptor Function of CD44v6 for Met is the Decisive Step for Metastatic Spreading of Rat Pancreatic Tumor Cells To investigate whether the co-receptor function of CD44v6 for the Met receptor is the decisive step for the metastatic spreading of tumor cells it was first examined whether a CD44 isoform containing exclusively the exon v6 or all the variant exons v1-10 included in the CD44v1-10 isoform would confer metastatic potential to the rat BSp73AS cells. In these cells, Met cannot be induced by HGF unless a CD44v6 containing isoform is transfected (FIG. 16A). Removal of exon v6 e.g. in CD44v1-10Δv6 impaired the activation of Met by HGF (FIG. 16A).

The parental BSp73AS cells and cells stably transfected with the constructs mentioned above (CD44v6, CD44v1-10 and CD44v1-10Δv6) were subcutaneously injected into isogenic rats. In all animals primary tumors were palpable already after one week. In the case of cells transfected with CD44v6 or CD44v1-10 the axillary lymph nodes of the corresponding animals were enlarged already two weeks after injection and the animals were killed after six weeks. Histomorphological examination of the lungs and lymph nodes revealed that all rats bearing CD44v6 or CD44v1-10 expressing tumors developed nodal and intrapulmonary metastases. In contrast, the parental cells or the cells transfected with CD44v1-10Δv6 gave rise to primary tumors but not to metastasis, neither in lymph nodes nor in the lungs (FIG. 16B and Table 1). No micrometastasis was detected in the lungs of these animals (Table 1). Thus, CD44 isoforms such as CD44v6, that allow Met activation, also confer metastatic propensity to BSp73AS cells.

Next, BSp73ASs6 cells (BSp73AS cells expressing the CD44v6 isoform in addition to CD44s) were stably transfected with lentivirus expressing Met shRNA sequences. It was confirmed that the cells do not express Met (FIG. 16A, last two lanes). Then, these cells (or cells infected with lentivirus expressing control sh-RNA sequences) were injected into syngeneic animals. The animals were examined six weeks after injection. All animals developed primary tumors (Table 1). However, Met activation was only observed in the primary tumors of cells infected with control sh-RNA expressing lentivirus, but not in primary tumors expressing Met sh-RNA (FIG. 16C). Furthermore, when Met expression was abolished no metastasis nor micrometastasis was detected neither in lung nor in the axillary lymph nodes (FIG. 16B, Table 1) demonstrating the importance of Met for the metastatic process. From these data, it can be concluded that both CD44v6 and Met are required for metastatic spreading of BSp73AS cells.

Next it was examined whether the rat counterparts to a peptide of SEQ ID NO: 2 (human CD44v6 5mer peptide) or SEQ ID NO: 6 (human CD44v6 14mer peptide) that interferes with the co-receptor function, also inhibit metastasis formation. Rat peptides had the sequences KEKWFENEWQGKNP (SEQ ID NO: 10) and NEWQG (SEQ ID NO: 11). BSp73ASs6 cells were subcutaneously injected into syngeneic rats and rat CD44v6 peptides of SEQ ID NO: 10 or SEQ ID NO: 11 (or mouse control peptides) or the CD44v6 antibody (or IgGs as a control) were injected intra-tumoral or intravenously three times a week. Both, treatment with the v6 specific antibody or with the v6 specific peptide completely inhibited metastasis (FIG. 17B, Table 2). In lung sections from animals treated with the CD44v6 peptide, no metastasis nor micro-metastasis could be detected upon histological analysis using PAS and H&E staining (FIG. 17C and Table 2). This is in clear contrast with the results obtained from animals treated with the control peptide (or control IgG) where numerous metastases were detected in the lungs (FIG. 17B, C). Interestingly, the outgrowth of primary tumors was not influenced by either treatment (FIG. 17D). This is compatible with the fact that also BSp73AS cells or BSp73ASv1-10Δv6 cells can induce the formation of primary tumors similarly to the v6 transfectants.

Taken together the experiments suggest that the co-receptor function of CD44v6 for Met is the decisive step for metastatic spreading in the rat pancreatic tumor cell system and that it does not account for the outgrowth of the primary tumor.

Specific Binding of a CD44v6 Peptide to Tumor Cells In Vivo

In order to test the specificity of the binding of CD44v6 peptides to the tumor site and to the metastases and to estimate the binding kinetics in vivo, near infrared fluorescence (NIRF) imaging with the Optix MX2 was. For this purpose two CD44v6 peptides were labeled with the fluorophore DY681: a rat specific one, rv6 pep Dy681 and a mouse specific one, mv6 pep Dy681, as a control. In vitro testing showed that indeed, only the labeled rat peptide but not the mouse peptide inhibited Met activation as was demonstrated in FIG. 18A right side. Furthermore, the DY681-labeled rat v6 peptide, but not the DY681-labeled mouse v6 peptide bound to BSp73ASs6 cells in tissue culture (FIG. 18A left side).

For in vivo experiments, BSp73ASs6 cells were injected subcutaneously into syngeneic rats. Three weeks later, they received either of the labeled v6 peptides by injection into the tail vain. The accumulation of the fluorescence was measured in the tumor region by Optix MX2 at the indicated time points. Prior to intravenous (i.v.) injection of Dy681-labeled peptides mice were natively scanned in order to measure levels of autofluorescence background. Then, in vivo binding kinetics of the Dy681-labeled v6 peptides to the subcutaneous tumors were determined. As shown in a series of representative NIRF images taken 1, 2, 3 and 7 days after peptide injection, high fluorescence intensity was detected over the tumor area for at least 2 days in vivo, with a maximum at 1 day. Injection of the control peptide m6 pep Dy681 did not result in any fluorescent signals over the tumor area (FIG. 18D).

To specifically examine the distribution of the v6 peptides in the tumor and also in the lungs, both tissues were excised 24 h after peptide injection and examined ex vivo by Optix MX2 (FIG. 18C). Fluorescence intensities could only be detected in tumors and in specific areas of the lungs scanned ex vivo and excised from mice that received rv6 pep Dy681, but not in tumors and lungs from all control rats previously injected with mv6 pep Dy681 (FIG. 18C). These results confirmed the in vivo observation that the rat peptide binds specifically to the subcutaneous rat pancreatic tumor and furthermore even suggest in vivo binding to metastases. Indeed, histological analysis revealed the presence of metastases in the lungs of all animals.

Metastasis Formation of Human Pancreatic Tumor Cells is Inhibited by a Human CD44v6 Peptide of SEQ ID NO: 2 or SEQ ID NO:6

To expand the studies to human pancreatic tumors, the highly metastatic human pancreatic carcinoma cells L3.6pl (Bruns, et al. *Neoplasia* (1999), 1(1):50-62) were investigated. These cells originate from the COLO 375 cells that have been passaged several times in the liver and the pancreas, a step that rendered them more and more metastatic. It was confirmed that Met is dependent on CD44v6 for its activation and signaling in these cells (FIG. 19A). The L3.6pl cells were treated with HGF in the presence or absence of a human v6 peptide of SEQ ID NO: 2 or SEQ ID NO:6 and Met activation and downstream signaling to ERK was measured. Phosphorylation of both Met and ERK was inhibited by the human v6 peptide. Treatment with a corresponding rat v6 peptide (ctrl peptide, SEQ ID NO: 10 or 11) had no influence on receptor activation and signal transduction (FIG. 19A).

To test the effect of the peptide on tumor growth and metastasis formation the L3.6pl cells were orthotopically injected into the pancreas of immunosuppressed mice (NCI-nu). These mice developed primary tumors and showed numerous metastases in the liver after four weeks. The primary tumor expresses a high amount of CD44v6 (FIG. 19B). Intraperitoneal (i.p.) injection of the human-specific peptide three times per week for three weeks completely repressed Met activation as shown by the immunofluorescence staining for phospho-Met and Met in the tumor (FIG. 19C). These data demonstrate that the peptide interferes with the co-receptor function of CD44v6 for Met and abrogates Met phosphorylation in vivo. Since the activation of Met is species-specific and the human Met receptor can only be activated by human HGF this result suggests that the L3.6pl cells produce their own HGF. Interestingly, in contrast to the rat system the outgrowth of the primary tumor in the pancreas was strongly repressed by the human v6 peptide (FIG. 19D top). The outgrowth of the primary tumor in the pancreas was also strongly repressed (FIG. 19D bottom). The rat-specific peptide (ctrl peptide) had neither influence on metastasis formation nor on growth of the primary tumor (FIG. 19D). This result suggests that the L3.6pl cells produce their own HGF. Indeed, human HGF in a concentration of 3375 pg/ml was detected in the supernatant (see Material and Methods) after 5 days of culture (data not shown).

It was observed that the outgrowth of the primary tumor was retarded upon inhibition of tumor angiogenesis with a murine-specific v6 peptide. Here it is shown that the treatment with the human peptide also decreased angiogenesis as exemplified by a reduced vessel number and vessel size in the v6 peptide-treated tumors. The decreased angiogenesis explains the reduced tumor volume (FIG. 19D, E). Since the v6 peptides act in a species-specific manner, the inhibition of angiogenesis cannot be due to an effect on the murine endothelial cells but rather to an inhibition of VEGF production by human pancreatic carcinoma cells. Indeed, the human L3.6pl cells produce hVEGF, a secretion that can be blocked by treatment with the human v6 peptide (FIG. 19F). The most striking observation was that the human-specific peptide completely inhibited metastasis formation within the liver (FIG. 19G). The rat-specific peptide (ctrl peptide) had no influence on metastasis formation or on growth of the primary tumor (FIG. 19C-G).

Then, the specificity of binding of the human CD44v6 peptide to the tumor in vivo was examined using the small animal imaging system Pearl Impulse. The human labeled peptide but not the rat peptide inhibited Met activation in L3.6pl cells (FIG. 20A right side) and bound to these cells in cell culture (FIG. 20A left side). In vivo the fluorescently labeled (DY 681) human peptide accumulated specifically in the tumor induced by orthotopically injected L3.6pl cells (FIG. 20B). No fluorescence was detected in animals that were treated with a control peptide. Furthermore, no signal was observed in animals that received no peptide whether or not they had developed a tumor (FIG. 20B). Ex vivo analysis of organs isolated from animals treated with the labeled human v6 peptide allowed detection of binding not only to primary tumors but also to areas of the liver most probably corresponding to metastases (FIG. 20C). Thus these experiments reveal that the CD44v6 peptides not only target the primary tumors but also distant metastases.

Already Established Metastases are Eliminated by CD44v6 Peptides

The specific binding of the CD44v6 peptides to specific areas of the lungs in the rat system and of the liver in the human model raises the question whether these peptides might have an effect on already established metastases. In the experiments described in FIGS. 17 and 19 the peptides were applied early after injection of the tumor cells and repressed completely the establishment of metastases. In order to measure the effect of the CD44v6 peptide on already established metastases, other experimental settings were used. BSp73ASs6 cells were injected subcutaneously into syngeneic rats and L3.6pl cells orthotopically into male nude mice and allowed to grow for 3 weeks. At that time all animals from the control group had developed metastases (Table 3) suggesting that this was also the case in the groups used for peptide treatment. The animals were then treated either with the species-specific CD44v6 peptide or with the control peptide (mouse for the rat system and rat for the human system) twice per week for another three weeks (Scheme in FIG. 21A) and then tested for the presence of metastases. At the end of the experiments metastases could be detected in all animals treated with the control peptide (Table 3, FIG. 21B for the BSp73ASs6 cells, Table 3, FIG. 21C for L3.6pl cells) whereas animals treated with the species-specific CD44v6 peptides were free of metastasis. Thus, already established metastases are eliminated by treatment with the CD44v6 peptides.

One hypothesis for the disappearance of metastases is that the peptides induce apoptosis of CD44v6-expressing metastatic cells in the secondary organs. In order to test this hypothesis, the experiment described above using the BSp73ASs6 cells was repeated. The cells were injected subcutaneously in syngeneic rats and the tumor was allowed to develop for three weeks. After that time the animals were separated in two groups of 10 animals that were injected either with the specific rat CD44v6 peptide or with the control peptide (mouse) every second day. One day following each injection of the peptide, the lungs of one animal were removed and apoptosis was measured using an antibody that detects the cleaved form of Caspase 3. Apoptotic cells were detected as early as three days after the first injection of the peptides in the tumor areas of animals treated with the CD44v6 peptide. No apoptosis at all was detected in the animals injected with the control peptide (FIG. 22). A maximum of apoptosis was measured eight days after the first injection of the CD44v6 peptides. Twelve days after injection of the CD44v6 peptide, less apoptosis was observed. At day twenty-two, no metastasis could be detected anymore in animals treated with the CD44v6 peptide whereas metastatic spreading was evident in the lungs of control animals (FIG. 22). From these experiments, it is concluded that the CD44v6 peptide induces apoptosis of metastatic cells.

To discriminate whether the intrinsic pathway characterized by the release of mitochondrial proteins or the extrinsic pathway activated by ligand-bound death receptors for apoptosis was induced by the v6 peptide the expression of cleaved caspase-8 in the metastases treated with the v6 peptide was investigated. A kinetic of activation of caspase-8 similar to the one obtained for caspase-3 in the lungs of the v6 peptide treated animals was observed. From these experiments we conclude that the CD44v6 peptide induces apoptosis of metastatic cells via the extrinsic apoptotic pathway.

Example 3

Pegylated CD44v6 Peptides Inhibit HGF Dependent CD44v6 Mediated Signaling

1. Material and Methods
Synthesis of Pegylated Peptides

Peptide synthesis was performed on an Applied Biosystems automated peptide synthesizer (model 433A) and the peptides were purified by preparative HPLC.

Peptides of sequences NEWQG (SEQ ID NO: 11) and a control peptide NAAAG (SEQ ID NO: 15) were synthesized. Crude and purified products were characterized by LC coupled to a mass spectrometer (μTOF LCMS from Bruker Daltonics-Bremen, Germany).

Peptide synthesis was performed using standard Fmoc solid phase peptide synthesis protocols (see e.g. Fields et al., *Int J Pept Protein Res.* (1990), 35, 161-214, Maisch et al., *J Am Chem Sco.* (2009), 131, 15596-15597, Strandberg et al., *Biophys J.* (2006), 90, 1676-1686, and Wadhwani et al., *J Org Chem.* (2006), 71, 55-61). Fmoc deprotection was done with 20-22% piperidine in NMP. Coupling was performed using a mixture of Fmoc-amino acid:HOBt: HBTU: DIEA (4:4:3.9:8) in DMF. Peptides were cleaved from the solid support using a mixture of TFA:$H_2O$:TIS (93.5:2.5:4). The cleavage reagents were removed under $N_2$-flow, and the labeled peptides were precipitated using diethyl ether.

Preparative HPLC was performed on a reversed phase C18 column (4 6 mm×240 mm) at 35° C. using a Jasco-HPLC system (Tokyo, Japan) fitted with a diode array detector. Epimeric peptides were separated using acetonitrile/water gradients 0.1% TFA.

All amino acids were purchased from Novabiochem (Schwalbach, Germany). The MeO-PEG-COOH (molecular weight 750 Da and 2000 Da) and the coupling reagents (HBTU, HCTU) and DIEA were from his Biotech (Marktredwitz, Germany), and solvents and other reagents were from VWR-Merck (Bruchsal, Germany).

The following compounds were synthesized:
PEG-control peptide: PEG-NAAAG (PEG-SEQ ID NO: 15),
PEG-rat CD44v6 peptide: PEG-NEWQG (PEG-SEQ ID NO: 11)
Palmitic-NH-PEG-CONH-control peptide
Palmitic-NH-PEG-CONH-rat CD44V6 peptide Palmitic-NH-PEG-CONH-control peptide and Palmitic-NH-PEG-CONH-rat-CD44V6 peptide were synthesized by first coupling Fmoc-NH-PEG-COOH molecular weight 3000 Da to either SEQ ID NO: 11 or SEQ ID NO: 15. Then the pegylated peptides were reacted with palmitic acid.

Activation Assays

The PEG-control peptide and PEG-rat CD44v6 peptide were compared for their ability to block HGF induced activation of the receptor tyrosine kinase Met and ERK.

Rat pancreatic cancer cells BSp73ASs6 (also designated Ass6) were incubated for 10 min at 37° C. with either ctrl-peptides (SEQ ID NO: 15), non-pegylated v6-peptides (SEQ ID NO: 11) and increasing concentrations of the pegylated peptides, namely PEG-rat control peptide and PEG-rat CD44v6 peptide, before induction with HGF (10 ng/ml; 5 min at 37° C.).

Activation of ERK and Met was determined by standard SDS and Western Blotting techniques using a phospho-Met and phospho-Erk specific antibody (phospho-Met clone D16 cell signaling, phospho-Erk p42/44 cell signaling)

Cellular Assays

A scatter assay was performed additionally. HT29 colon cancer cells were grown in medium containing 10% FCS. One day after seeding, the cells were starved. On the third day, the cells were induced with HGF (10 ng/ml) and pre-incubated with either no peptide, ctrl-peptides (SEQ ID NO: 15), non-pegylated v6-peptides (SEQ ID NO: 11) or the pegylated peptides, namely PEG-rat control peptide and PEG-rat CD44v6 peptide.

2. Results

Example 4

Breast Cancer 4.1 Background

Different members of the ErbB family of RTKs are either overexpressed or mutated in a wide variety of cancers. For example, high ErbB1 expression was found in a majority of carcinomas including mammary carcinomas and amplification of the ErbB2 gene can be found in 20-30% of metastatic breast cancer lesions. The tumorigenicity of these breast cancer types depends on the constitutive activation of the ErbB receptors.

It was shown that CD44v6 enables the activation of the ErbB receptors through EGF in several breast cancer cell lines. CD44v6 could therefore play a role in breast cancer types that are dependent on EGF-based ErbB activation for their tumorigenicity. And indeed, the evaluation of 100 primary invasive breast tumors and 18 lymph node metastases connected the expression of CD44v6 with tumorigenity. The presence of these CD44 variants correlates with poor survival. Two more recent studies came to similar results.

However, there are conflicting data concerning the role of CD44v6 in breast cancer. A study, evaluating 109 patients with stage II breast neoplasia for example did not associate CD44v6 expression with disease free survival or overall survival at all. An explanation for the conflicting studies could be that CD44v6 does not act as a co-receptor for all breast cancer types. In cancer types where the activation of the ErbB-receptors is mediated by TGF-α for example, CD44v6 would not be needed as a co-receptor as it could be shown that activation via TGF-α is independent of CD44v6.

4.2 Effect of the CD44v6 14Mer

The effect of the CD44v6 14mer was tested in a syngeneic mouse model by orthotopic injection of the murine mammary carcinoma cells 4T1. 4T1 cells were originally derived from a spontaneously arising BALB/c mammary tumor. When introduced orthotopically, 4T1 cells grow rapidly at the primary site and form metastases in the lung and the lymph nodes within a period of 3-6 weeks. The tumor growth and metastatic spreading of 4T1 cells in BALB/c mice very closely mimics human breast cancer stage IV.

The 4T1 cells were injected orthotopically into the 6th mammary fat pad. Two groups of 5 animals each with the implanted tumor cells were then used for the experiment. One group was treated with the v6 14mer peptide, one with a control (rat) peptide. The injection of the peptide was performed 3 times per week and planned for three to four weeks but had to be stopped after two weeks as the control group suffered from large tumors.

Figure 1:
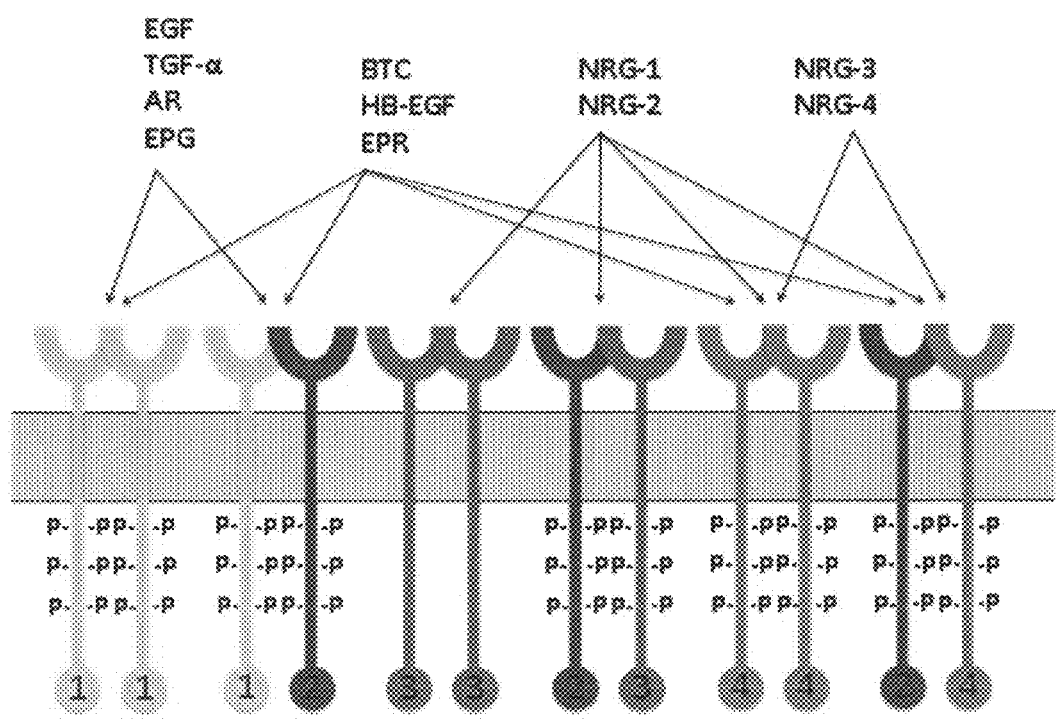
Figure 2:
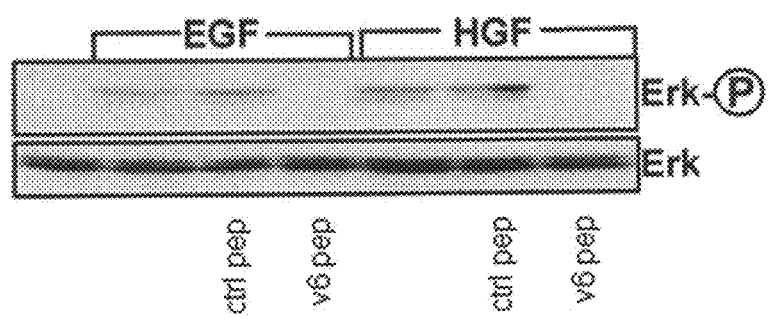
Figure 3:
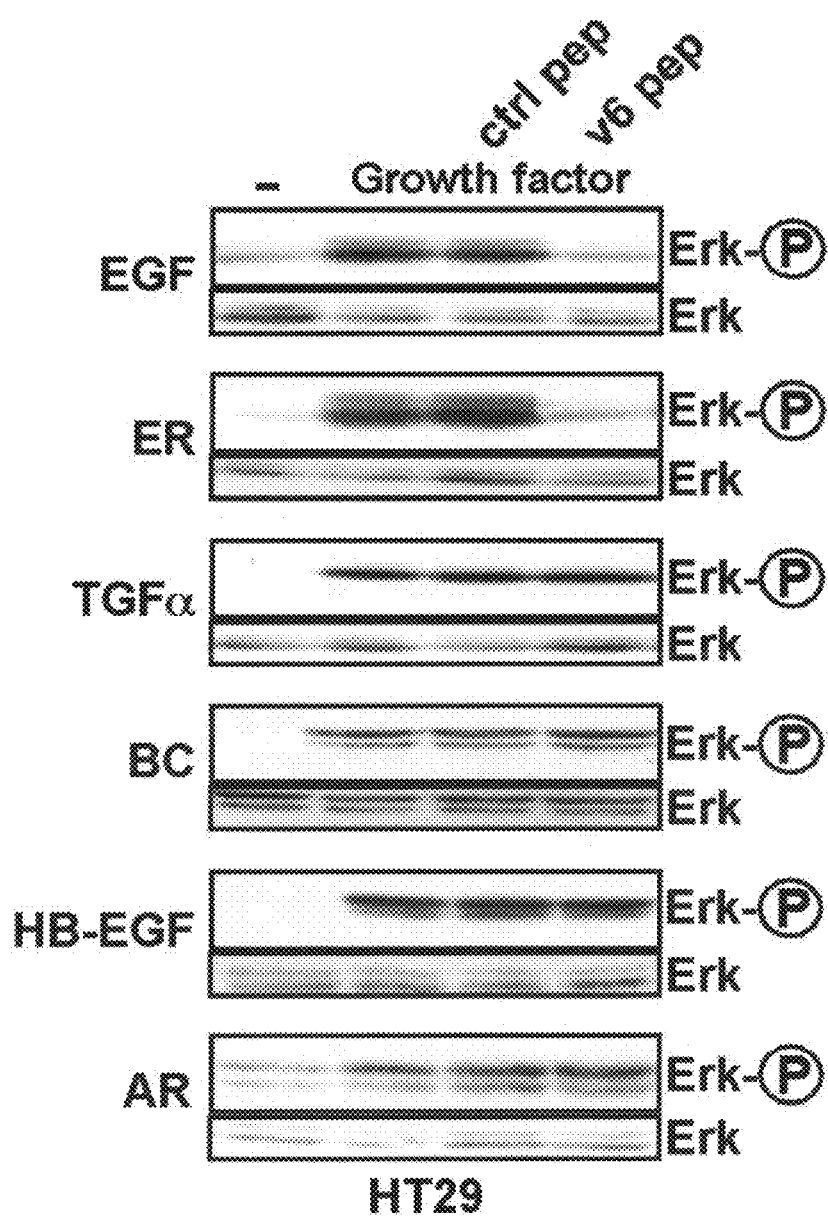
Figure 5:
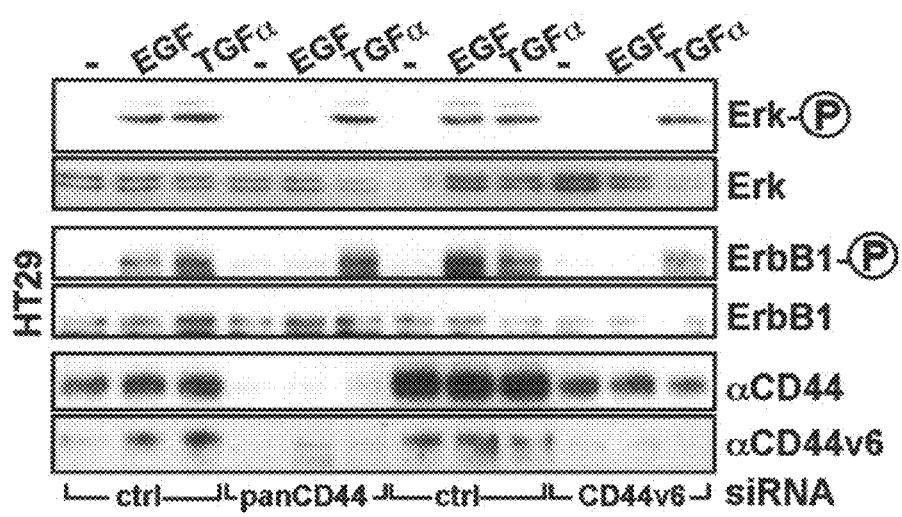
Figure 6:
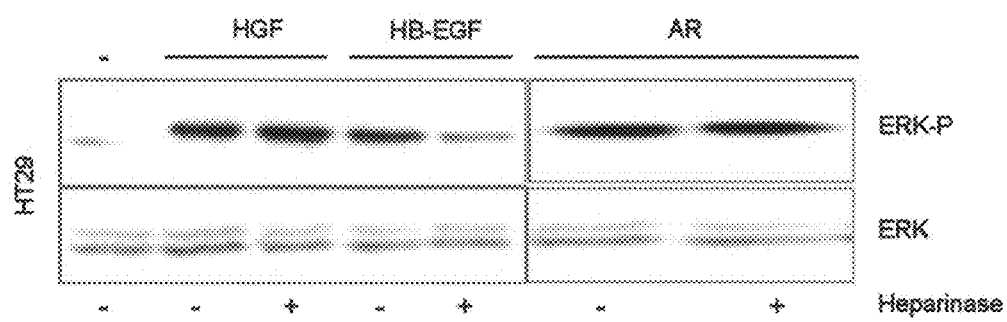
Figure 7:
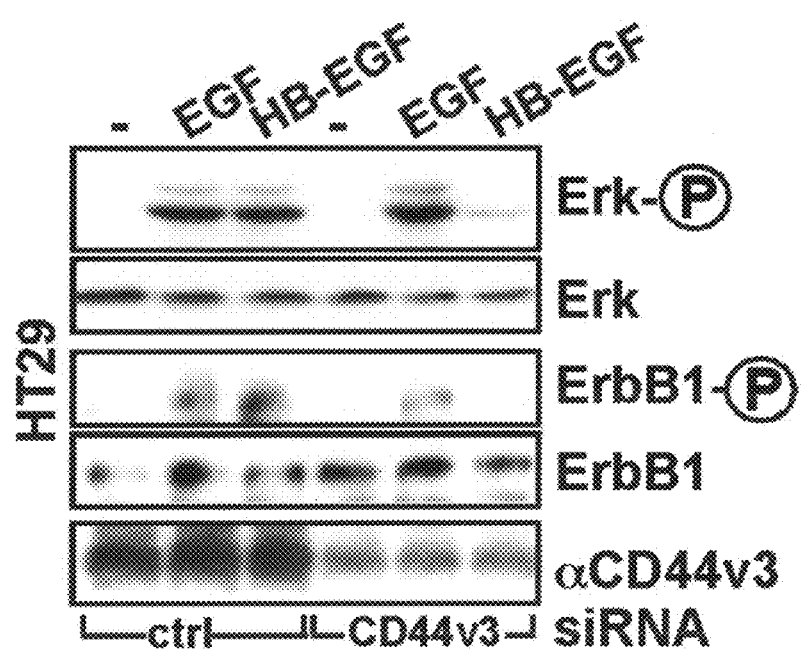
Figure 8:
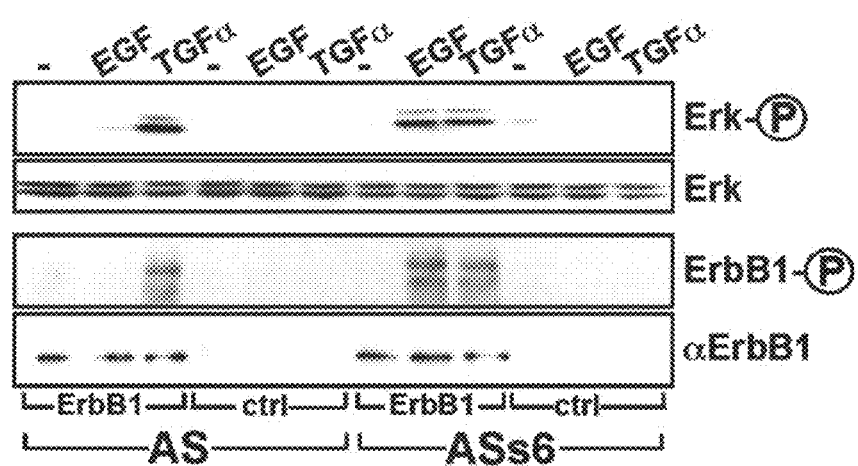
Figure 9:
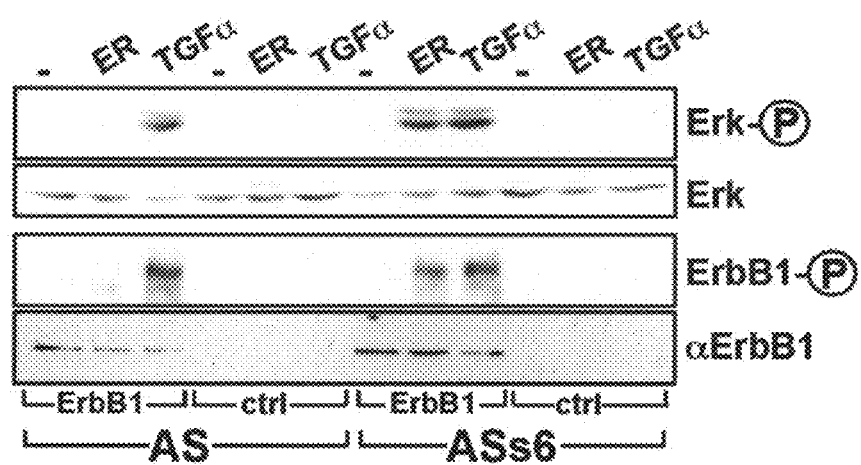
Figure 10:
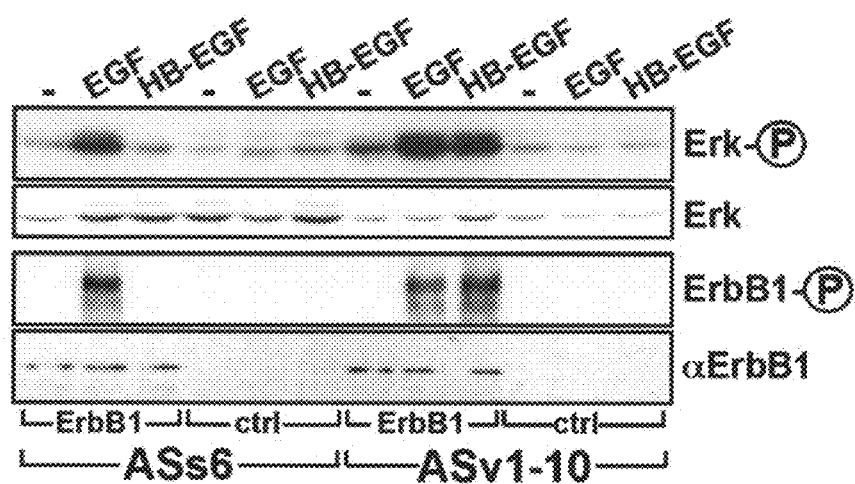
Figure 11:
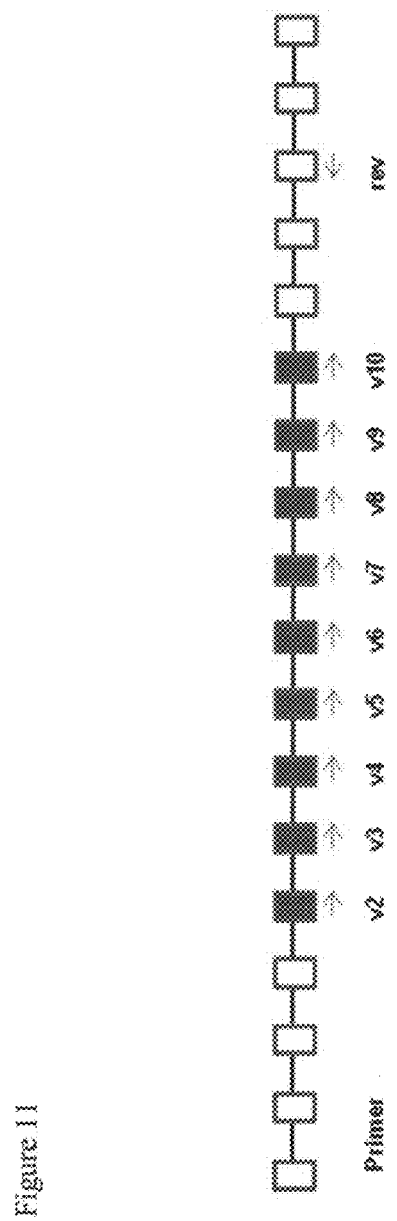
Figure 13:
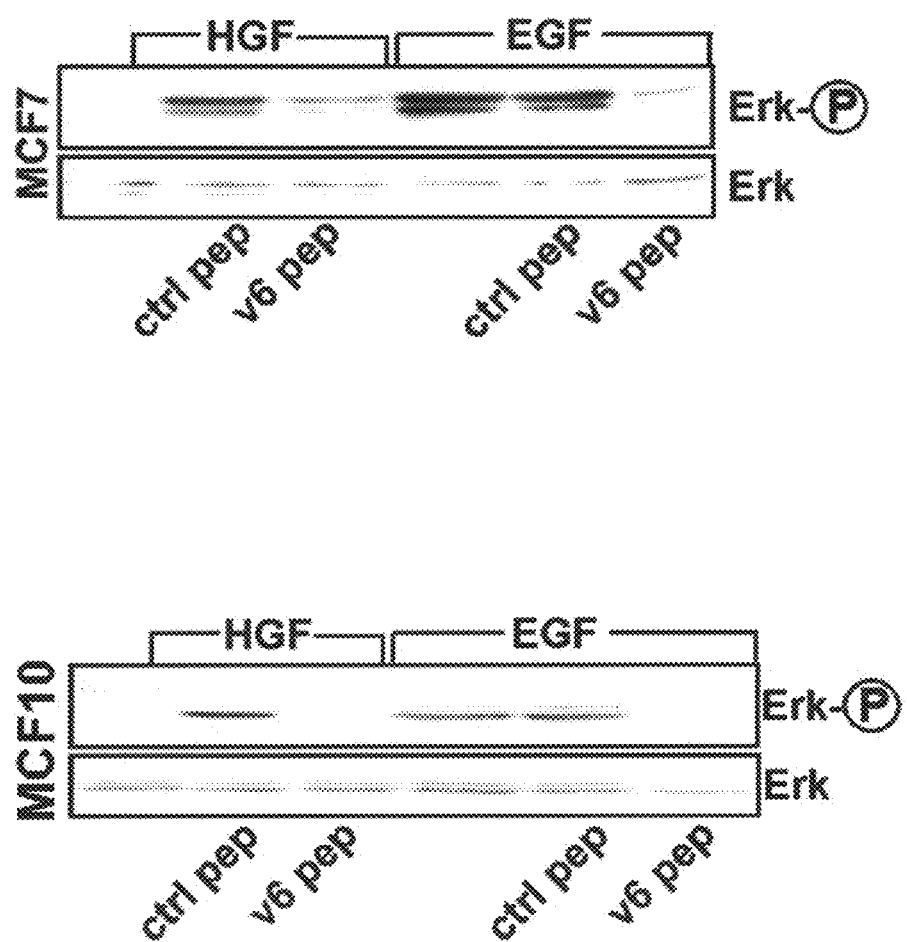
Figure 14:
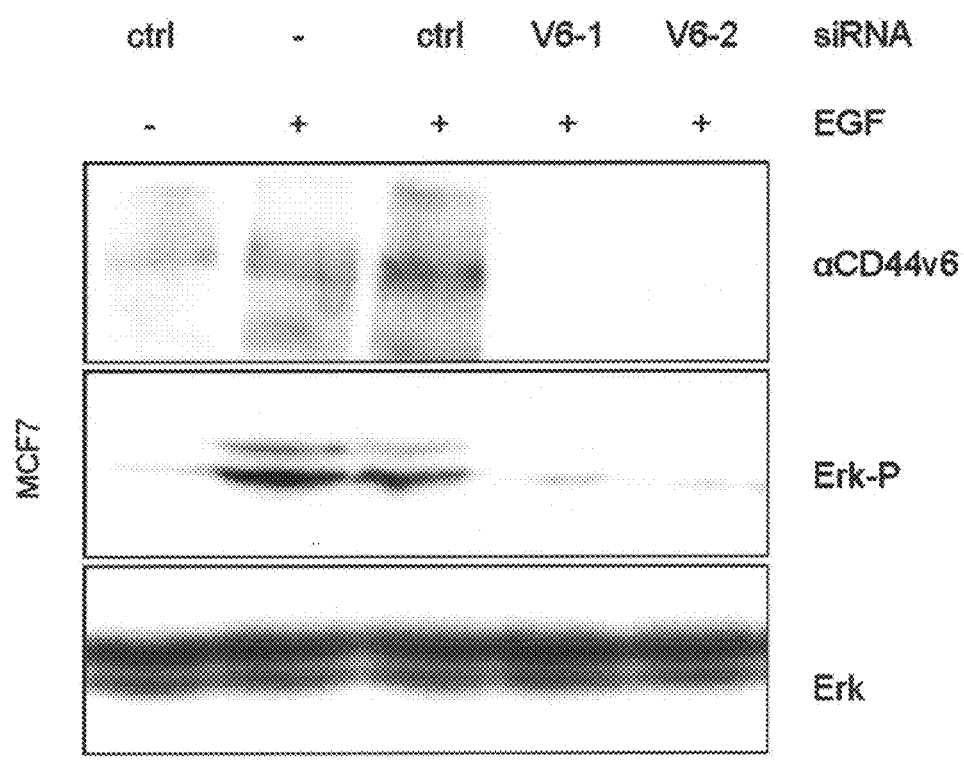
Figure 15:
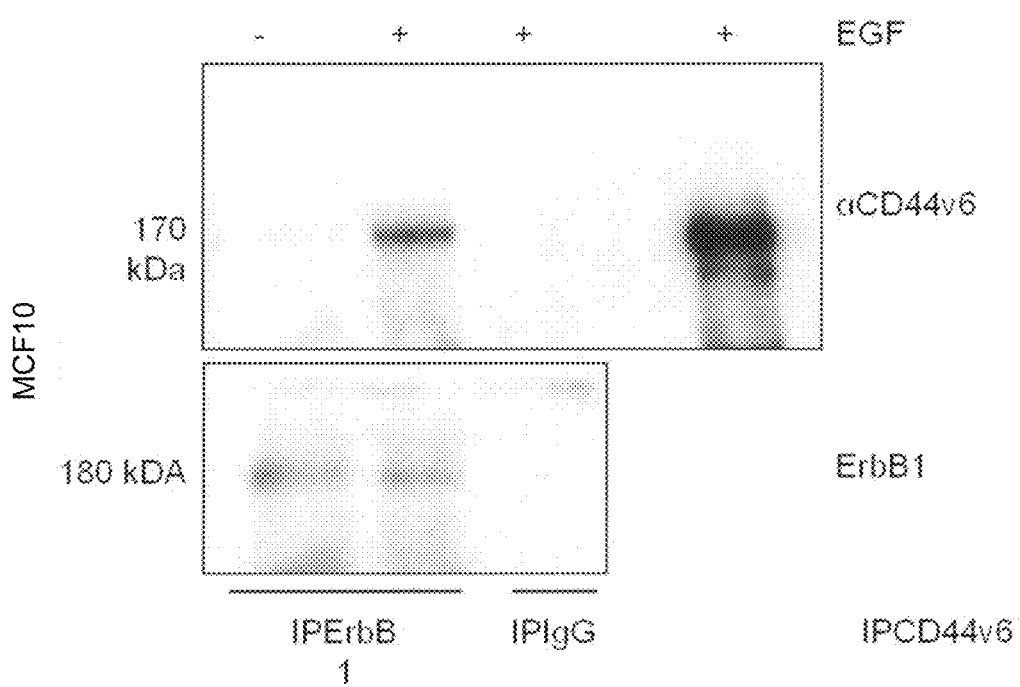
Figure 16:
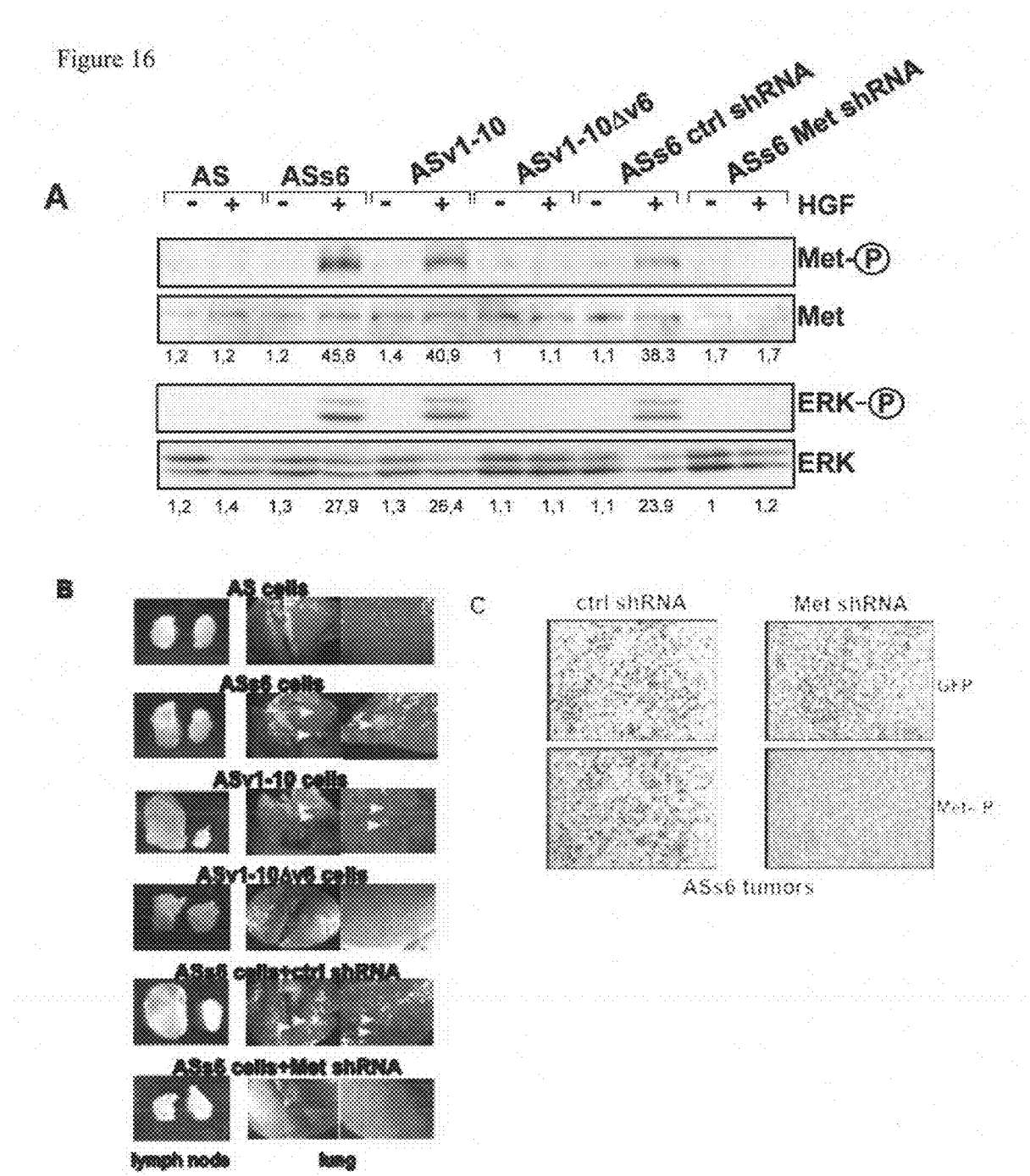
Figure 17:
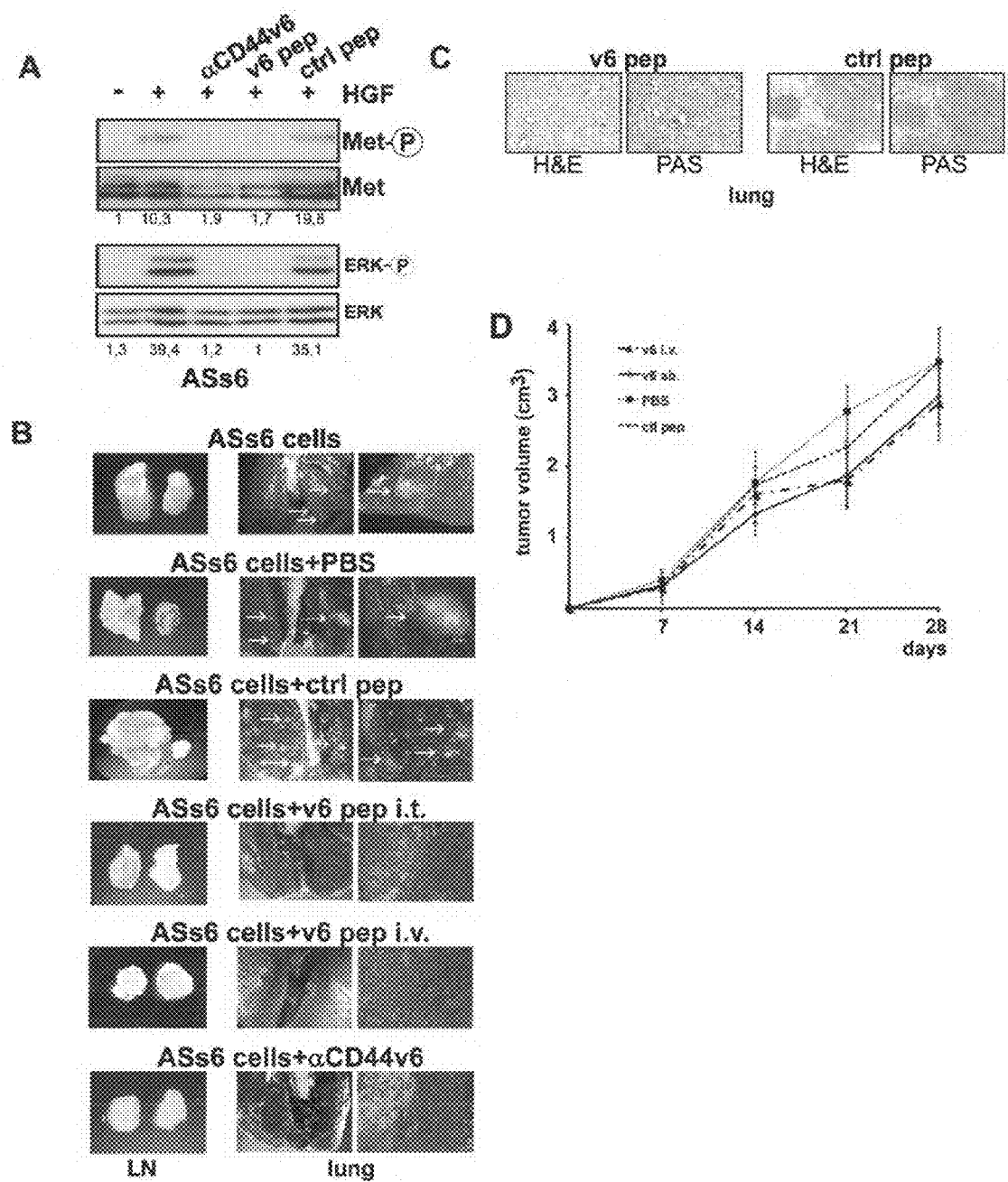
Figure 18:
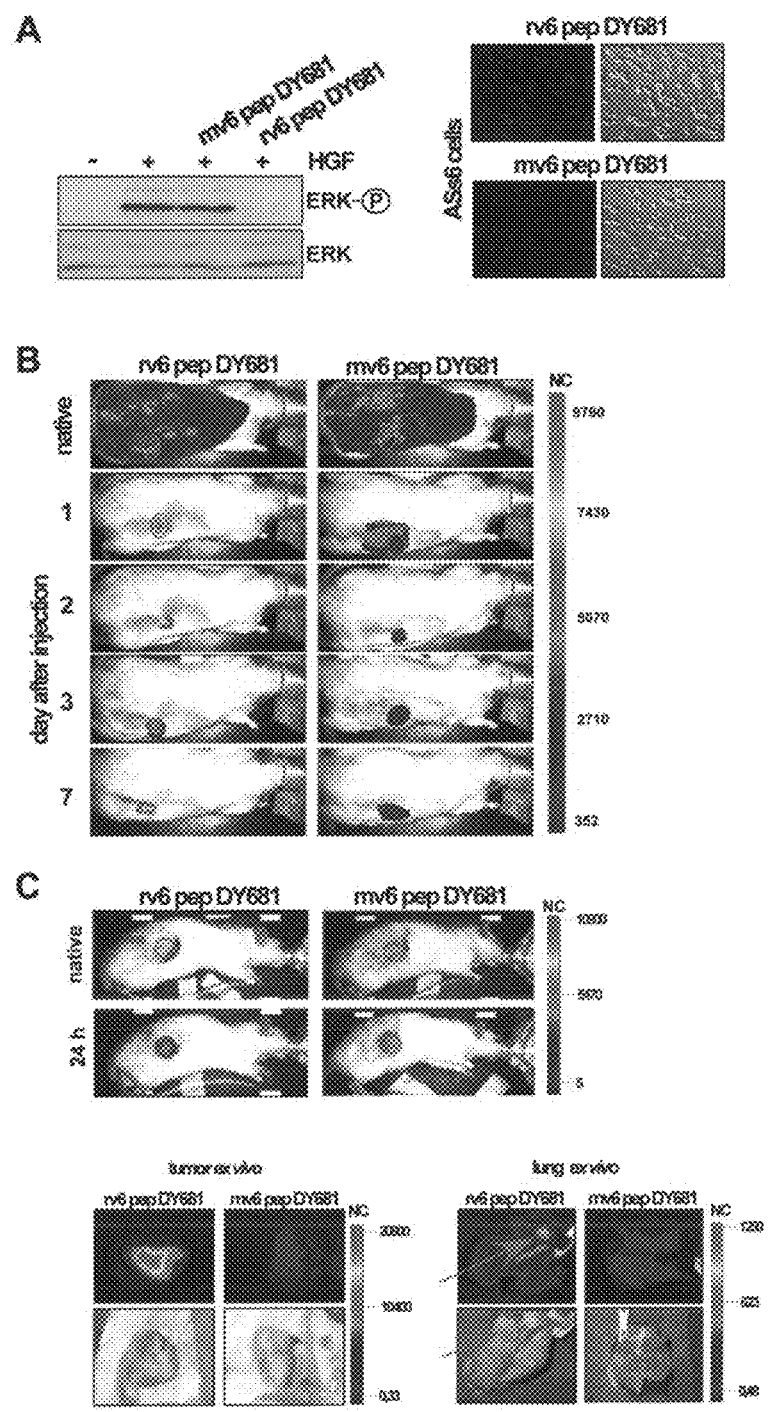
Figure 19:
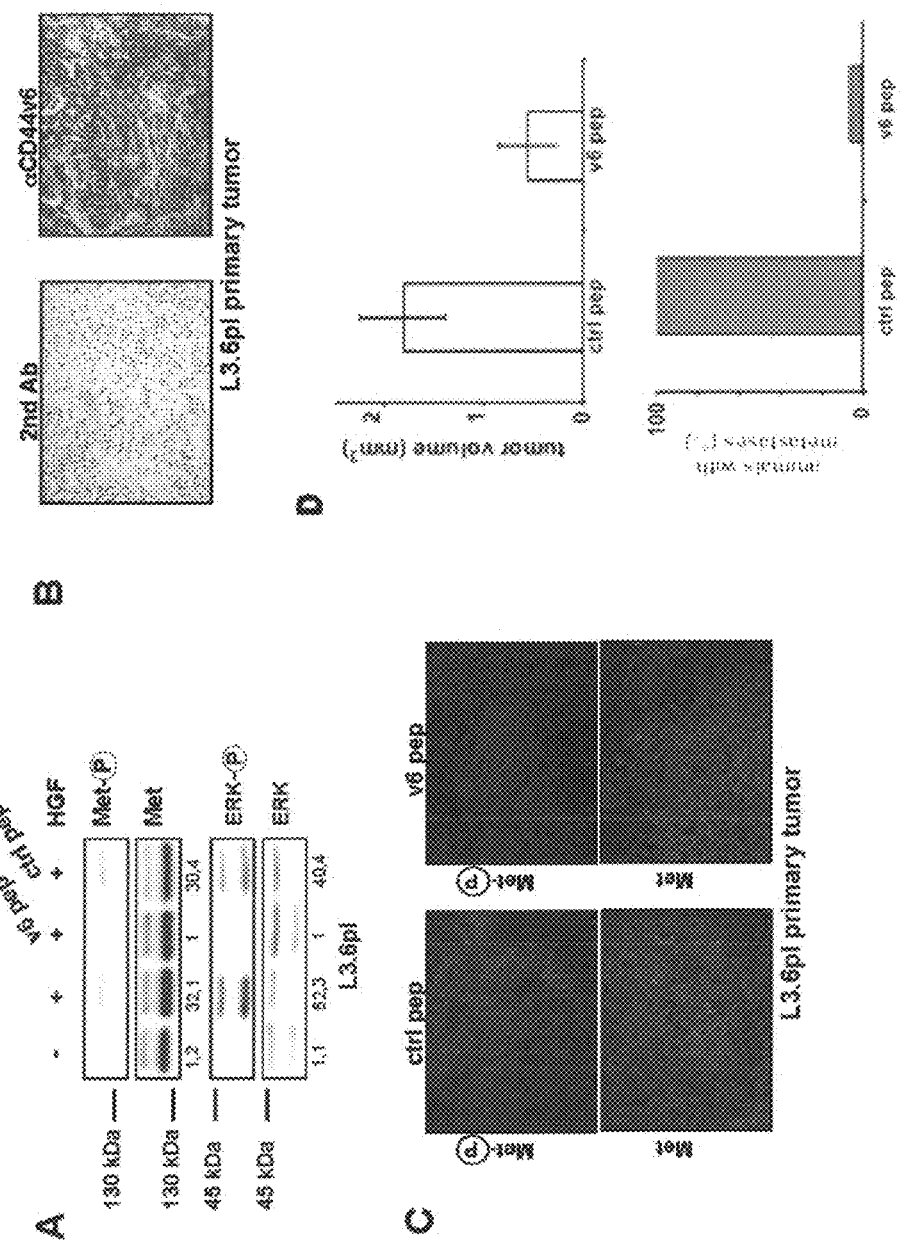
Figure 19:
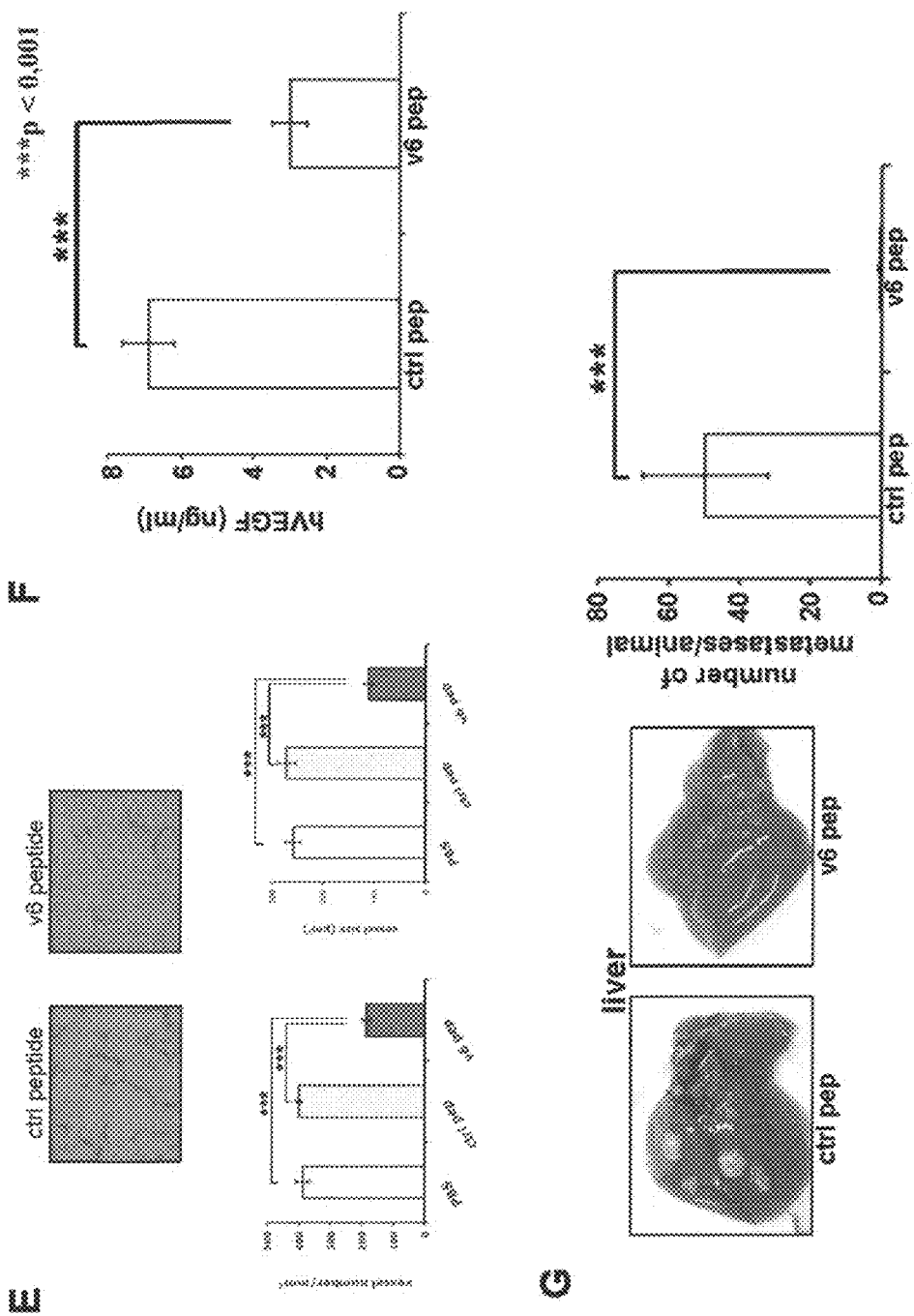
Figure 20:
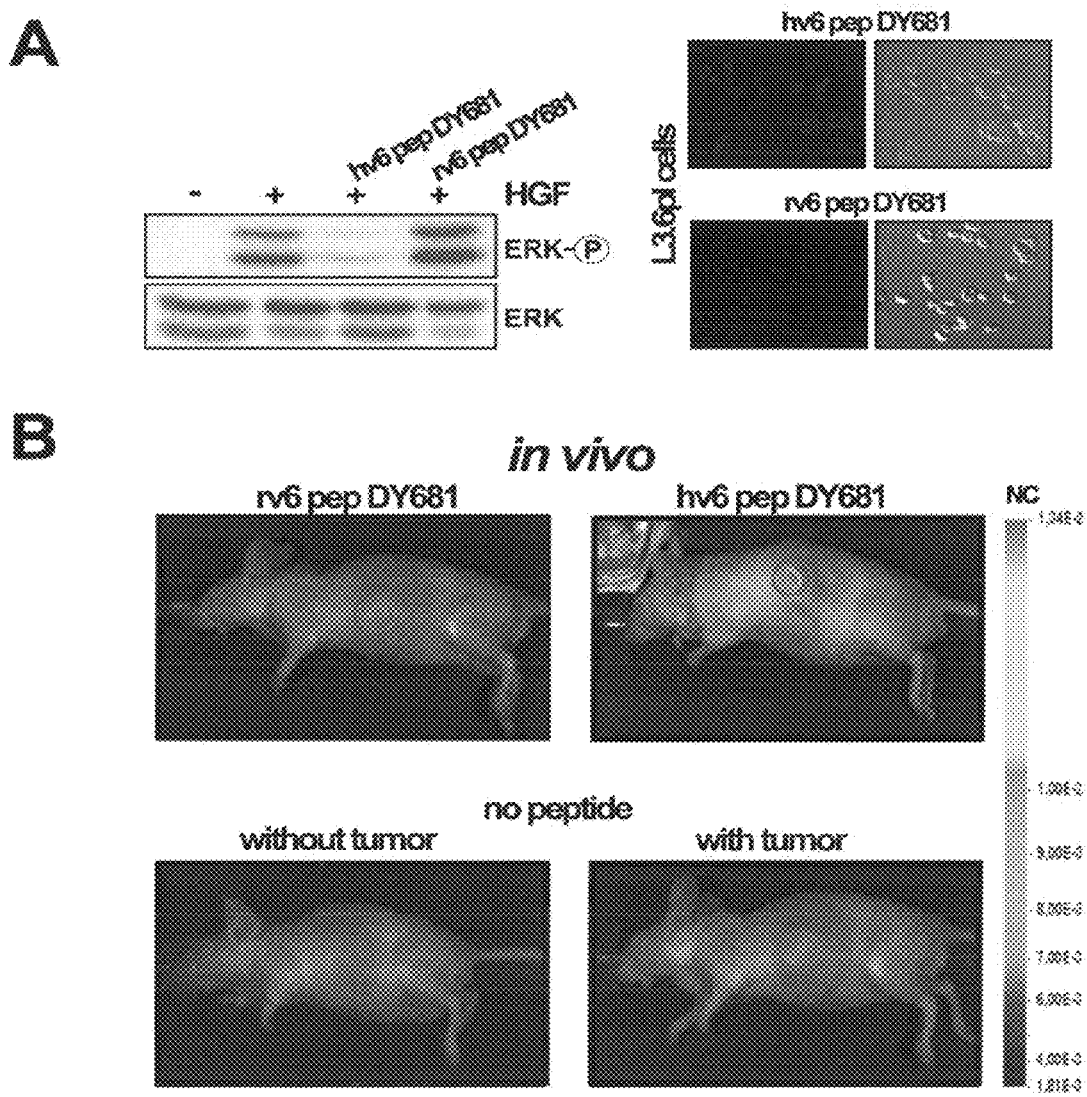
Figure 20:
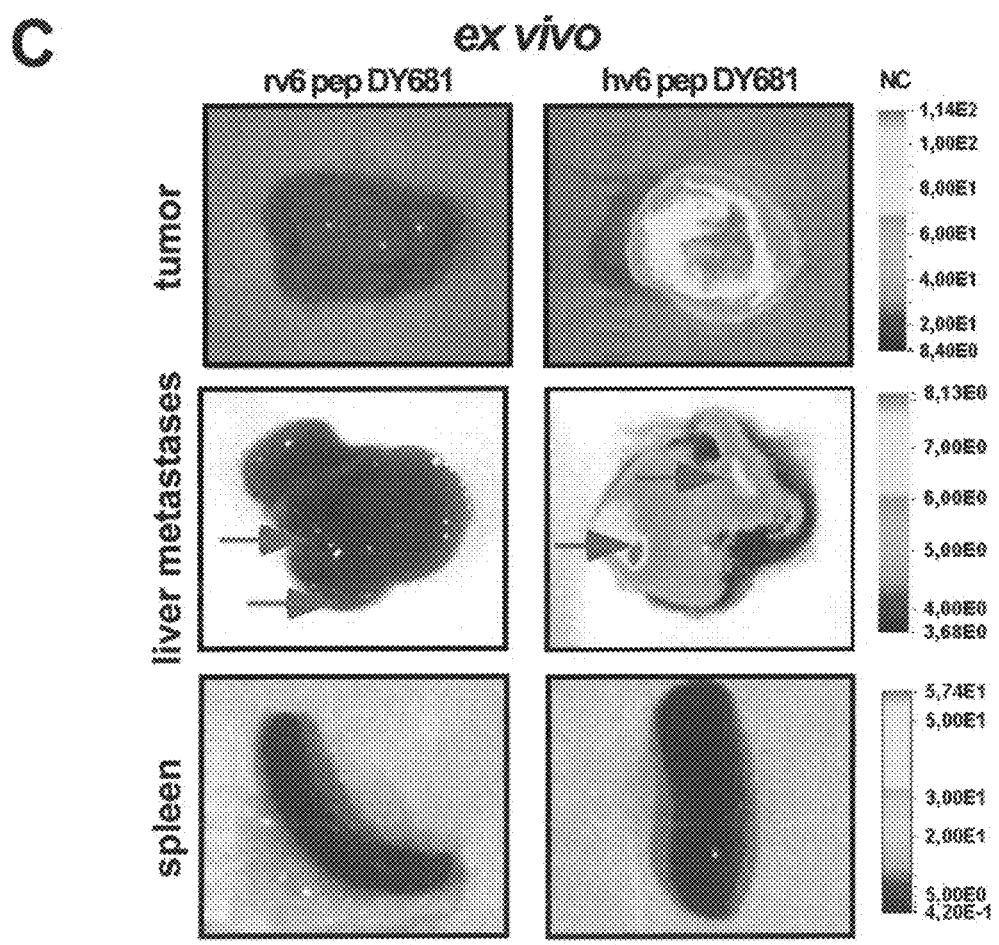
Figure 21:
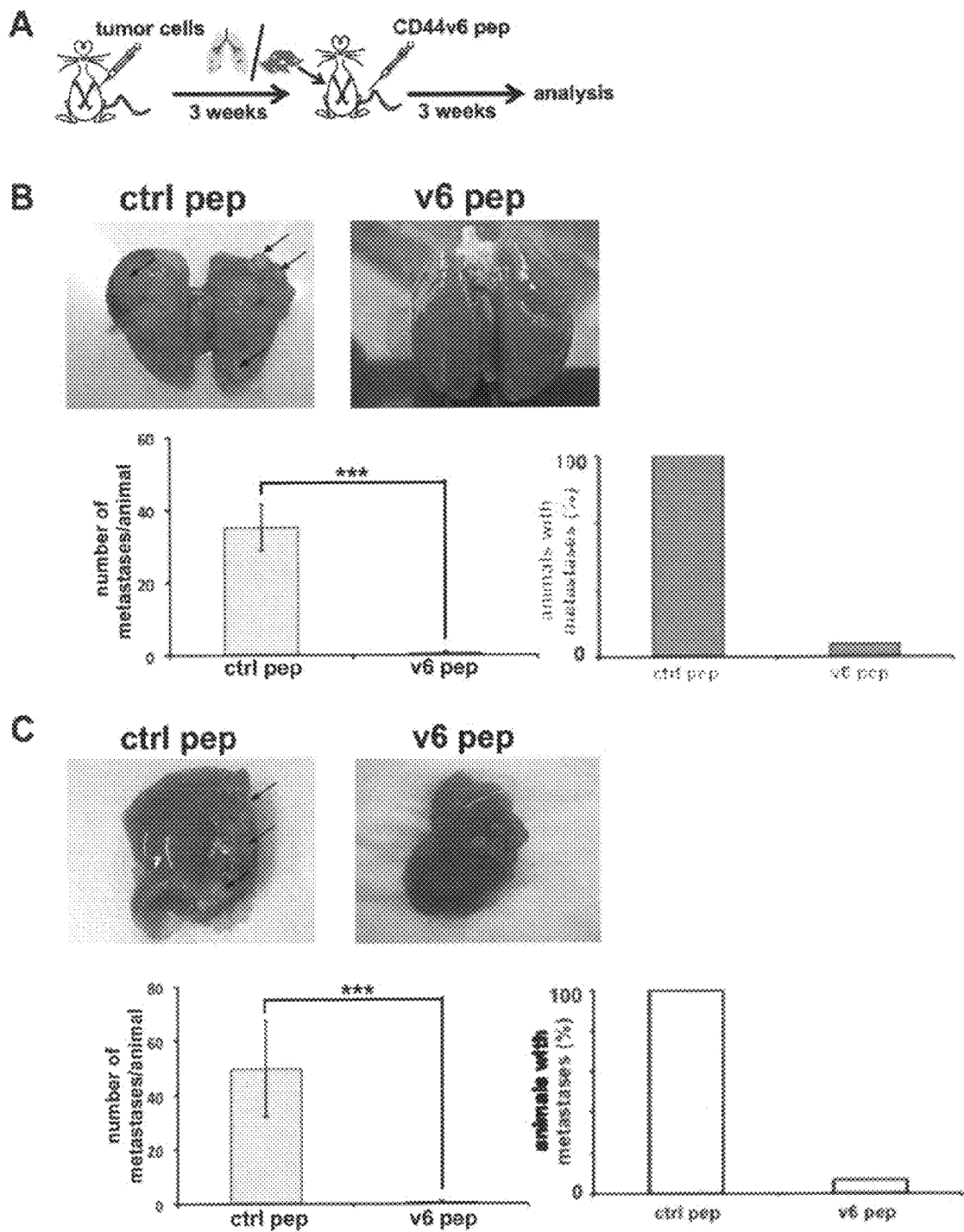
Figure 22:
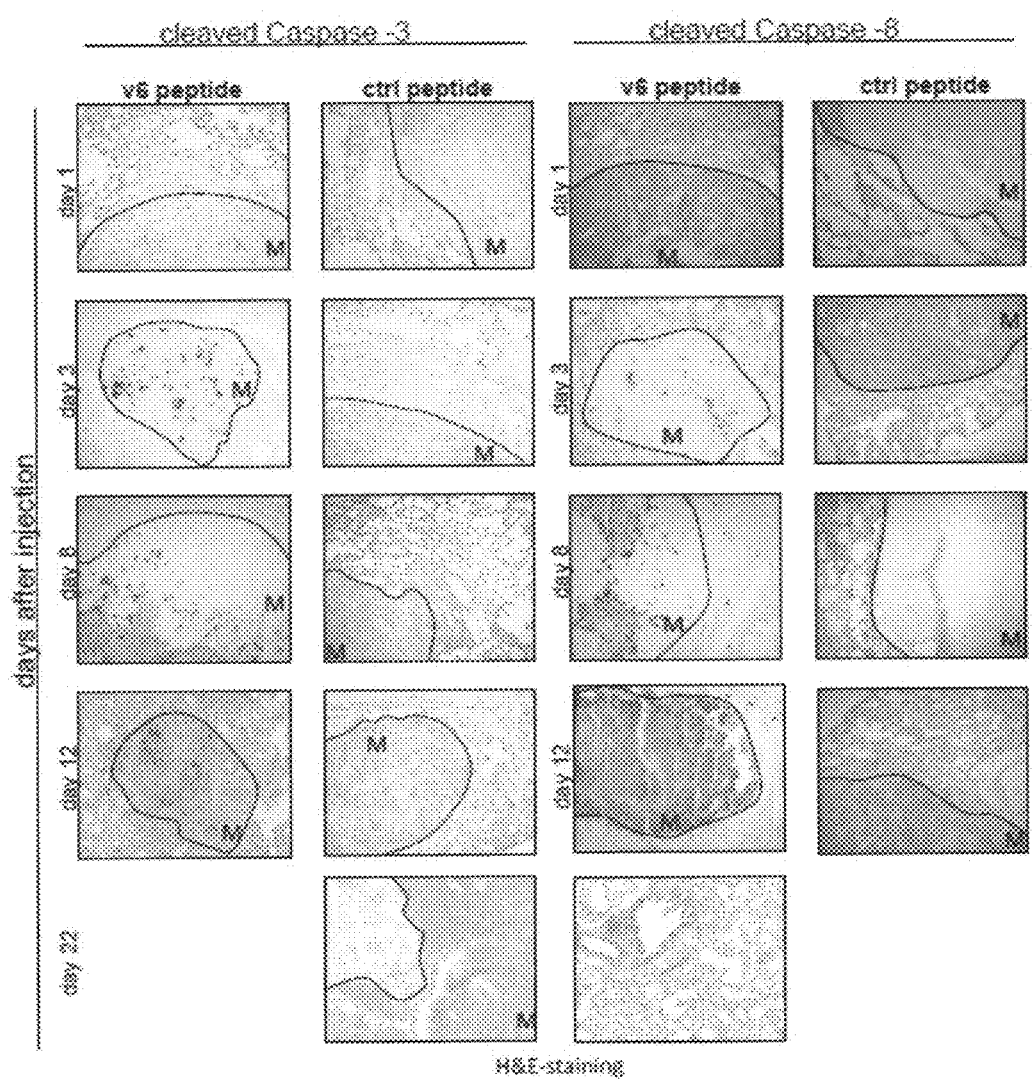
Figure 24:
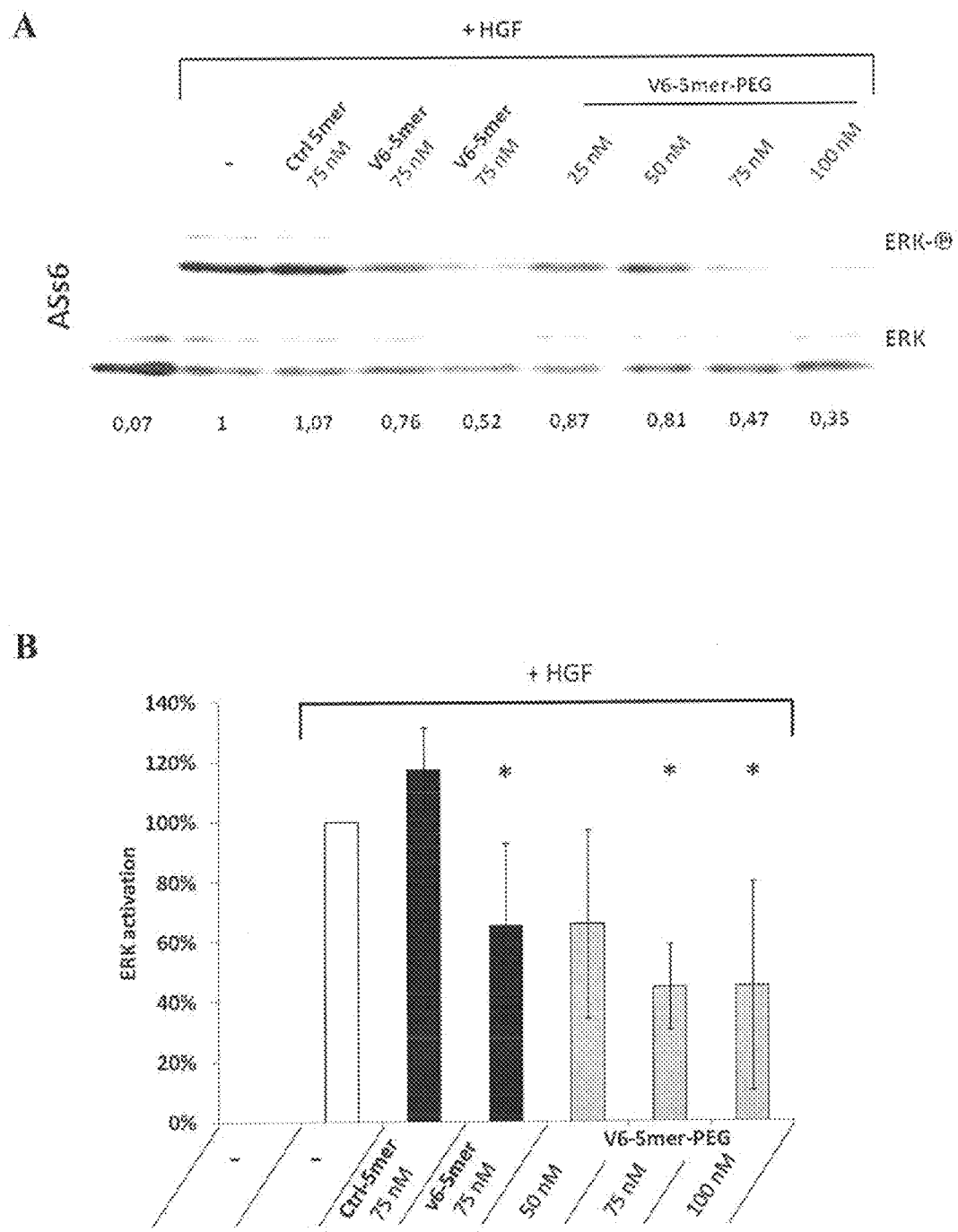
FIGS. 24 and 25 show that pegylated peptides are efficient in inhibiting HGF dependent activation of Met and ERK Inhibition of ERK is even more efficient with pegylated vs. non-pegylated peptides.
Figure 25:
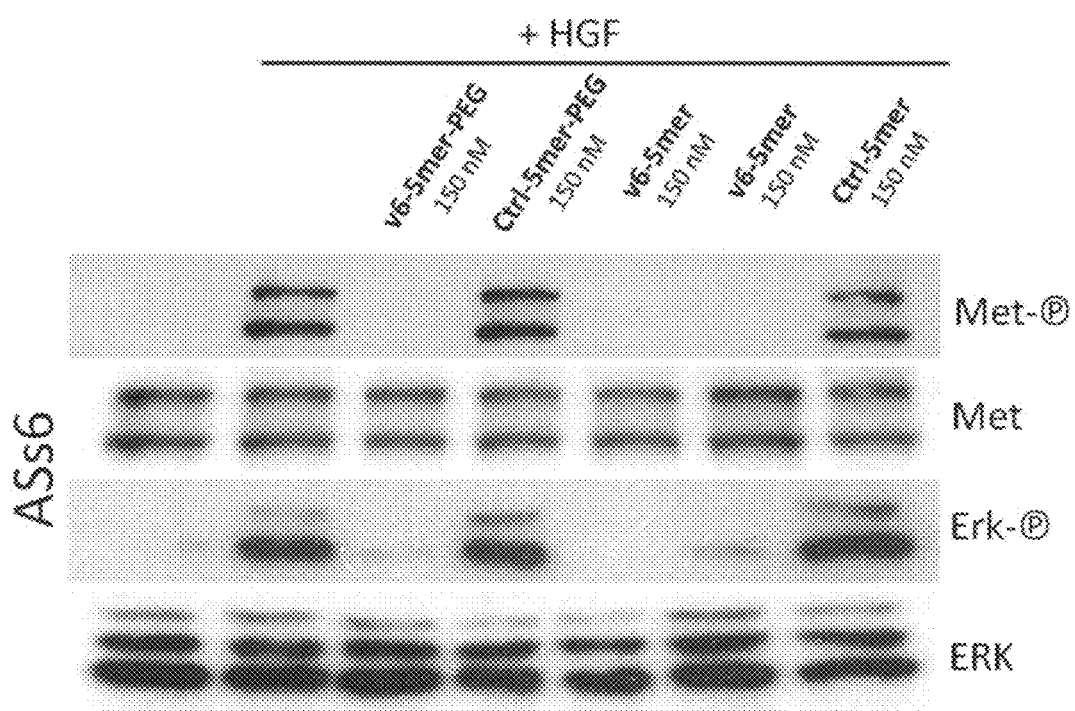
Figure 26:
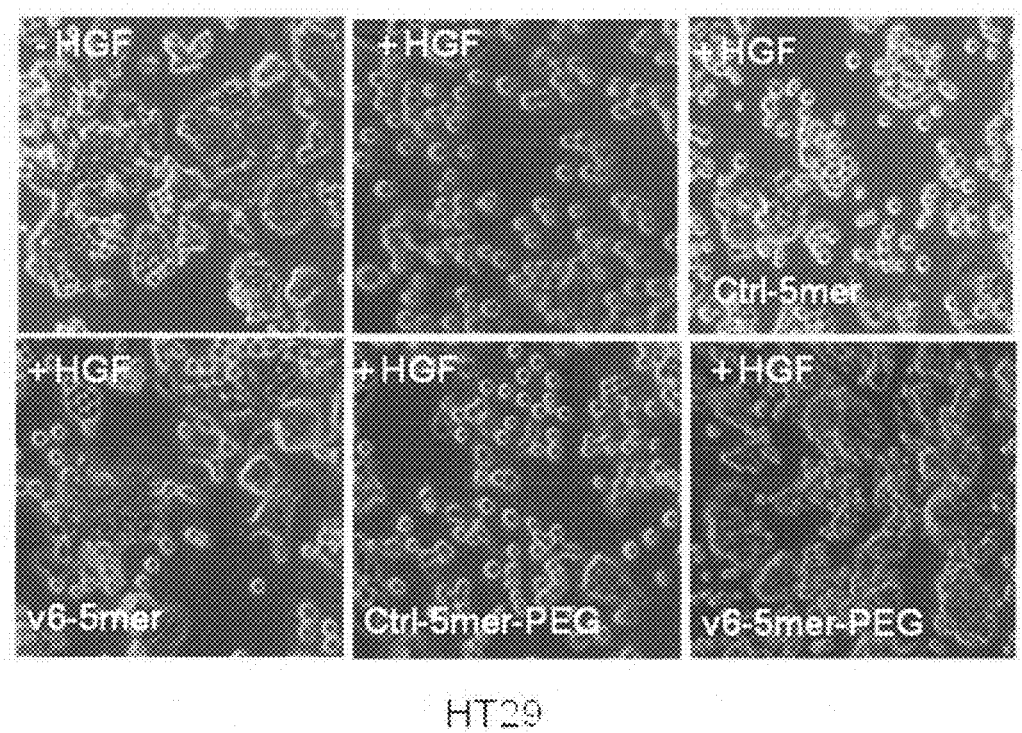
FIG. 26 shows that pegylated as well non-pegylated peptides, but not control peptides lead to dissociation and migration of cells away from these cell cluster.
Figure 27:
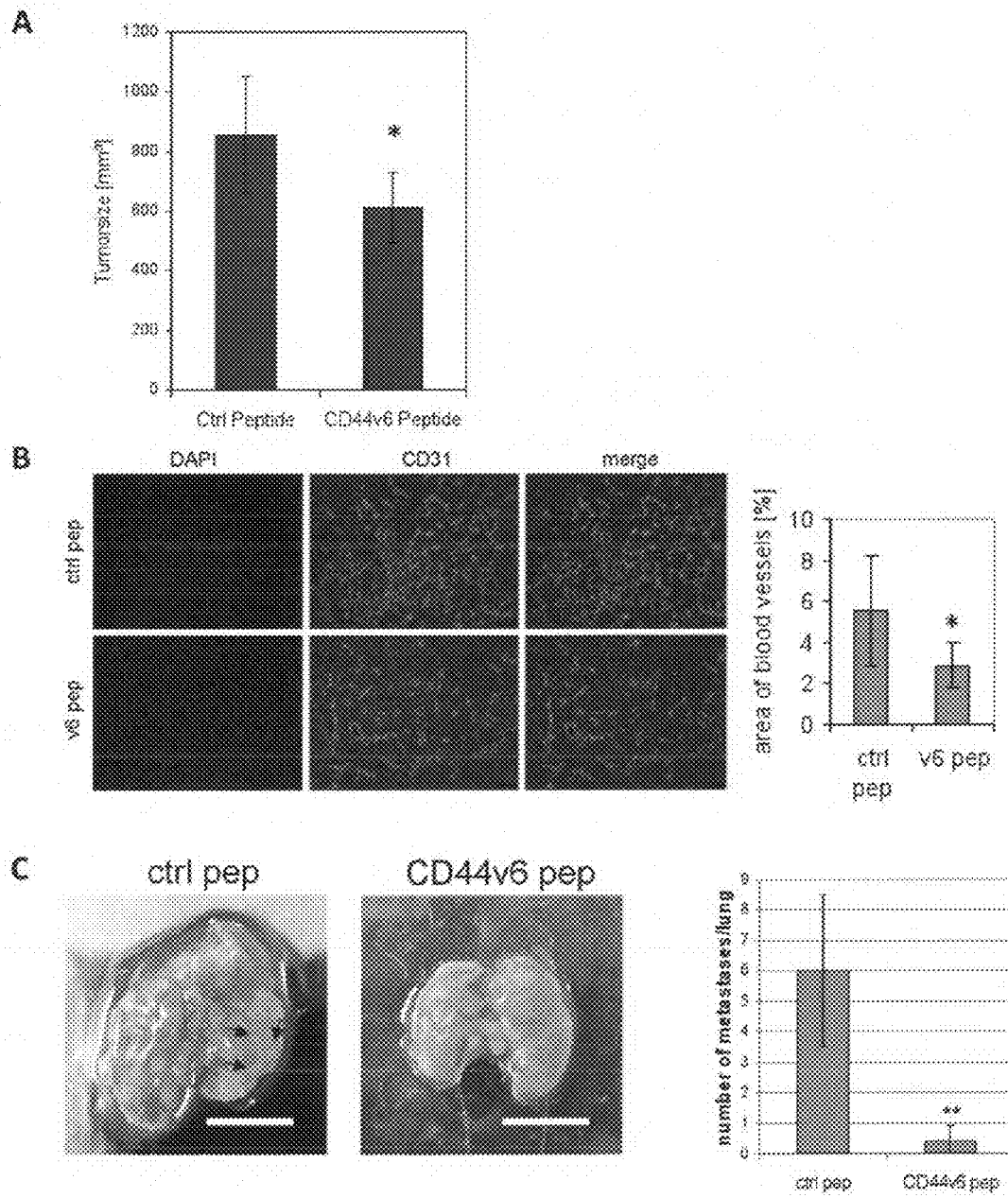

Analysis of the primary tumors revealed a significant decrease of tumor size in the v6 14mer treated group (FIG. 27A) Immunofluorescent analysis (anti-CD34 staining) to monitor tumor vascularization showed that in the v6 14mer treated group the total number of blood vessels was significantly reduced (FIG. 27B).

A difference between the v6 14mer and the control peptide treated animals could also be seen in the case of metastatic spreading. The macroscopic analysis of the lungs revealed that all mice treated with the control peptide developed metastases. The average number of metastases was 6 metastases per lung. In the v6 peptide treated group three animals showed no macroscopic metastases at all, whereas two animals had only one metastase. Therefore, the treatment with the v6 peptide drastically reduces the formation of metastases in the lung (FIG. 27C).

In conclusion the preliminary data for breast cancer revealed that the v6 14mer is as well a promising tool for this cancer type.

Example 5

In Vitro Results

Linear CD44v6 Peptides Described Herein

```
                                         (SEQ ID NO: 10)
rat: 14 mer KEKWFENEWQGKNP, (SEQ ID NO: 11)
5 mer NEWQG, (DY681-SEQ ID NO: 12)
DY681labeled 11 mer WFENEWQGKNP (SEQ ID NO: 9)
human: 14 mer KEQWFGNRWHEGYR, (SEQ ID NO: 2)
5 mer NRWHE, (DY681-SEQ ID NO: 14)
DY681labeled 11 mer WFGNRWHEGYR (DY681-SEQ ID NO: 13)
mouse: DY681labeled 11 mer WFQNGWQGKNP
```

1. In Vitro Inhibition of RTKs Using the Human v6 Peptides

```
                                        (SEQ ID NO: 9)
   Linear peptide (human, 14 mer KEQWFGNRWHEGYR, (SEQ ID NO: 2)
   5 mer NRWHE)
```

Cell Lines Used
HT29 (colorectal cancer)
HeLa (cervical cancer)
L3.6pl (human pancreatic carcinoma cell)
MCF7 (human breast cancer)
1.1 Epithelial Cells The contribution of CD44v6 to Met signaling in the human epithelial pancreatic cancer cells L3.6pl (derived from Colo 357), the cervix carcinoma cells HeLa and the colon cancer cells HT29 were analysed using the CD44v6 peptide (v6 14mer; v6 5mer tested as well, data not shown). It was able to prevent activation of Met and of its downstream target Erk when added to the cells before induction with HGF (FIGS. 28A, B and C). As incubation with a control peptide did not interfere with Met activation and signaling, these results show that CD44v6 is required for Met activation in all this cell lines.

Besides VEGFR and Met the dependency of ErbB1 on CD44v6 was investigated. EGF as well as five other ligands, namely AR, BC, ER, HB-EGF, and TGF-α, can activate the ErbB1 receptor. EGF, AR and TGF-α bind to either an ErbB1-homo- or an ErbB1/2-heterodimer. In addition to these dimers, BC, ER and HB-EGF can also bind to an Erb4/4 homo- or an ErbB2/4 heterodimer. Here it was investigated whether the activation of the ErbB receptors by the indicated ligands is also dependent on CD44v6.

Figure 29:
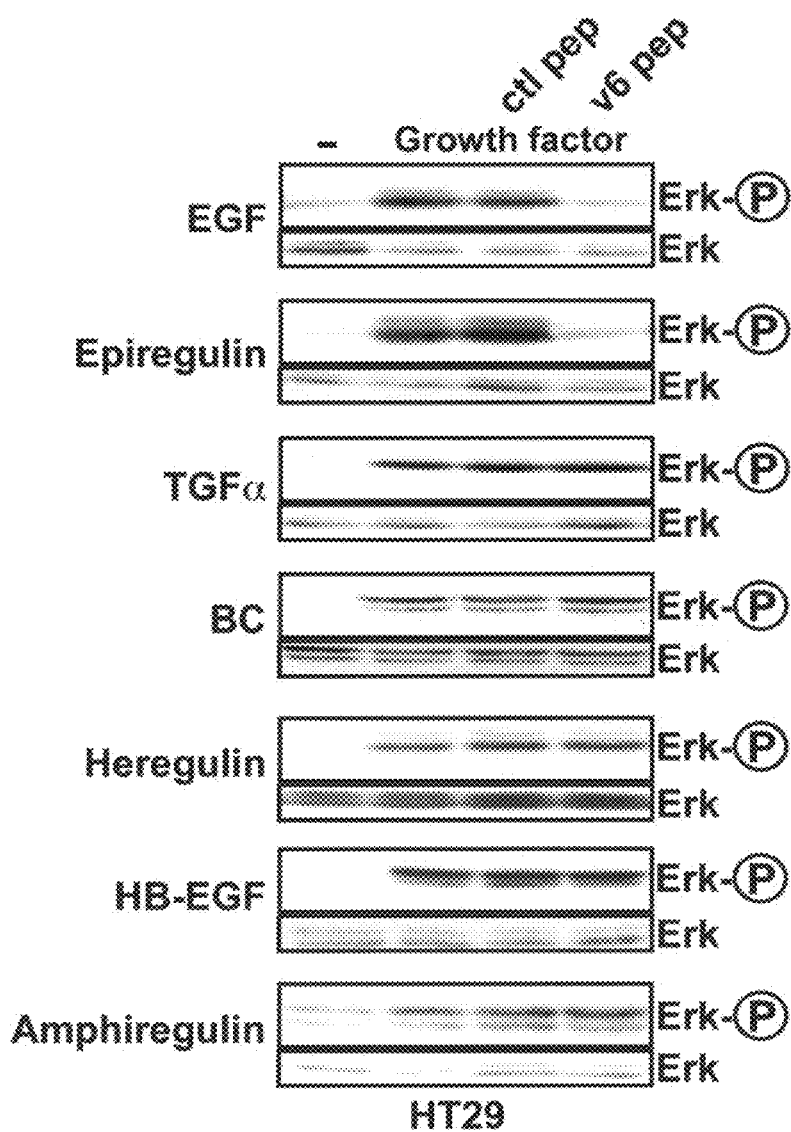

For this purpose HT29 cells were serum-starved for 24 hours and pre-treated with the v6-specific or a control peptide. They were then induced with the indicated ErbB ligands. Erk-kinase phosphorylation was used as a read-out for receptor activation. All ligands could activate the Erk-kinase. EGF- as well as ER-dependent Erk phosphorylation was inhibited by pre-incubation of HT29 cells with the CD44v6 peptide (human v6 14mer) whereas a control peptide showed no effect (FIG. 29). This shows that, besides EGF, ER is another ErbB1 ligand that is dependent on CD44v6 as a co-receptor. In contrast, AR, BC, HB-EGF and TGF-α-induced activation of the ErbB receptors could not be inhibited by blocking CD44v6 (FIG. 29). These ligands are independent of CD44v6 for their induction of the ErbB receptors. This is especially striking, since EGF and TGF-α address the same receptor pairs (ErbB1/1 or ErbB1/2). These data suggest that the specific CD44 isoform used as a co-receptor for ErbB-activation is determined by the ligand that activates the ErbB receptors and not by the receptor proteins themselves.

Figure 30:
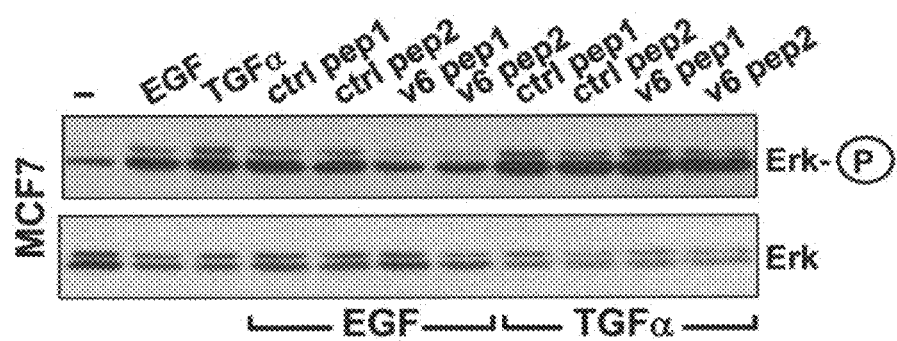

In MCF7 the CD44v6 specific peptides led to the blocking of Erk phosphorylation upon EGF treatment but not upon TGFα induction. Both peptides, the 5mer and 14mer, showed similar effects. The control peptides had no effect on Erk phosphorylation (FIG. 30).

Some of the embodiments of the invention relate to:
1. A compound for use in treating breast cancer in a human being,
   wherein said compound comprises:
      a peptide comprising at least the amino acid sequence $X_1$-R-W-H-$X_5$ (SEQ ID NO: 1) with $X_1$ being selected from the group comprising A, C, D, E, F, G, H, I, K, L, M, N, P, Q, R, S, T, V, W, or Y and $X_5$ being selected from the group comprising A, C, D, E, F, G, H, I, K, L, M, N, P, Q, R, S, T, V, W, or Y, or a peptidomimetic thereof, or
      a peptide comprising at least 5, 6, 7, 8, 9, 10, 11, 12, 13, or 14 amino acids of amino acid sequence $X_1$-$X_2$-$X_3$-$X_4$-$X_5$-$X_6$-$X_7$-R-W-H-$X_{11}$-$X_{12}$-$X_{13}$-$X_{14}$ (SEQ ID NO: 7), wherein $X_1$, $X_2$, $X_3$, $X_4$, $X_5$, $X_6$, $X_7$, $X_{11}$, $X_{12}$, $X_{13}$, or $X_{14}$ is selected from the group comprising A, C, D, E, F, G, H, I, K, L, M, N, P, Q, R, S, T, V, W, or Y, and wherein the peptide comprises at least $X_7$-R-W-H-$X_{11}$ of SEQ ID NO: 7, wherein $X_7$, and $X_{11}$ is selected from the group comprising A, C, D, E, F, G, H, I, K, L, M, N, P, Q, R, S, T, V, W, or Y, or a peptidomimetic thereof.

2. A compound for use of embodiment 1,
   wherein said compound comprises:
      a peptide comprising at least the amino acid sequence $X_1$-R-W-H-$X_5$ (SEQ ID No. 4), wherein $X_1$ is selected from the group comprising amino acids with an $NH_2$ group such as K, R, N, or Q, or amino acids with non-polar side chains such as A, V, L or I and wherein $X_5$ is selected from the group comprising amino acids with negatively charged side chains such as E or D, or amino acids with non-polar side chains such as A, V, L or I or a peptidomimetic thereof, or
      a peptide comprising at least 5, 6, 7, 8, 9, 10, 11, 12, 13, or 14 amino acids of amino acid sequence $X_1$-$X_2$-$X_3$-$X_4$-$X_5$-$X_6$-$X_7$-R-W-H-$X_{11}$-$X_{12}$-$X_{13}$-$X_{14}$ (SEQ ID NO: 8), wherein $X_1$ is selected from the group comprising amino acids with an $NH_2$ group such as K, R, N, or Q, or amino acids with non-polar side chains such as A, V, L or I, wherein $X_2$ is selected from the group comprising amino acids with negatively charged side chains such as E or D, or amino acids with non-polar side chains such as A, V, L or I, wherein $X_3$ is selected from the group comprising amino acids with an $NH_2$ group such as K, R, N, or Q, or amino acids with non-polar side chains such as A, V, L or I, wherein $X_4$ is selected from the group comprising amino acids with non-polar or non-charged side chains and aromatic ring structures such as F, W, or Y, or amino acids with non-polar side chains such as A, V, L or I, wherein $X_5$ is selected from the group comprising amino acids with non-polar or non-charged side chains and aromatic rings structures such as F, W, or Y, or amino acids with non-polar side chains such as A, V, L or I, wherein $X_6$ is selected from the group comprising G or amino acids with non-polar side chains such as A, V, L or I, wherein $X_7$ is selected from the group comprising amino acids with an $NH_2$ group such as K, R, N, or Q, or amino acids with non-polar side chains such as A, V, L or I, wherein $X_{11}$ is selected from the group comprising amino acids with negatively charged side chains such as E or D, or amino acids with non-polar side chains such as A, V, L or I, wherein $X_{12}$ is selected from the group comprising G or amino acids with non-polar side chains such as A, V, L or I, wherein $X_{13}$ is selected from the group comprising amino acids with non-polar or non-charged side chains and aromatic rings structures such F, W, or Y, or amino acids with non-polar side chains such as A, V, L or I, and wherein $X_{14}$ is selected from the group comprising amino acids with an $NH_2$ group such as K, R, N, or Q, or amino acids with non-polar side chains such as A, V, L or I, and wherein the peptide comprises at least $X_7$-R-W-H-$X_{11}$ of SEQ ID NO: 8, wherein $X_7$ is selected from the group comprising amino acids with an $NH_2$ group such as K, R, N, or Q, or amino acids with non-polar side chains such as A, V, L or I and wherein $X_{11}$ is selected from the group comprising amino acids with negatively charged side chains such as E or D, or amino acids with non-polar side chains such as A, V, L or I, or a peptidomimetic thereof.

3. A compound for use of embodiment 2,
   wherein said compound comprises:
   a peptide comprising at least the amino acid sequence $X_1$-R-W-H-$X_5$ (SEQ ID NO: 5), wherein $X_1$ is selected from the group comprising amino acids with an $NH_2$ group such as K, R, N, or Q, and wherein $X_5$ is selected from the group comprising amino acids with negatively charged side chains such as E or D, or a peptidomimetic thereof, or
   a peptide comprising at least 5, 6, 7, 8, 9, 10, 11, 12, 13, or 14 amino acids of amino acid sequence $X_1$-$X_2$-$X_3$-$X_4$-$X_5$-$X_6$-$X_7$-R-W-H-$X_{11}$-$X_{12}$-$X_{13}$-$X_{14}$ (SEQ ID NO: 9), wherein $X_1$ is selected from the group comprising amino acids with an $NH_2$ group such as K, R, N, or Q, wherein $X_2$ is selected from the group comprising amino acids with negatively charged side chains such as E or D, wherein $X_3$ is selected from the group comprising amino acids with an $NH_2$ group such as K, R, N, or Q, wherein $X_4$ is selected from the group comprising amino acids with non-polar or non-charged side chains and aromatic ring structures such as F, W, or Y, wherein $X_5$ is selected from the group comprising amino acids with non-polar or non-charged side chains and aromatic rings structures such as F, W, or Y, wherein $X_6$ is selected from the group comprising G or amino acids with non-polar side chains such as A, V, L or I, wherein $X_7$ is selected from the group comprising amino acids with an $NH_2$ group such as K, R, N, or Q, wherein $X_{11}$ is selected from the group comprising amino acids with negatively charged side chains such as E or D, wherein $X_{12}$ is selected from the group comprising G or amino acids with non-polar side chains such as A, V, L or I, wherein $X_{13}$ is selected from the group comprising amino acids with non-polar or non-charged side chains and aromatic rings structures such F, W, or Y, and wherein $X_{14}$ is selected from the group comprising amino acids with an $NH_2$ group such as K, R, N, or Q, and wherein the peptide comprises at least $X_7$-R-W-H-$X_{11}$ of SEQ ID NO: 9, wherein $X_7$ is selected from the group comprising amino acids with an $NH_2$ group such as K, R, N, or Q and wherein $X_{11}$ is selected from the group comprising amino acids with negatively charged side chains such as E or D, or a peptidomimetic thereof.

4. A compound for use of embodiment 1, 2, or 3
   wherein said compound comprises a peptide comprising, optionally consisting of, the amino acid sequence N-R-W-H-E (SEQ ID NO: 2), amino acid sequence K-E-Q-W-F-G-N-R-W-H-E-G-Y-R (SEQ ID NO: 6), or a peptidomimetic thereof.

5. A compound for use of embodiment 1, 2, 3, or 4,
   wherein said compound is a modified form of said peptide or said peptidomimetic.

6. A compound for use of embodiment 5,
   wherein said compound is a pegylated, hesylated, pasylated, myristoylated, glycosylated, and/or cyclic form of said peptide or peptidomimetic.

7. A compound for use of embodiment 1, 2, 3, 4, or 5,
   wherein the compound is formulated for oral, nasal, or subcutaneous administration.

8. A pharmaceutical composition for use in treating breast cancer in a human being,
   wherein said pharmaceutical composition comprises a compound comprising:
   a peptide comprising at least the amino acid sequence $X_1$-R-W-H-$X_5$ (SEQ ID NO: 1) with $X_1$ being selected from the group comprising A, C, D, E, F, G, H, I, K, L, M, N, P, Q, R, S, T, V, W, or Y and $X_5$ being selected from the group comprising A, C, D, E, F, G, H, I, K, L, M, N, P, Q, R, S, T, V, W, or Y, or a peptidomimetic thereof, or
   a peptide comprising at least 5, 6, 7, 8, 9, 10, 11, 12, 13, or 14 amino acids of amino acid sequence $X_1$-$X_2$-$X_3$-$X_4$-$X_5$-$X_6$-$X_7$-R-W-H-$X_{11}$-$X_{12}$-$X_{13}$-$X_{14}$ (SEQ ID NO: 7), wherein $X_1$, $X_2$, $X_3$, $X_4$, $X_5$, $X_6$, $X_7$, $X_{11}$, $X_{12}$, $X_{13}$, or $X_{14}$ is selected from the group comprising A, C, D, E, F, G, H, I, K, L, M, N, P, Q, R, S, T, V, W, or Y, and wherein the peptide comprises at least $X_7$-R-W-H-$X_{11}$ of SEQ ID NO: 7, wherein $X_7$, and $X_{11}$ is selected from the group comprising A, C, D, E, F, G, H, I, K, L, M, N, P, Q, R, S, T, V, W, or Y, or a peptidomimetic thereof.

9. A pharmaceutical composition for use of embodiment 8,
   wherein said pharmaceutical composition comprises a compound comprising:
   a peptide comprising at least the amino acid sequence $X_1$-R-W-H-$X_5$ (SEQ ID NO: 4), wherein $X_1$ is selected from the group comprising amino acids with an $NH_2$ group such as K, R, N, or Q, or amino acids with non-polar side chains such as A, V, L or I and wherein $X_5$ is selected from the group comprising amino acids with negatively charged side chains such as E or D, or amino acids with non-polar side chains such as A, V, L or I or a peptidomimetic thereof, or
   a peptide comprising at least 5, 6, 7, 8, 9, 10, 11, 12, 13, or 14 amino acids of amino acid sequence $X_1$-$X_2$-$X_3$-$X_4$-$X_5$-$X_6$-$X_7$-R-W-H-$X_{11}$-$X_{12}$-$X_{13}$-$X_{14}$ (SEQ ID NO: 8), wherein $X_1$ is selected from the group comprising amino acids with an $NH_2$ group such as K, R, N, or Q, or amino acids with non-polar side chains such as A, V, L or I, wherein $X_2$ is selected from the group comprising amino acids with negatively charged side chains such as E or D, or amino acids with non-polar side chains such as A, V, L or I, wherein $X_3$ is selected from the group comprising amino acids with an $NH_2$ group such as K, R, N, or Q, or amino acids with non-polar side chains such as A, V, L or I, wherein $X_4$ is selected from the group comprising amino acids with non-polar or non-charged side chains and aromatic ring structures such as F, W, or Y, or amino acids with non-polar side chains such as A, V, L or I, wherein $X_5$ is selected from the group comprising amino acids with non-polar or non-charged side chains and aromatic rings structures such as F, W, or Y, or amino acids with non-polar side chains such as A, V, L or I, wherein $X_6$ is selected from the group comprising G or amino acids with non-polar side chains such as A, V, L or I, wherein $X_7$ is selected from the group comprising amino acids with an $NH_2$ group such as K, R, N, or Q, or amino acids with non-polar side chains such as A, V, L or I, wherein $X_{11}$ is selected from the group comprising amino acids with negatively charged side chains such as E or D, or amino acids with non-polar side chains such as A, V, L or I, wherein $X_{12}$ is selected from the group comprising G or amino acids with non-polar side chains such as A, V, L or I, wherein $X_{13}$ is selected from the group comprising amino acids with non-polar or non-charged side chains and aromatic rings structures such F, W, or Y, or amino acids with non-polar side chains such as A, V, L or I, and wherein $X_{14}$ is selected from the group comprising amino acids with an $NH_2$ group such as K, R, N, or Q, or amino acids with non-polar side chains such as A, V, L or I, and wherein the peptide comprises at least $X_7$-R-W-H-$X_{11}$ of SEQ ID NO: 8, wherein $X_7$ is selected from the group comprising amino acids with an $NH_2$ group such as K, R, N, or Q, or amino acids with non-polar side chains such as A, V, L or I and wherein $X_{11}$ is selected from the group comprising amino acids with negatively charged side chains such as E or D, or amino acids with non-polar side chains such as A, V, L or I, or a peptidomimetic thereof.

10. A pharmaceutical composition for use of embodiment 9, wherein said pharmaceutical composition comprises a compound comprising:
a peptide comprising at least the amino acid sequence $X_1$-R-W-H-$X_5$ (SEQ ID NO: 5), wherein $X_1$ is selected from the group comprising amino acids with an $NH_2$ group such as K, R, N, or Q, and wherein $X_5$ is selected from the group comprising amino acids with negatively charged side chains such as E or D, or a peptidomimetic thereof, or
a peptide comprising at least 5, 6, 7, 8, 9, 10, 11, 12, 13, or 14 amino acids of amino acid sequence $X_1$-$X_2$-$X_3$-$X_4$-$X_5$-$X_6$-$X_7$-R-W-H-$X_{11}$-$X_{12}$-$X_{13}$-$X_{14}$ (SEQ ID NO: 9), wherein $X_1$ is selected from the group comprising amino acids with an $NH_2$ group such as K, R, N, or Q, wherein $X_2$ is selected from the group comprising amino acids with negatively charged side chains such as E or D, wherein $X_3$ is selected from the group comprising amino acids with an $NH_2$ group such as K, R, N, or Q, wherein $X_4$ is selected from the group comprising amino acids with non-polar or non-charged side chains and aromatic ring structures such as F, W, or Y, wherein $X_5$ is selected from the group comprising amino acids with non-polar or non-charged side chains and aromatic rings structures such as F, W, or Y, wherein $X_6$ is selected from the group comprising G or amino acids with non-polar side chains such as A, V, L or I, wherein $X_7$ is selected from the group comprising amino acids with an $NH_2$ group such as K, R, N, or Q, wherein $X_{11}$ is selected from the group comprising amino acids with negatively charged side chains such as E or D, wherein $X_{12}$ is selected from the group comprising G or amino acids with non-polar side chains such as A, V, L or I, wherein $X_{13}$ is selected from the group comprising amino acids with non-polar or non-charged side chains and aromatic rings structures such F, W, or Y, and wherein $X_{14}$ is selected from the group comprising amino acids with an $NH_2$ group such as K, R, N, or Q, and wherein the peptide comprises at least $X_7$-R-W-H-$X_{11}$ of SEQ ID NO: 9, wherein $X_7$ is selected from the group comprising amino acids with an $NH_2$ group such as K, R, N, or Q and wherein $X_{11}$ is selected from the group comprising amino acids with negatively charged side chains such as E or D, or a peptidomimetic thereof.

11. A pharmaceutical composition for use of embodiment 8, 9, or 10,
wherein said compound comprises a peptide comprising, optionally consisting of, amino acid sequence N-R-W-H-E (SEQ ID NO: 2), amino acid sequence K-E-Q-W-F-G-N-R-W-H-E-G-Y-R (SEQ ID NO: 6), or a peptidomimetic thereof.

12. A pharmaceutical composition for use of embodiment 8, 9, 10, or 11,
wherein said compound is a modified form of said peptide or said peptidomimetic.

13. A pharmaceutical composition for use of embodiment 12,
wherein said compound is a pegylated, hesylated, pasylated, myristoylated, glycosylated, and/or cyclic form of said peptide or peptidomimetic.

14. A pharmaceutical composition for use of embodiment 8, 9, 10, 11, 12, or 13,
wherein said pharmaceutical composition comprises a pharmaceutically acceptable excipient.

15. A pharmaceutical composition for use of embodiment 8, 9, 10, 11, 12, 13 or 14,
wherein said pharmaceutical composition is formulated for oral, nasal, or subcutaneous administration.

16. Use of a compound in the manufacture of a medicament for use in treating breast cancer in a human being,
wherein said compound comprises:
a peptide comprising at least the amino acid sequence $X_1$-R-W-H-$X_5$ (SEQ ID NO: 1) with $X_1$ being selected from the group comprising A, C, D, E, F, G, H, I, K, L, M, N, P, Q, R, S, T, V, W, or Y and $X_5$ being selected from the group comprising A, C, D, E, F, G, H, I, K, L, M, N, P, Q, R, S, T, V, W, or Y, or a peptidomimetic thereof, or
a peptide comprising at least 5, 6, 7, 8, 9, 10, 11, 12, 13, or 14 amino acids of amino acid sequence $X_1$-$X_2$-$X_3$-$X_4$-$X_5$-$X_6$-$X_7$-R-W-H-$X_{11}$-$X_{12}$-$X_{13}$-$X_{14}$ (SEQ ID NO: 7), wherein $X_1$, $X_2$, $X_3$, $X_4$, $X_5$, $X_6$, $X_7$, $X_{11}$, $X_{12}$, $X_{13}$, or $X_{14}$ is selected from the group comprising A, C, D, E, F, G, H, I, K, L, M, N, P, Q, R, S, T, V, W, or Y, and wherein the peptide comprises at least $X_7$-R-W-H-$X_{11}$ of SEQ ID NO: 7, wherein $X_7$, and $X_{11}$ is selected from the group comprising A, C, D, E, F, G, H, I, K, L, M, N, P, Q, R, S, T, V, W, or Y, or a peptidomimetic thereof.

17. Use of a compound of embodiment 16,
wherein said compound comprises:
a peptide comprising at least the amino acid sequence $X_1$-R-W-H-$X_5$ (SEQ ID NO: 4), wherein $X_1$ is selected from the group comprising amino acids with an $NH_2$ group such as K, R, N, or Q, or amino acids with non-polar side chains such as A, V, L or I and wherein $X_5$ is selected from the group comprising amino acids with negatively charged side chains such as E or D, or amino acids with non-polar side chains such as A, V, L or I or a peptidomimetic thereof, or
a peptide comprising at least 5, 6, 7, 8, 9, 10, 11, 12, 13, or 14 amino acids of amino acid sequence $X_1$-$X_2$-$X_3$-$X_4$-$X_5$-$X_6$-$X_7$-R-W-H-$X_{11}$-$X_{12}$-$X_{13}$-$X_{14}$ (SEQ ID NO: 8), wherein $X_1$ is selected from the group comprising amino acids with an $NH_2$ group such as K, R, N, or Q, or amino acids with non-polar side chains such as A, V, L or I, wherein $X_2$ is selected from the group comprising amino acids with negatively charged side chains such as E or D, or amino acids with non-polar side chains such as A, V, L or I, wherein $X_3$ is selected from the group comprising amino acids with an $NH_2$ group such as K, R, N, or Q, or amino acids with non-polar side chains such as A, V, L or I, wherein $X_4$ is selected from the group comprising amino acids with non-polar or non-charged side chains and aromatic ring structures such as F, W, or Y, or amino acids with non-polar side chains such as A, V, L or I, wherein $X_5$ is selected from the group comprising amino acids with non-polar or non-charged side chains and aromatic rings structures such as F, W, or Y, or amino acids with non-polar side chains such as A, V, L or I, wherein $X_6$ is selected from the group comprising G or amino acids with non-polar side chains such as A, V, L or I, wherein $X_7$ is selected from the group comprising amino acids with an $NH_2$ group such as K, R, N, or Q, or amino acids with non-polar side chains such as A, V, L or I, wherein $X_{11}$ is selected from the group comprising amino acids with negatively charged side chains such as E or D, or amino acids with non-polar side chains such as A, V, L or I, wherein $X_{12}$ is selected from the group comprising G or amino acids with non-polar side chains such as A, V, L or I, wherein $X_{13}$ is selected from the group comprising amino acids with non-polar or non-charged side chains and aromatic rings structures such F, W, or Y, or amino acids with non-polar side chains such as A, V, L or I, and wherein $X_{14}$ is selected from the group comprising amino acids with an $NH_2$ group such as K, R, N, or Q, or amino acids with non-polar side chains such as A, V, L or I, and wherein the peptide comprises at least $X_7$-R-W-H-$X_{11}$ of SEQ ID NO: 8, wherein $X_7$ is selected from the group comprising amino acids with an $NH_2$ group such as K, R, N, or Q, or amino acids with non-polar side chains such as A, V, L or I and wherein $X_{11}$ is selected from the group comprising amino acids with negatively charged side chains such as E or D, or amino acids with non-polar side chains such as A, V, L or I, or a peptidomimetic thereof.

18. Use of a compound of embodiment 17,
wherein said compound comprises:
a peptide comprising at least the amino acid sequence $X_1$-R-W-H-$X_5$ (SEQ ID NO: 5), wherein $X_1$ is selected from the group comprising amino acids with an $NH_2$ group such as K, R, N, or Q, and wherein $X_5$ is selected from the group comprising amino acids with negatively charged side chains such as E or D, or a peptidomimetic thereof, or
a peptide comprising at least 5, 6, 7, 8, 9, 10, 11, 12, 13, or 14 amino acids of amino acid sequence $X_1$-$X_2$-$X_3$-$X_4$-$X_5$-$X_6$-$X_7$-R-W-H-$X_{11}$-$X_{12}$-$X_{13}$-$X_{14}$ (SEQ ID NO: 9), wherein $X_1$ is selected from the group comprising amino acids with an $NH_2$ group such as K, R, N, or Q, wherein $X_2$ is selected from the group comprising amino acids with negatively charged side chains such as E or D, wherein $X_3$ is selected from the group comprising amino acids with an $NH_2$ group such as K, R, N, or Q, wherein $X_4$ is selected from the group comprising amino acids with non-polar or non-charged side chains and aromatic ring structures such as F, W, or Y, wherein $X_5$ is selected from the group comprising amino acids with non-polar or non-charged side chains and aromatic rings structures such as F, W, or Y, wherein $X_6$ is selected from the group comprising G or amino acids with non-polar side chains such as A, V, L or I, wherein $X_7$ is selected from the group comprising amino acids with an $NH_2$ group such as K, R, N, or Q, wherein $X_{11}$ is selected from the group comprising amino acids with negatively charged side chains such as E or D, wherein $X_{12}$ is selected from the group comprising G or amino acids with non-polar side chains such as A, V, L or I, wherein $X_{13}$ is selected from the group comprising amino acids with non-polar or non-charged side chains and aromatic rings structures such F, W, or Y, and wherein $X_{14}$ is selected from the group comprising amino acids with an $NH_2$ group such as K, R, N, or Q, and wherein the peptide comprises at least $X_7$-R-W-H-$X_{11}$ of SEQ ID NO: 9, wherein $X_7$ is selected from the group comprising amino acids with an $NH_2$ group such as K, R, N, or Q and wherein $X_{11}$ is selected from the group comprising amino acids with negatively charged side chains such as E or D, or a peptidomimetic thereof.

19. Use of a compound of embodiment 16, 17, or 18,
wherein said compound comprises a peptide comprising, optionally consisting of, amino acid sequence N-R-W-H-E (SEQ ID NO: 2), amino acid sequence K-E-Q-W-F-G-N-R-W-H-E-G-Y-R (SEQ ID NO: 6), or a peptidomimetic thereof.

20. Use of a compound of embodiment 16, 17, 18, or 19,
wherein said compound is a modified form of said peptide or said peptidomimetic.

21. Use of a compound of embodiment 20,
wherein said compound is a pegylated, hesylated, pasylated, myristoylated, glycosylated, and/or cyclic form of said peptide or peptidomimetic.

22. Use of a compound of embodiment 16, 17, 18, 19, 20, or 21,
wherein said medicament is formulated for oral, nasal, or subcutaneous administration.

23. Method of treating breast cancer in a human being by administering a compound to a human being in need thereof, wherein said compound comprises:
a peptide comprising at least the amino acid sequence $X_1$-R-W-H-$X_5$ (SEQ ID NO: 1) with $X_1$ being selected from the group comprising A, C, D, E, F, G, H, I, K, L, M, N, P, Q, R, S, T, V, W, or Y and $X_5$ being selected from the group comprising A, C, D, E, F, G, H, I, K, L, M, N, P, Q, R, S, T, V, W, or Y, or a peptidomimetic thereof, or
a peptide comprising at least 5, 6, 7, 8, 9, 10, 11, 12, 13, or 14 amino acids of amino acid sequence $X_1$-$X_2$-$X_3$-$X_4$-$X_5$-$X_6$-$X_7$-R-W-H-$X_{11}$-$X_{12}$-$X_{13}$-$X_{14}$ (SEQ ID NO: 7), wherein $X_1$, $X_2$, $X_3$, $X_4$, $X_5$, $X_6$, $X_7$, $X_{11}$, $X_{12}$, $X_{13}$, or $X_{14}$ is selected from the group comprising A, C, D, E, F, G, H, I, K, L, M, N, P, Q, R, S, T, V, W, or Y, and wherein the peptide comprises at least $X_7$-R-W-H-$X_{11}$ of SEQ ID NO: 7, wherein $X_7$, and $X_{11}$ is selected from the group comprising A, C, D, E, F, G, H, I, K, L, M, N, P, Q, R, S, T, V, W, or Y, or a peptidomimetic thereof.

24. Method of embodiment 23,
wherein said compound comprises:
a peptide comprising at least the amino acid sequence $X_1$-R-W-H-$X_5$ (SEQ ID NO: 4), wherein $X_1$ is selected from the group comprising amino acids with an $NH_2$ group such as K, R, N, or Q, or amino acids with non-polar side chains such as A, V, L or I and wherein $X_5$ is selected from the group comprising amino acids with negatively charged side chains such as E or D, or amino acids with non-polar side chains such as A, V, L or I or a peptidomimetic thereof, or a peptide comprising at least 5, 6, 7, 8, 9, 10, 11, 12, 13, or 14 amino acids of amino acid sequence $X_1$-$X_2$-$X_3$-$X_4$-$X_5$-$X_6$-$X_7$-R-W-H-$X_{11}$-$X_{12}$-$X_{13}$-$X_{14}$ (SEQ ID NO: 8), wherein $X_1$ is selected from the group comprising amino acids with an $NH_2$ group such as K, R, N, or Q, or amino acids with non-polar side chains such as A, V, L or I, wherein $X_2$ is selected from the group comprising amino acids with negatively charged side chains such as E or D, or amino acids with non-polar side chains such as A, V, L or I, wherein $X_3$ is selected from the group comprising amino acids with an $NH_2$ group such as K, R, N, or Q, or amino acids with non-polar side chains such as A, V, L or I, wherein $X_4$ is selected from the group comprising amino acids with non-polar or non-charged side chains and aromatic ring structures such as F, W, or Y, or amino acids with non-polar side chains such as A, V, L or I, wherein $X_5$ is selected from the group comprising amino acids with non-polar or non-charged side chains and aromatic rings structures such as F, W, or Y, or amino acids with non-polar side chains such as A, V, L or I, wherein $X_6$ is selected from the group comprising G or amino acids with non-polar side chains such as A, V, L or I, wherein $X_7$ is selected from the group comprising amino acids with an $NH_2$ group such as K, R, N, or Q, or amino acids with non-polar side chains such as A, V, L or I, wherein $X_{11}$ is selected from the group comprising amino acids with negatively charged side chains such as E or D, or amino acids with non-polar side chains such as A, V, L or I, wherein $X_{12}$ is selected from the group comprising G or amino acids with non-polar side chains such as A, V, L or I, wherein $X_{13}$ is selected from the group comprising amino acids with non-polar or non-charged side chains and aromatic rings structures such F, W, or Y, or amino acids with non-polar side chains such as A, V, L or I, and wherein $X_{14}$ is selected from the group comprising amino acids with an $NH_2$ group such as K, R, N, or Q, or amino acids with non-polar side chains such as A, V, L or I, and wherein the peptide comprises at least $X_7$-R-W-H-$X_{11}$ of SEQ ID NO: 8, wherein $X_7$ is selected from the group comprising amino acids with an $NH_2$ group such as K, R, N, or Q, or amino acids with non-polar side chains such as A, V, L or I and wherein $X_{11}$ is selected from the group comprising amino acids with negatively charged side chains such as E or D, or amino acids with non-polar side chains such as A, V, L or I, or a peptidomimetic thereof.

25. Method of embodiment 24,
wherein said compound comprises:
a peptide comprising at least the amino acid sequence $X_1$-R-W-H-$X_5$ (SEQ ID NO: 5), wherein $X_1$ is selected from the group comprising amino acids with an $NH_2$ group such as K, R, N, or Q, and wherein $X_5$ is selected from the group comprising amino acids with negatively charged side chains such as E or D, or a peptidomimetic thereof, or
a peptide comprising at least 5, 6, 7, 8, 9, 10, 11, 12, 13, or 14 amino acids of amino acid sequence $X_1$-$X_2$-$X_3$-$X_4$-$X_5$-$X_6$-$X_7$-R-W-H-$X_{11}$-$X_{12}$-$X_{13}$-$X_{14}$ (SEQ ID NO: 9), wherein $X_1$ is selected from the group comprising amino acids with an $NH_2$ group such as K, R, N, or Q, wherein $X_2$ is selected from the group comprising amino acids with negatively charged side chains such as E or D, wherein $X_3$ is selected from the group comprising amino acids with an $NH_2$ group such as K, R, N, or Q, wherein $X_4$ is selected from the group comprising amino acids with non-polar or non-charged side chains and aromatic ring structures such as F, W, or Y, wherein $X_5$ is selected from the group comprising amino acids with non-polar or non-charged side chains and aromatic rings structures such as F, W, or Y, wherein $X_6$ is selected from the group comprising G or amino acids with non-polar side chains such as A, V, L or I, wherein $X_7$ is selected from the group comprising amino acids with an $NH_2$ group such as K, R, N, or Q, wherein $X_{11}$ is selected from the group comprising amino acids with negatively charged side chains such as E or D, wherein $X_{12}$ is selected from the group comprising G or amino acids with non-polar side chains such as A, V, L or I, wherein $X_{13}$ is selected from the group comprising amino acids with non-polar or non-charged side chains and aromatic rings structures such F, W, or Y, and wherein $X_{14}$ is selected from the group comprising amino acids with an $NH_2$ group such as K, R, N, or Q, and wherein the peptide comprises at least $X_7$-R-W-H-$X_{11}$ of SEQ ID NO: 9, wherein $X_7$ is selected from the group comprising amino acids with an $NH_2$ group such as K, R, N, or Q and wherein $X_{ii}$ is selected from the group comprising amino acids with negatively charged side chains such as E or D, or a peptidomimetic thereof.

26. Method of embodiment 23, 24, or 25,
wherein said compound comprises a peptide comprising, optionally consisting of, amino acid sequence N-R-W-H-E (SEQ ID NO: 2), amino acid sequence K-E-Q-W-F-G-N-R-W-H-E-G-Y-R (SEQ ID NO: 6), or a peptidomimetic thereof.

27. Method of embodiment 23, 24, 25, or 26,
wherein said compound is a modified form of said peptide or said peptidomimetic.

28. Method of embodiment 27,
wherein said compound is a pegylated, hesylated, pasylated, myristoylated, glycosylated, and/or cyclic form of said peptide or peptidomimetic.

29. Method of embodiment 23, 24, 25, 26, 27, or 28,
wherein said compound is formulated for oral, nasal, or subcutaneous administration.

30. Compound for use of any of embodiments 1, 2, 3, 4, 5, 6 or 7, a pharmaceutical composition for use of any of embodiments 8, 9, 10, 11, 12, 13, 14, or 15, use of any of embodiments 16, 17, 18, 19, 20, 21 or 22 or Method of any of embodiments 23, 24, 25, 26, 27, 28, or 29,
wherein said breast cancer shows expression of CD44v6.

31. Compound for use of any of embodiments 1, 2, 3, 4, 5, 6, 7, or 30, a pharmaceutical composition for use of any of embodiments 8, 9, 10, 11, 12, 13, 14, 15, or 30, use of any of embodiments 16, 17, 18, 19, 20, 21, 22, or 30, or Method of any of embodiments 23, 24, 25, 26, 27, 28, 29, or 30,
wherein said breast cancer shows increased expression of ErbB1 and/or ErbB2.

32. Compound for use of any of embodiments 1, 2, 3, 4, 5, 6, 7, 30, or 31, a pharmaceutical composition for use of any of embodiments 8, 9, 10, 11, 12, 13, 14, 15, 30, or 31, use of any of embodiments 16, 17, 18, 19, 20, 21, 22, 30, or 31, or Method of any of embodiments 23, 24, 25, 26, 27, 28, 29, 30, or 31,
wherein said breast cancer shows no constitutive ErbB2 activation.

33. Compound for use of any of embodiments 1, 2, 3, 4, 5, 6, 7, 30, 31, or 32, a pharmaceutical composition for use of any of embodiments 8, 9, 10, 11, 12, 13, 14, 15, 30, 31, or 32 use of any of embodiments 16, 17, 18, 19, 20, 21, 22, 30, 31, or 32, or Method of any of embodiments 23, 24, 25, 26, 27, 28, 29, 30, 31, or 32,
wherein said breast cancer shows increased expression of EGF and/or ER.

34. Compound for use of any of embodiments 1, 2, 3, 4, 5, 6, 7, 30, 31, 32, or 33, a pharmaceutical composition for use of any of embodiments 8, 9, 10, 11, 12, 13, 14, 15, 30, 31, 32, or 33, use of any of embodiments 16, 17, 18, 19, 20, 21, 22, 30, 31, 32, or 33, or Method of any of embodiments 23, 24, 25, 26, 27, 28, 29, 30, 31, 32, or 33, wherein said breast cancer shows increased expression of EGF and/or ER, but not of TGFα.

35. Compound for use of any of embodiments 1, 2, 3, 4, 5, 6, 7, 30, 31, 32, 33, or 34, a pharmaceutical composition for use of any of embodiments 8, 9, 10, 11, 12, 13, 14, 15, 30, 31, 32, 33, or 34, use of any of embodiments 16, 17, 18, 19, 20, 21, 22, 30, 31, 32, 33, or 34, or Method of any of embodiments 23, 24, 25, 26, 27, 28, 29, 30, 31, 32, 33, or 34,
wherein said breast cancer tumor shows and EGF-based ErbB activation.

36. Compound for use of any of embodiments 1, 2, 3, 4, 5, 6, 7, 30, 31, 32, 33, 34, or 35, a pharmaceutical composition for use of any of embodiments 8, 9, 10, 11, 12, 13, 14, 15, 30, 31, 32, 33, 34, or 35, use of any of embodiments 16, 17, 18, 19, 20, 21, 22, 30, 31, 32, 33, 34, or 35, or Method of any of embodiments 23, 24, 25, 26, 27, 28, 29, 30, 31, 32, 33, 34, or 35,
wherein said breast cancer is resistant to treatment with trastuzumab or pertuzumab.

37. Compound for use of any of embodiments 1, 2, 3, 4, 5, 6, 7, 30, 31, 32, 33, 34, 35, or 36, a pharmaceutical composition for use of any of embodiments 8, 9, 10, 11, 12, 13, 14, 15, 30, 31, 32, 33, 34, 35, or 36, use of any of embodiments 16, 17, 18, 19, 20, 21, 22, 30, 31, 32, 33, 34, 35, or 36, or Method of any of embodiments 23, 24, 25, 26, 27, 28, 29, 30, 31, 32, 33, 34, 35, or 36,
wherein said breast cancer is resistant to treatment with trastuzumab or pertuzumab and shows increased expression of Met.

38. Compound for use of any of embodiments 1, 2, 3, 4, 5, 6, 7, 30, 31, 32, 33, 34, 35, 36, or 37, a pharmaceutical composition for use of any of embodiments 8, 9, 10, 11, 12, 13, 14, 15, 30, 31, 32, 33, 34, 35, 36, or 37, use of any of embodiments 16, 17, 18, 19, 20, 21, 22, 30, 31, 32, 33, 34, 35, 36, or 37, or Method of any of embodiments 23, 24, 25, 26, 27, 28, 29, 30, 31, 32, 33, 34, 35, 36, or 37,
wherein said breast cancer is a metastasizing breast cancer.

39. Compound for use of any of embodiments 1, 2, 3, 4, 5, 6, 7, 30, 31, 32, 33, 34, 35, 36, 37, or 38, a pharmaceutical composition for use of any of embodiments 8, 9, 10, 11, 12, 13, 14, 15, 30, 31, 32, 33, 34, 35, 36, 37, or 38, use of any of embodiments 16, 17, 18, 19, 20, 21, 22, 30, 31, 32, 33, 34, 35, 36, 37, or 38, or Method of any of embodiments 23, 24, 25, 26, 27, 28, 29, 30, 31, 32, 33, 34, 35, 36, 37, or 38,
wherein said metastasizing cancer is classifiable as Stage III or Stage IV according to the TNM anatomic/prognostic group system of the cancer staging system of the American Joint Committee on Cancer.

40. Compound for use of any of embodiments 1, 2, 3, 4, 5, 6, 7, 30, 31, 32, 33, 34, 35, 36, 37, 38, or 39, a pharmaceutical composition for use of any of embodiments 8, 9, 10, 11, 12, 13, 14, 15, 30, 31, 32, 33, 34, 35, 36, 37, 38, or 39, use of any of embodiments 16, 17, 18, 19, 20, 21, 22, 30, 31, 32, 33, 34, 35, 36, 37, 38, or 39, or method of any of embodiments 23, 24, 25, 26, 27, 28, 29, 30, 31, 32, 33, 34, 35, 36, 37, 38, or 39,
wherein said metastasizing cancer is classifiable as Stage IV according to the TNM anatomic/prognostic group system of the cancer staging system of the American Joint Committee on Cancer.

CITED REFERENCES

1. Aslakson C J, Miller F R (1992) Selective events in the metastatic process defined by analysis of the sequential dissemination of subpopulations of a mouse mammary tumor. Cancer Research 52: 1399-1405
2. Cook P W, Mattox P A, Keeble W W, Pittelkow M R, Plowman G D, Shoyab M, Adelman J P, Shipley G D (1991) A heparin sulfate-regulated human keratinocyte autocrine factor is similar or identical to amphiregulin. Mol Cell Biol 11: 2547-2557
3. Ekstrand A J, Sugawa N, James C D, Collins VP (1992) Amplified and rearranged epidermal growth factor receptor genes in human glioblastomas reveal deletions of sequences encoding portions of the N- and/or C-terminal tails. Proc Natl Acad Sci USA 89: 4309-4313
4. Gramlich T L, Fritsch C, Shear S, Sgoutas D, Tuten T, Gansler T (1993) Analysis of epidermal growth factor receptor gene expression in stained smears and formalin-fixed, paraffin embedded cell pellets by reverse transcription intron differential polymerase chain reaction. Anal Quant Cytol Histol 15: 317-322
5. Gunthert U, Hofmann M, Rudy W, Reber S, Zoller M, Haussmann I, Matzku S, Wenzel A, Ponta H, Herrlich P (1991) A new variant of glycoprotein CD44 confers metastatic potential to rat carcinoma cells. Cell 65: 13-24
6. Higashiyama S, Lau K, Besner G E, Abraham J A, Klagsbrun M (1992) Structure of heparinbinding EGF-like growth factor. Multiple forms, primary structure, and glycosylation of the mature protein. J Biol Chem 267: 6205-6212
7. Hynes N E, MacDonald G (2009) ErbB receptors and signaling pathways in cancer. Curr Opin Cell Biol 21: 177-184
8. König H, Ponta H, Herrlich P (1998) Coupling of signal transduction to alternative premRNA splicing by a composite splice regulator. EMBO J 10: 2904-2913
9. Morgenstern J P, Land H (1990) A series of mammalian expression vectors and characterisation of their expression of a reporter gene in stably and transiently transfected cells. Nucleic Acids Res 18: 1068
10. Naor D, Sionov R V, Ish-Shalom D (1997) CD44: Structure, Function and Association with the Malignant Process. In Advances in Cancer Research, Vande Woude G F, Klein G (eds), Vol. 71, pp 243-318. San-Diego
11. Olayioye M A, Neve R M, Lane H A, Hynes N E (2000) The ErbB signaling network: receptor heterodimerization in development and cancer. Embo J 19: 3159-3167
12. Orian-Rousseau V, Chen L, Sleeman J P, Herrlich P, Ponta H (2002) CD44 is required for two consecutive steps in HGF/c-Met signaling. Genes Dev 16: 3074-3086
13. Rodriguez-Fragoso L, Melendez K, Hudson L G, Lauer F T, Burchiel S W (2009) EGF-receptor phosphorylation and downstream signaling are activated by benzo[a]pyrene 3,6-quinone and benzo[a]pyrene 1,6-quinone in human mammary epithelial cells. Toxicol Appl Pharmacol 235: 321-328

14. Ross J S, Fletcher J A (1998) The HER-2/neu Oncogene in Breast Cancer: Prognostic Factor, Predictive Factor, and Target for Therapy. Oncologist 3: 237-252
15. Rudy W, Hofmann M, Schwartz-Albiez R, Zoller M, Heider K H, Ponta H, Herrlich P (1993) The two major CD44 proteins expressed on a metastatic rat tumor cell line are derived from different splice variants: each one individually suffices to confer metastatic behavior. Cancer Res 53: 1262-1268.
16. Salomon D S, Kidwell W R, Kim N, Ciardiello F, Bates S E, Valverius E, Lippman M E, Dickson R B, Stampfer M (1989) Modulation by estrogen and growth factors of transforming growth factor-alpha and epidermal growth factor receptor expression in normal and malignant human mammary epithelial cells. Recent Results Cancer Res 113: 57-69
17. Seiter S, Arch R, Reber S, Komitowski D, Hofmann M, Ponta H, Herrlich P, Matzku S, Zoller M (1993) Prevention of tumor metastasis formation by anti-variant CD44. J Exp Med 177: 443-455.
18. Sithanandam G, Anderson L M (2008) The ERBB3 receptor in cancer and cancer gene therapy. Cancer Gene Ther 15: 413-448
19. Sleeman J, Kondo K, Moll J, Ponta H, Herrlich P (1997) Variant exons v6 and v7 together expand the repertoire of glycosaminoglycans bound by CD44. J Biol Chem 272: 31837-31844
20. Sleeman J P, Arming S, Moll J F, Hekele A, Rudy W, Sherman L S, Kreil G, Ponta H, Herrlich P (1996) Hyaluronate-independent metastatic behavior of CD44 variant-expressing pancreatic carcinoma cells. Cancer Res 56: 3134-3141
21. Tao K, Fang M, Alroy J, Sahagian G G (2008) Imagable 4T1 model for the study of late stage breast cancer. BMC Cancer 8: 228-228
22. Umekita Y, Ohi Y, Sagara Y, Yoshida H (2000) Co-expression of epidermal growth factor receptor and transforming growth factor-alpha predicts worse prognosis in breast-cancer patients. International Journal of Cancer Journal International Du Cancer 89: 484-487
23. Wu W K K, Tse T T M, Sung J J Y, Li Li, Yu L, Ch C H (2009) Expression of ErbB Receptors and their Cognate Ligands in Gastric and Colon Cancer Cell Lines. Anticancer Research 29: 229-234

The invention claimed is:

1. A method for inhibiting breast cancer tumor growth in a human being diagnosed with breast cancer, wherein said breast cancer shows expression of CD44v6, comprising administering a compound to the human being in need thereof, wherein said compound comprises:

(i) a peptide comprising at least the amino acid sequence $X_1$-R-W-H-$X_5$ (SEQ ID NO: 1) with $X_1$ being an amino acid selected from the group consisting of A, C, D, E, F, G, H, I, K, L, M, N, P, Q, R, S, T, V, W, and Y and $X_5$ being an amino acid selected from the group consisting of A, C, D, E, F, G, H, I, K, L, M, N, P, Q, R, S, T, V, W, and Y, or a peptidomimetic thereof, or (ii) a peptide comprising at least 5, 6, 7, 8, 9, 10, 11, 12, 13, or 14 amino acids of amino acid sequence $X_1$-$X_2$-$X_3$-$X_4$-$X_5$-$X_6$-$X_7$-R-W-H-$X_{11}$-$X_{12}$-$X_{13}$-$X_{14}$ (SEQ ID NO: 7), wherein $X_1$, $X_2$, $X_3$, $X_4$, $X_5$, $X_6$, $X_7$, $X_{11}$, $X_{12}$, $X_{13}$, or $X_{14}$ is an amino acid selected from the group consisting of A, C, D, E, F, G, H, I, K, L, M, N, P, Q, R, S, T, V, W, and Y, and wherein the peptide comprises at least $X_7$-R-W-H-$X_{11}$ of SEQ ID NO: 7, wherein $X_7$ and $X_{11}$ is an amino acid selected from the group consisting of A, C, D, E, F, G, H, I, K, L, M, N, P, Q, R, S, T, V, W, and Y, or a peptidomimetic thereof.

2. The method of claim 1, wherein said compound comprises:

(i) a peptide comprising at least the amino acid sequence $X_1$-R-W-H-$X_5$ (SEQ ID NO: 4) wherein $X_1$ is an amino acid selected from the group consisting of amino acids with an $NH_2$ group side chain and amino acids with non-polar side chains, and wherein $X_5$ is an amino acid selected from the group consisting of amino acids with negatively charged side chains and amino acids with non-polar side chains or a peptidomimetic thereof, or (ii) a peptide comprising at least 5, 6, 7, 8, 9, 10, 11, 12, 13, or 14 amino acids of amino acid sequence $X_1$-$X_2$-$X_3$-$X_4$-$X_5$-$X_6$-$X_7$-R-W-H-$X_{11}$-$X_{12}$-$X_{13}$-$X_{14}$ (SEQ ID NO: 8), wherein $X_1$ is an amino acid selected from the group consisting of amino acids with an $NH_2$ group side chain and amino acids with non-polar side chains, wherein $X_2$ is an amino acid selected from the group consisting of amino acids with negatively charged side chains and amino acids with non-polar side chains, wherein $X_3$ is an amino acid selected from the group consisting of amino acids with an $NH_2$ group side chain and amino acids with non-polar side chains, wherein $X_4$ is an amino acid selected from the group consisting of amino acids with non-polar or non-charged side chains and aromatic ring structures and amino acids with non-polar side chains, wherein $X_5$ is an amino acid selected from the group consisting of amino acids with non-polar or non-charged side chains and aromatic rings structures and amino acids with non-polar side chains, wherein $X_6$ is an amino acid selected from the group consisting of G and amino acids with non-polar side chains, wherein $X_7$ is an amino acid selected from the group consisting of amino acids with an $NH_2$ group side chain and amino acids with non-polar side chains, wherein $X_{11}$ is an amino acid selected from the group consisting of amino acids with negatively charged side chains and amino acids with non-polar side chains, wherein $X_{12}$ is an amino acid selected from the group consisting of G and amino acids with non-polar side chains, wherein $X_{13}$ is an amino acid selected from the group consisting of amino acids with non-polar or non-charged side chains and aromatic ring structures and amino acids with non-polar side chains, and wherein $X_{14}$ is an amino acid selected from the group consisting of amino acids with an $NH_2$ group side chain and amino acids with non-polar side chains, and wherein the peptide comprises at least $X_7$-R-W-H-$X_{11}$ of SEQ ID NO: 8, wherein $X_7$ is an amino acid selected from the group consisting of amino acids with an $NH_2$ group side chain and amino acids with non-polar side chains, and wherein $X_{11}$ is an amino acid selected from the group consisting of amino acids with negatively charged side chains and amino acids with non-polar side chains, or a peptidomimetic thereof.

3. The method of claim 1, wherein said compound comprises:

(i) a peptide comprising at least the amino acid sequence $X_1$-R-W-H-$X_5$ (SEQ ID NO: 5) wherein $X_1$ is an amino acid selected from the group consisting of amino acids with an $NH_2$ group side chain, and wherein $X_5$ is an amino acid selected from the group consisting of amino acids with negatively charged side chains or a peptidomimetic thereof, or (ii) a peptide comprising at least 5, 6, 7, 8, 9, 10, 11, 12, 13, or 14 amino acids of amino acid sequence $X_1$-$X_2$-$X_3$-$X_4$-$X_5$-$X_6$-$X_7$-R-W-H-$X_{11}$-$X_{12}$-$X_{13}$-$X_{14}$ (SEQ ID NO: 9), wherein $X_1$ is an amino acid selected from the group consisting of amino acids with an $NH_2$ group side chain, wherein $X_2$ is an amino acid selected from the group consisting of amino acids with negatively charged side chains, wherein $X_3$ is an amino acid selected from the group consisting of amino acids with an $NH_2$ group side chain, wherein $X_4$ is an amino acid selected from the group consisting of amino acids with non-polar or non-charged side chains and aromatic ring structures, wherein $X_5$ is an amino acid selected from the group consisting of amino acids with non-polar or non-charged side chains and aromatic rings-structures, wherein $X_6$ is an amino acid selected from the group consisting of G and amino acids with non-polar side chains, wherein $X_7$ is an amino acid selected from the group consisting of amino acids with an $NH_2$ group side chain, wherein $X_{11}$ is an amino acid selected from the group consisting of amino acids with negatively charged side chains, wherein $X_{12}$ is an amino acid selected from the group consisting of G and amino acids with non-polar side chains, wherein $X_{13}$ is an amino acid selected from the group consisting of amino acids with non-polar or non-charged side chains and amino acids with aromatic ring structures, and wherein $X_{14}$ is an amino acid selected from the group consisting of amino acids with an $NH_2$ group side chain, and wherein the peptide comprises at least $X_7$-R-W-H-$X_{11}$ of SEQ ID NO: 9 wherein $X_7$ is an amino acid selected from the group consisting of amino acids with an $NH_2$ group side chain, and wherein $X_{11}$ is an amino acid selected from the group consisting of amino acids with negatively charged side chains, or a peptidomimetic thereof.

4. The method of claim 1, wherein said compound comprises a peptide comprising the amino acid sequence N-R-W-H-E (SEQ ID NO: 2), or the amino acid sequence K-E-Q-W-F-G-N-R-W-H-E-G-Y-R (SEQ ID NO: 6), or a peptidomimetic thereof.

5. The method of claim 1, wherein said compound is a modified form of said peptide or said peptidomimetic.

6. The method of claim 5, wherein said compound is a pegylated, hesylated, pasylated, myristoylated, glycosylated, and/or cyclic form of said peptide or peptidomimetic.

7. The method of claim 1, wherein the compound is formulated for oral, nasal, or subcutaneous administration.

8. The method of claim 1, wherein said breast cancer shows protein overexpression of v-erb-b2 erythroblastic leukemia viral oncogene homolog 1 (ErbB1) and/or v-erb-b2 erythroblastic leukemia viral oncogene homolog 2 (ErbB2).

9. The method of claim 1, wherein said breast cancer shows no constitutive ErbB2 activation.

10. The method of claim 1, wherein said breast cancer shows protein overexpression of epidermal growth factor (EGF) and/or estrogen receptor (ER).

11. The method of claim 1, wherein said breast cancer shows protein overexpression of EGF and/or ER, but not of transforming growth factor alpha (TGFα).

12. The method of claim 1, wherein said breast cancer tumor shows EGF-based ErbB activation.

13. The method of claim 1, wherein said breast cancer is resistant to treatment with trastuzumab or pertuzumab.

14. The method of claim 1, wherein said breast cancer is resistant to treatment with trastuzumab or pertuzumab and shows protein overexpression of met proto-oncogene (Met).

15. The method of claim 1, wherein said breast cancer is a metastasizing breast cancer.

16. The method of claim 1, wherein said breast cancer is classifiable as Stage III or Stage IV according to the tumor nodes metastasis (TNM) anatomic/prognostic group system of the cancer staging system of the American Joint Committee on Cancer.

* * * * *

UNITED STATES PATENT AND TRADEMARK OFFICE
CERTIFICATE OF CORRECTION

PATENT NO. : 9,586,994 B2
APPLICATION NO. : 14/407330
DATED : March 7, 2017
INVENTOR(S) : Veronique Orlan-Rousseau et al.

It is certified that error appears in the above-identified patent and that said Letters Patent is hereby corrected as shown below:

On the Title Page

Item (71), Applicants, Line 1:
"KARLSRUHER INSTITUT FÜR TECHNOLOGIE, Eggenstein-Leopoldshafen (DE);" should be removed.

Signed and Sealed this
Eighth Day of May, 2018

Andrei Iancu
*Director of the United States Patent and Trademark Office*